US012630612B2

(12) United States Patent
Henderson et al.

(10) Patent No.: US 12,630,612 B2
(45) **Date of Patent: \*May 19, 2026**

(54) SINGLE CHAIN INTRABODIES THAT ALTER HUNTINGTIN MUTANT DEGRADATION

(71) Applicant: Vybion, Inc., Monterey, CA (US)

(72) Inventors: Lee Alan Henderson, Monterey, CA (US); Irene Alexandra Amaro, Monterey, CA (US)

(73) Assignee: Vybion, Inc., Monterey, CA (US)

( \* ) Notice: Subject to any disclaimer, the term of this patent is extended or adjusted under 35 U.S.C. 154(b) by 1308 days.

This patent is subject to a terminal disclaimer.

(21) Appl. No.: 17/384,408

(22) Filed: Jul. 23, 2021

(65) Prior Publication Data

US 2022/0064269 A1 Mar. 3, 2022

Related U.S. Application Data

(60) Division of application No. 15/900,563, filed on Feb. 20, 2018, now Pat. No. 11,072,650, which is a division of application No. 14/731,353, filed on Jun. 4, 2015, now Pat. No. 9,932,394, which is a continuation of application No. PCT/US2014/037563, filed on May 9, 2014.

(60) Provisional application No. 61/871,288, filed on Aug. 28, 2013, provisional application No. 61/828,625, filed on May 29, 2013.

(51) Int. Cl.
*C07K 16/18* (2006.01)
*A61K 39/00* (2006.01)

(52) U.S. Cl.
CPC ........ *C07K 16/18* (2013.01); *A61K 2039/505* (2013.01); *C07K 2317/565* (2013.01); *C07K 2317/622* (2013.01); *C07K 2317/76* (2013.01); *C07K 2317/80* (2013.01)

(58) Field of Classification Search
None
See application file for complete search history.

(56) References Cited

U.S. PATENT DOCUMENTS

| | | | |
|---|---|---|---|
| 8,242,105 | B2 | 8/2012 | Kuehne et al. |
| 9,932,394 | B2 | 4/2018 | Henderson et al. |
| 2003/0232052 | A1 | 12/2003 | Khoshnan et al. |
| 2005/0226863 | A1 | 10/2005 | Colby et al. |
| 2010/0233180 | A1 | 9/2010 | Khoshnan et al. |
| 2017/0044241 | A1 | 2/2017 | Henderson et al. |
| 2018/0319874 | A1 | 11/2018 | Henderson et al. |

FOREIGN PATENT DOCUMENTS

| | | |
|---|---|---|
| AU | 2014272024 B2 | 12/2014 |
| CN | 105531287 B | 1/2020 |
| WO | WO-1994/29457 A2 | 12/1994 |
| WO | WO-2005/052002 A2 | 6/2005 |
| WO | WO-2008/151833 A2 | 12/2008 |
| WO | WO-2013/043669 A1 | 3/2013 |
| WO | WO-2014/193632 A2 | 12/2014 |

OTHER PUBLICATIONS

Takahashi et al (J Mol Cell Biol 2: 180-191, 2010) (Year: 2010).\*
Fan et al, (Cell Transplant 23: 441-458, 2014) (Year: 2014).\*
Dentatorubral-pallidoluysian atrophy—Wikipedia, downloaded Mar. 24, 2025, 8 pages (Year: 2025).\*
Chye et al (CNS Neurol dis—Drug targets, 17: 1-9, 2018) (Year: 2018).\*
Amaro et al, (J Neurodegen Dis 2016: 1-10, 2016) (Year: 2016).\*
Wu et al., "Humanization of a Murine Monoclonal Antibody by Simultaneous Optimization of Framework and CDR Residues", Journal of Molecular Biology, vol. 294, Nov. 1999, pp. 151-162.
European Patent Office, Supplementary Search Report and Opinion, European Patent Application No. 14803776.5, May 11, 2017, twelve pages.
Khoshnan, A. et al., "Effects of intracellular expression of anti-huntingtin antibodies of various specificities on mutant huntingtin aggregation and toxicity," Proceedings National Academy of Sciences PNAS, National Academy of Sciences, Jan. 22, 2002, pp. 1002-1007, vol. 99, No. 2, XP002401586.
Southwell, A., et al., "Intrabodies Binding the Praline-Rich Domains of Mutant Huntingtin Increase its Turnover and Reduce Neurotoxicity," The Journal of Neuroscience, Sep. 3, 2008, pp. 9013-9020, vol. 28, No. 36, XP-002752703.
PCT International Search Report and Written Opinion, PCT Application No. PCT/US2014/037563, Jan. 22, 2015, thirteen pages.
Liu, K.-Y., et al., "Disruption of the nuclear membrane by perinuclear inclusions of mutant huntingtin causes cell-cycle re-entry and striatal cell death in mouse and cell models of Huntington's disease," Human Molecular Genetics, 2015, vol. 24, No. 6, pp. 1602-1616.
Van Hagen, M., et al., "The dynamics of early-state transcriptional changes and aggregate formation in a Huntington's disease cell model," BMC Genomics. May 12, 2017, vol. 18, No. 373, 14 Pages.
Amaro, A., et al., "An Intrabody Drug (rAAV6-INT41) Reduces the Binding of N-Terminal Huntingtin Fragment(s) to DNA to Basal Levels in PC12 Cells and Delays Cognitive Loss in the R6/2 Animal Model," Journal of Neurodegenerative Diseases, Jun. 27, 2016, vol. 2016, Article ID 7120753, 10 pages.
De Pascalis, et al., "Grafting of "Abbreviated" Complementarity-Determining Regions Containing Specificity-Determining Residues Essential for Ligand Contact to Engineer a Less Immunogenic Humanized Monoclonal Antibody," J Immunol,, vol. 169, pp. 3076-3084, 2002.
Huntingtin protein—NCBI, downloaded on Jul. 7, 2017, 6 pages, can be retrieved at <https://www.ncbi.nlm.nih.gov/protein/NP002102.4>.

(Continued)

*Primary Examiner* — Kimberly Ballard
*Assistant Examiner* — Aditi Dutt
(74) *Attorney, Agent, or Firm* — Goodwin Procter LLP

(57) ABSTRACT

Compositions and methods of use are provided for intrabodies that bind and alter the effects of poly-glutamate protein aggregation in poly-glutamate associated diseases, such as in Huntington's disease. Intrabodies are provided that prevent poly-glutamate aggregation, gene dysregulation, and negative effects of Huntington's disease.

10 Claims, 22 Drawing Sheets

Specification includes a Sequence Listing.

(56)          References Cited

OTHER PUBLICATIONS

Legleiter, J. et al., "Monoclonal Antibodies Recognize Distinct Conformational Epitopes Formed by Polyglutamine in a Mutant Huntingtin Fragment," The Journal of Biological Chemistry, Aug. 7, 2009, pp. 21647-21658, vol. 284, No. 32.

Maccallum, R., et al., "Antibody-antigen Interactions: Contact Analysis and Binding Site Topography," J. Mol. Biol., vol. 262, pp. 732-745, 1996.

Paul, W, "Fundamental Immunology," (textbook) pp. 292-295, 1993.

Rudikoff, S., et al., "Single amino acid substitution altering antigen-binding specificity," PNAS USA, vol. 79, pp. 1979-1983, 1982.

Vajdos, F., et al., "Comprehensive Functional Maps of the Antigen-binding Site of an Anti-ErbB2 Antibody Obtained with Shotgun Scanning Mutagenesis," J. Mol. Biol., 2002, vol. 320, pp. 415-428.

Non-Final Office Action for U.S. Appl. No. 14/731,353, 115 pages.

Non-Final Office Action for U.S. Appl. No. 15/900,563, 50 pages.

Takahashi et al., "Polyglutamine Diseases: Where does Toxicity Come from? What is Toxicity? Where are We Going?", Journal of Molecular Cell Biology (2010), 2, 180-191.

Fan et al. "Polyglutamine (PolyQ) Diseases: Genetics to Treatments" *Cell Transplantation*, vol. 23, pp. 441-458, 2014.

Eastwood et al., "The Plant Cell Wall—Decomposing Machinery Underlies the Functional Diversity of Forest Fungi" (333):762-765, Science (2011).

* cited by examiner

Concentration (nM) of
Purified Intrabody

Concentration (nM) of
Purified Intrabody

Concentration (nM) of
Purified Intrabody

```
                    VH-CDR1                                              VH-CDR2
SEQ ID NO:5    MAEVQLVVSGGGLVKPGGSMILSCAASGFTFSNYSMNWVRQAPGKGLEWVSSISSSSEYIYYADFVKGRFTISRDNAKNS
               ----------+---------+---------+---------+---------+---------+---------+---------+
                        10        20        30        40        50        60        70        80
               ----------+---------+---------+---------+---------+---------+---------+---------+
SEQ ID NO:2    MAEVQLVVSGGGLVKPGGSMILSCAASGFTFSNYSMNWVRQAPGKGLEWVSSISSSSEYIYYADFVKGRFTISRDNAKNS   80
SEQ ID NO:1    MAEVQLVVSGGGLVKPGGSMILSCAASGFTFSNYSMNWVRQAPGKGLEWVSSISSSSEYIYYADFVKGRFTISRDNAKNS   80
SEQ ID NO:3    MAEVQLVVSGGGLVKPGGSMILSCAASGFTFSNYSMNWVRQAPGKGLEWVSSISSSSEYIYYADFVKGRFTISRDNAKNS   80
SEQ ID NO:4    MAEVQLVVSGGGLVKPGGSMILSCAASGFTFSNYSMNWVRQAPGKGLEWVSSISSSSEYIYYADFVKGRFTISRDNAKNS   80
                              VH-CDR3                   Linker
SEQ ID NO:5    LYLQMDSLRAEDTAVYYCAXWPCXXX-XTWGRGTLVTVSSGEGGSGEGGESGGGGSQSVLTQPASVSGSPGQSITISCXNS
               ----------+---------+---------+---------+---------+---------+---------+---------+
                        90       100       110       120       130       140       150       160
               ----------+---------+---------+---------+---------+---------+---------+---------+
SEQ ID NO:2    LYLQMDSLRAEDTAVYYCAHWPRLWRFPIWGRGTLVTVSSGGGGSGGGGSGGGGSQSVLTQPASVSGSPGQSITISCAGT  160
SEQ ID NO:1    LYLQMDSLRAEDTAVYYCA-WPGYR--KAWGRGTLVTVSSGGGGSGGGGSGGGGSQSVLTQPASVSGSPGQSITISCAGT  157
SEQ ID NO:3    LYLQMDSLRAEDTAVYYCAITGCEC---TWGRGTLVTVSSGGGGSGGGGSGGGGSQSVLTQPASVSGSPGQSITISCAGT  157
SEQ ID NO:4    LYLQMDSLRAEDTAVYYCAAAVCNGRPDTWGRGTLVTVSSGGGGSGGGGSGGGGSQSVLTQPASVSGSPGQSITISCAGT  160
               VL-CDR1                   VL-CDR2                                  VL-CDR3
SEQ ID NO:5    SSDVGGYNYVSWYQQHPGKAPKLMIYEDSKRPSGVSNRFSGSKSGNTASLTISGLRAEDEADYYCS-XXXXLRWAXFGGG
               ----------+---------+---------+---------+---------+---------+---------+---------+
                       170       180       190       200       210       220       230       240
               ----------+---------+---------+---------+---------+---------+---------+---------+
SEQ ID NO:2    SSDVGGYNYVSWYQQHPGKAPKLMIYEDSKRPSGVSNRFSGSKSGNTASLTISGLRAEDEADYYC---VLNMHWANFGGG  237
SEQ ID NO:1    SSDVGGYNYVSWYQQHPGKAPKLMIYEDSKRPSGVSNRFSGSKSGNTASLTISGLRAEDEADYYCSYCASKGHWL-PGGG  236
SEQ ID NO:3    SSDVGGYNYVSWYQQHPGKAPKLMIYEDSKRPSGVSNRFSGSKSGNTASLTISGLRAEDEADYYCS-CIRGLKAAYFGGG  236
SEQ ID NO:4    SSDVGGYNYVSWYQQHPGKAPKLMIYEDSKRPSGVSNRFSGSKSGNTASLTISGLRAEDEADYYCG---YSLLPVLFGGG  237

SEQ ID NO:5    TKLAVLGAAAEQKLIS
               ----------+-----
                       250
               ----------+-----
SEQ ID NO:2    TKLAVLGAAAEQKLIS                                                                253
SEQ ID NO:1    TKLAVLGAAAEQKLIS                                                                252
SEQ ID NO:3    TKLAVLGAAAEQKLIS                                                                252
SEQ ID NO:4    TKLAVLGAAAEQKLIS                                                                253
```

FIG. 2

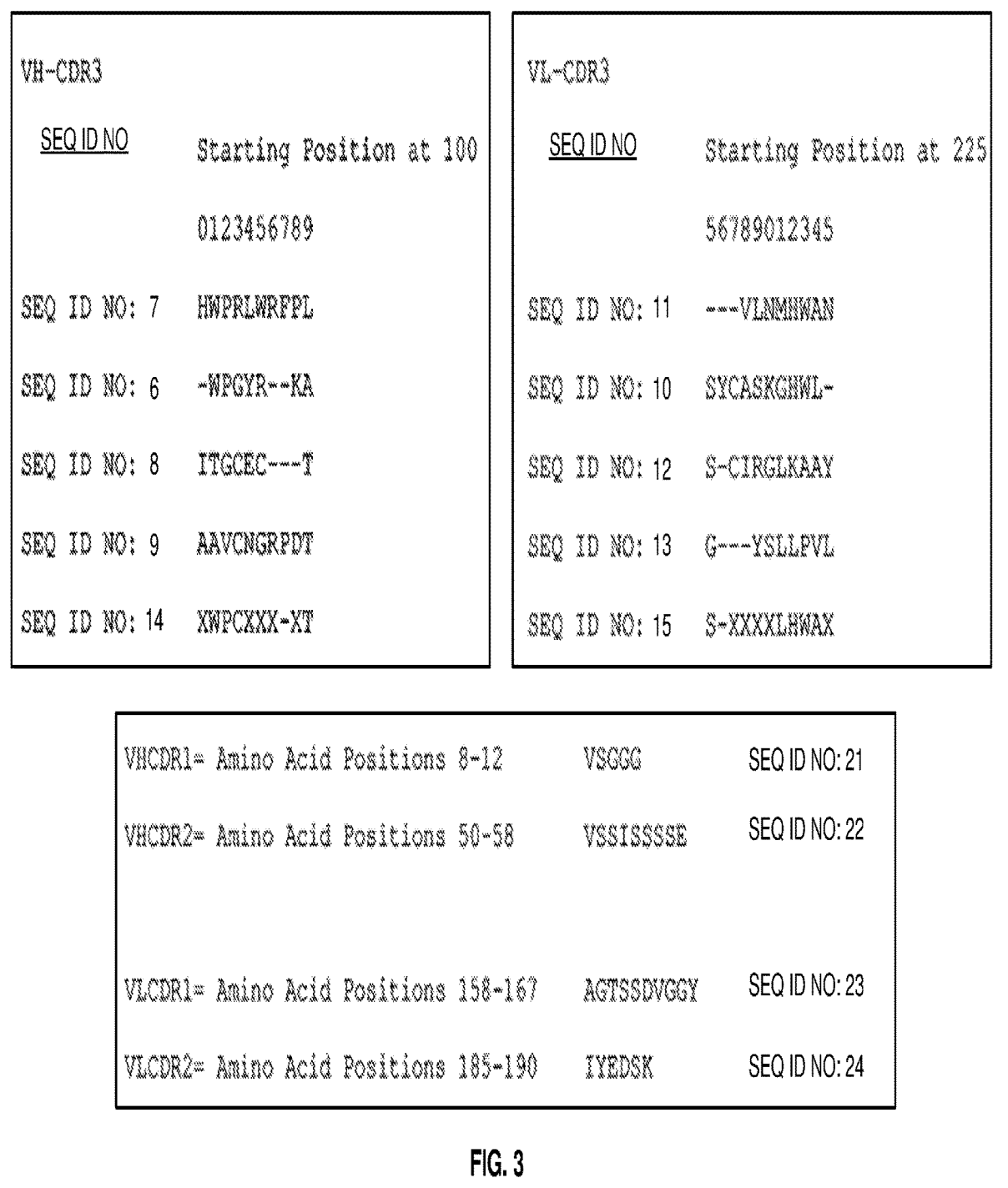

VH-CDR3

SEQ ID NO        Starting Position at 100

0123456789

SEQ ID NO: 7     HWPRLWRFPL

SEQ ID NO: 6     -WPGYR--KA

SEQ ID NO: 8     ITGCEC---T

SEQ ID NO: 9     AAVCNGRPDT

SEQ ID NO: 14    XWPCXXX-XT

VL-CDR3

SEQ ID NO        Starting Position at 225

56789012345

SEQ ID NO: 11    ---VLNMHWAN

SEQ ID NO: 10    SYCASKGHWL-

SEQ ID NO: 12    S-CIRGLKAAY

SEQ ID NO: 13    G---YSLLPVL

SEQ ID NO: 15    S-XXXXLHWAX

VHCDR1= Amino Acid Positions 8-12       VSGGG        SEQ ID NO: 21

VHCDR2= Amino Acid Positions 50-58      VSSISSSSE    SEQ ID NO: 22

VLCDR1= Amino Acid Positions 158-167    AGTSSDVGGY   SEQ ID NO: 23

VLCDR2= Amino Acid Positions 185-190    IYEDSK       SEQ ID NO: 24

FIG. 3

60k cells - settings changed FL1 430 gain 1

| sample | plasmids | #cells total | #cells gated | gfp fluorescence (% of 100) | | |
|--------|----------|--------------|--------------|-----|--------|------|
|        |          |              |              | ≤5 | 5to100 | >100 |
| 0 | 293T | 60056 | 54741 | 99.9 | 0.007 | 0.002 |
| 1 | 293T + pQ30 | 61847 | 57796 | 66.4 | 24.2 | 9.42 |
| 2 | 293T + pQ103 | 61175 | 53637 | 49.7 | 27.3 | 22.9 |
| 3 | 293T + pQ103 + Happ1t | 63302 | 59979 | 72.6 | 26.9 | 0.774 |
| 4 | 293T + pQ103 + 38.1 (INT41) | 61358 | 57579 | 71.6 | 27.3 | 1.41 |
| 5 | 293T + pQ103 + 41.2 | 61575 | 58185 | 72.8 | 25.6 | 1.83 |
| 6 | 293T + pQ103 + 41.3 | 62168 | 58913 | 72 | 25.7 | 2.57 |

FIG. 5

INT41 Effect on Under Expressed Genes

Representative Under-Expressed Genes

```
  1 maeprqefev medhagtygl gdrkdqggyt mhqdqegdtd aglkesplqt ptedgseepg
 61 setsdakstp taedvtaplv degapgkqaa aqphteipeg ttaeeagigd tpsledeaag
121 hvtqepesgk vvqegflrep gppglshqlm sgmpgapllp egpreatrqp sgtgpedteg
181 grhapellkh qllgdlhqeg pplkgaggke rpgskeevde drdvdesspq dsppskaspa
241 qdgrppqtaa reatsipgfp aegaiplpvd flskvsteip asepdgpsvg rakgqdaple
301 ftfhveitpn vqkeqahsee hlgraafpga pgegpeargp slgedtkead lpepsekqpa
361 aaprgkpvsr vpqlkarmvs kskdgtgsdd kkaktstrss aktlknrpcl spkhptpgss
421 dpliqpsspa vcpeppsspk yvssvtsrtg ssgakemklk gadgktkiat prgaappgqk
481 gqanatripa ktppapktpp ssgeppksgd rsgysspgsp gtpgsrsrtp slptpptrep
541 kkvavvrtpp kspssaksrl qtapvpmpdl knvkskigst enlkhqpggg kvqiinkkld
601 lsnvqskcgs kdnikhvpgg gsvqivykpv dlskvtskcg slgnihhkpg ggqvevksek
661 ldfkdrvqsk igsldnithv pgggnkkiet hkltfrenak aktdhgaeiv ykspvvsgdt
721 sprhlsnvss tgsidmvdsp qlatladevs aslakqgl
```

FIG. 12

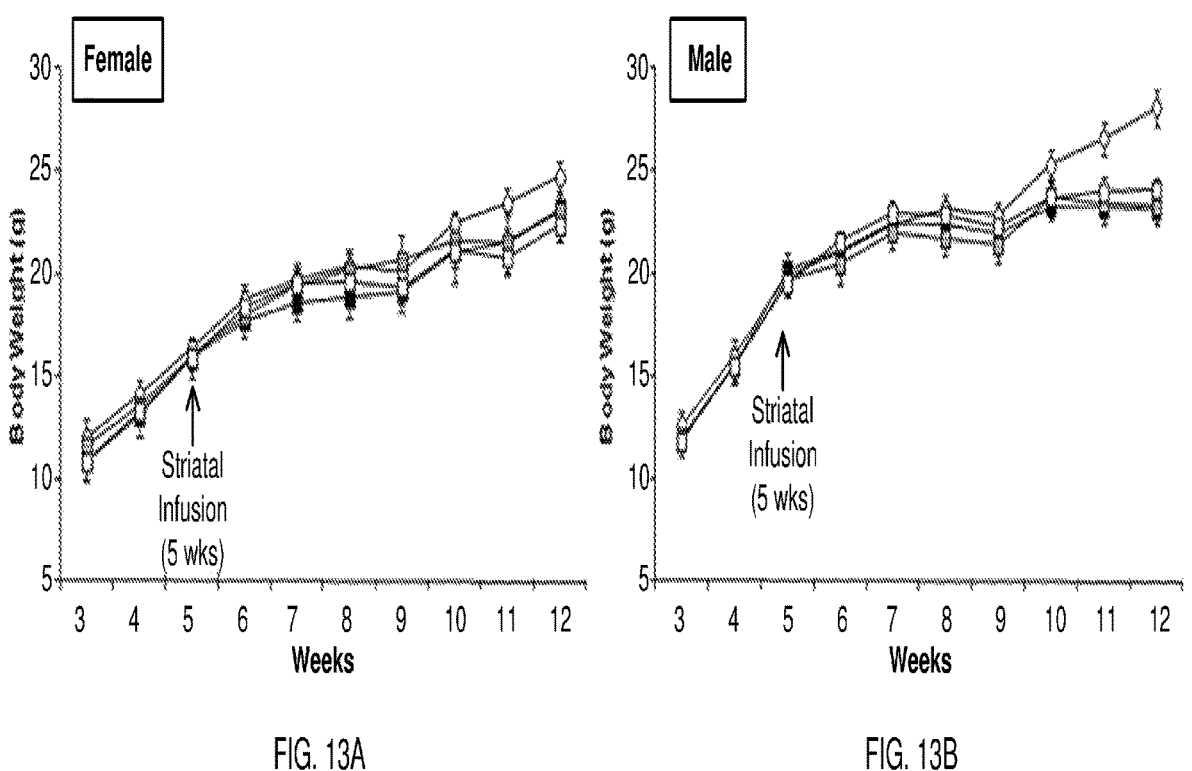
FIG. 13A                                    FIG. 13B
Legend:
Open circle: vehicle in R6/2 WT controls;
Black square: rAAV-GFP in R6/2 Tg;
Gray square: rAAV-Happ1t in R6/2 Tg;
Open square: rAAV-INT41 in R6/2 Tg

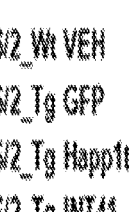
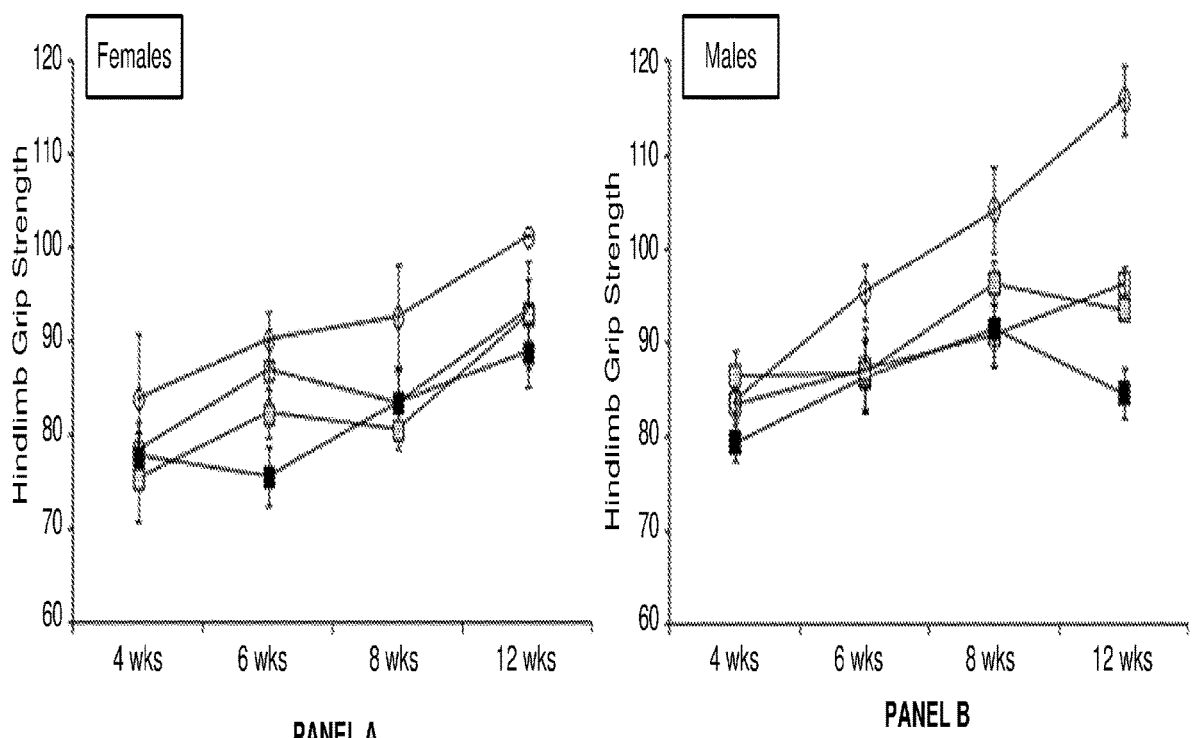
FIG. 16

SINGLE CHAIN INTRABODIES THAT ALTER HUNTINGTIN MUTANT DEGRADATION

CROSS REFERENCE TO RELATED APPLICATIONS

This application is a divisional of U.S. application Ser. No. 15/900,563, filed Feb. 20, 2018, which is a divisional of U.S. application Ser. No. 14/731,353, filed Jun. 4, 2015, which is a continuation of International Application No. PCT/US2014/037563, filed May 9, 2014, which claims the benefit of earlier filed U.S. Provisional Application No. 61/871,288, filed on Aug. 28, 2013 and U.S. Provisional Application No. 61/828,625, filed on May 29, 2013, the disclosures of which are hereby incorporated in their entirety by reference.

SEQUENCE LISTING

The instant application contains a Sequence Listing which has been submitted electronically in ASCII format and is hereby incorporated by reference in its entirety. Said ASCII copy, created on Feb. 20, 2018, is named VBI-001C1D2_SequenceListing.txt and is 31,279 bytes in size.

BACKGROUND OF THE INVENTION

Field of the Invention

The invention relates generally to compositions and methods for altering the negative effects and disease progression of poly-glutamate associated diseases, such as Huntington's disease.

Description of the Related Art

Huntington's disease is an inherited disease that causes the progressive breakdown (degeneration) of nerve cells in the brain, resulting in a cognitive and motor function decline [1, 2]. The aggregation of a mutant Huntingtin protein (Htt) in cells alters protein function and gene regulation, which causes movement, thinking (cognitive) and psychiatric disorders along with neuronal death. Most people with Huntington's disease develop signs and symptoms in their 20's or 30's, but the onset of disease may be earlier or later in life, with a patient's death typically occurring within 10-15 years of diagnosis. A juvenile form of Huntington's occurs in about 6% of patients characterized by rapid onset of symptoms and disease progression beginning in early childhood.

The genetic mutation that causes Huntington's disease is found in repeats of the amino acid glutamine (Q) near the amino terminus of the Huntingtin protein, called HttpolyQ or HttpQ. The number of repeats is generally predictive of the age of onset and progression rate in the subject. Repeats of more than 38 Q's (SEQ ID NO: 32) result in Huntington's Disease pathology. The function of the Huntingtin protein is not well characterized, but it appears to be involved in transport functions of vesicles containing neurotransmitters and other molecules needed for cell and tissue function [3, 4]. Although the mutation is found in all cells, Huntington's disease manifests predominantly in the brain.

Aggregation of HttpQ leads to abnormal and arrested degradation of the Huntingtin protein and the production of toxic degradation products that appear to enter the nucleus of the cell and play a role in gene dysregulation [5]. HttpQ fragments in the nucleus bind to transcriptional regulatory proteins that drive cellular functions [4-6]. Furthermore, toxic fragments of HttpQ that accumulate in the nucleus alter gene expression by direct binding to DNA and by altering chromatin structure [7, 8]. Several lines of evidence demonstrate that a caspase 6-cleaved fragment accumulates in the nucleus and blockage of Capsase 6 cleavage eliminates generation of the toxic nuclear fragment resulting in the absence of disease in HttpQ animals [9-11]. The patterns of gene dysregulation are well characterized and consistent in cell-based systems, in animal models that exhibit HttpQ aggregation and in patient samples taken at autopsy. The gene families mostly affected are those that regulate protein synthesis and degradation, protein folding (also known as heat shock pathways), and mitochondrial function that provide power to cells.

The subsequent loss of neurons that regulate motor function and cognition leads to progressive dementia and loss of motor control. Thus, there is a need for compositions and methods that modify the degradation process. In particular, disease modification therapy must demonstrate the ability to prevent gene dysregulation and HttpQ aggregation, which appears to be a primary factor in disease progression. To date, no disease-modifying therapeutic agents have been identified that prevent aggregation of HttpQ and modify gene dysregulation. Conventional medications and treatments lessen symptoms of movement and psychiatric disorders. For example, the only FDA approved drug for Huntington's disease (Xenazine®) provides temporary relief of chorea, a diagnostic part of motor movement dysfunction that led to the initial characterization of this disease.

The present disclosure seeks to fulfill this need and provide further related advantages.

SUMMARY OF THE INVENTION

Provided herein are compositions and methods of using intrabodies to alter disease progression in Huntington's. In an embodiment, a composition is provided comprising a single chain intrabody. The single chain intrabody comprises an amino acid sequence, comprising: a variable heavy complementarity defining region 3 (CDR3) sequence, a variable light CDR3 sequence, and a linker sequence interposed between said variable heavy CDR3 sequence and said variable light CDR3 sequence, wherein said variable heavy CDR3 sequence comprises $X_1X_2X_3X_4X_5X_6\ X_7\ X_8\ X_9X_{10}$, wherein $X_1$ is H, I, A, or no amino acid, wherein $X_2$ is W, T, or A, wherein $X_3$ is P, G, or V, wherein $X_4$ is R, G, or C, wherein $X_5$ is L, Y, E or N, wherein $X_6$ is W, R, C or G, wherein $X_7$ is R or no amino acid, wherein $X_8$ is F, P or no amino acid, wherein $X_9$ is P, K, D, or no amino acid, wherein $X_{10}$ is L, A, or T, and wherein said intrabody is capable of binding to a poly-proline sequence and reduces aggregation of a poly-glutamate tract protein in a cell.

In an embodiment, the intrabody comprises a variable heavy CDR3 sequence that comprises WPGYRKA (SEQ ID NO: 6). In another embodiment, the intrabody comprises a variable heavy CDR3 sequence that comprises HWPRLWRFPL (SEQ ID NO: 7). In yet another embodiment, the intrabody comprises a variable heavy CDR3 sequence that comprises ITGCECT (SEQ ID NO: 8). In other embodiments, the intrabody includes a variable heavy CDR3 sequence that comprises AAVCNGRPDT (SEQ ID NO: 9).

In some embodiments, the variable light CDR3 sequence comprises $X_1X_2X_3X_4X_5X_6\ X_7\ X_8\ X_9\ X_{10}X_{11}$, wherein $X_1$ is S or no amino acid, wherein $X_2$ is Y or no amino acid, wherein $X_3$ is C or no amino acid, wherein $X_4$ is V, A, I or no amino acid, wherein $X_5$ is L, S, R, or Y, wherein $X_6$ is N, K, G, or S, wherein $X_7$ is M, G or L, wherein $X_8$ is H, K, or L, wherein $X_9$ is W, A, or P, wherein $X_{10}$ is A, L, or V, and wherein $X_{11}$ is N, Y, L or no amino acid. In an embodiment, the variable light CDR3 sequence comprises SYCASKGHWL (SEQ ID NO: 10). In another embodiment, the variable light CDR3 sequence comprises VLNMHWAN (SEQ ID NO: 11). In yet another embodiment, the variable light CDR3 sequence comprises SCIRGLKAAY (SEQ ID NO: 12). In some embodiments, the variable light CDR3 sequence comprises GYSLLPVL (SEQ ID NO: 13).

In an embodiment, the variable heavy CDR3 sequence comprises WPGYRKA (SEQ ID NO: 6) and wherein said variable light CDR3 sequence comprises SYCASKGHWL (SEQ ID NO: 10). In another embodiment, the variable heavy CDR3 sequence comprises HWPRLWRFPL (SEQ ID NO: 7) and wherein said variable light CDR3 sequence comprises VLNMHWAN (SEQ ID NO: 11). In yet another embodiment, the variable heavy CDR3 sequence comprises ITGCECT (SEQ ID NO: 8) and wherein said variable light CDR3 sequence comprises SCIRGLKAAY (SEQ ID NO: 12). In other embodiments, the variable heavy CDR3 sequence AAVCNGRPDT (SEQ ID NO: 9) and the variable light CDR3 sequence comprises GYSLLPVL (SEQ ID NO: 13).

In another embodiment, the intrabody comprises an amino acid sequence comprising amino acids of positions 1-99, 110-225, and 237-256 of SEQ ID NO: 5 in FIG. 2. In some embodiments, the variable heavy CDR3 region comprises $X_1$WPCX$_5$X$_6$X$_7$X$_8$X$_9$T, and wherein $X_1$ is H, I, A or no amino acid, $X_5$ is L, Y, E, or N, $X_6$ is W, R C, or G, $X_7$ is R or no amino acid, $X_8$ is no amino acid, $X_9$ is P, K, or D, and $X_{10}$ is L, A or T (SEQ ID NO: 14).

In other embodiments, the variable light CDR3 region comprises SX$_2$X$_3$X$_4$X$_5$X$_6$LHWAX$_{10}$, wherein $X_2$ is no amino acid, $X_3$ is C or no amino acid, $X_4$ is V, A, I or no amino acid, $X_5$ is L, S, R, or Y, and $X_6$ is N, K, G or S (SEQ ID NO: 15). The linker sequence can include a glycine-rich sequence. In an embodiment, the sequence comprises SSGGGGSGGGGSGGGGS (SEQ ID NO: 16).

In yet another embodiment, the amino acid sequence of the single chain intrabody comprises SEQ ID NO: 1. In an embodiment, the amino acid sequence of the single chain intrabody comprises SEQ ID NO: 2. In another embodiment, the amino acid sequence of the single chain intrabody comprises SEQ ID NO: 3. In some embodiments, the amino acid sequence comprises SEQ ID NO: 4. In another embodiment, the amino acid sequence of the single chain intrabody consists of SEQ ID NO: 1. In an embodiment, the amino acid sequence of the single chain intrabody consists of SEQ ID NO: 2. In other embodiments, the amino acid sequence of the single chain intrabody consists of SEQ ID NO: 3. In yet other embodiments, the amino acid sequence of the single chain intrabody consists of SEQ ID NO: 4.

In some embodiments, the single chain intrabody comprises an amino acid sequence, comprising: a variable heavy complementarity defining region (CDR) sequence, a variable light CDR sequence, and a linker sequence interposed between said variable heavy CDR sequence and said variable light CDR sequence, wherein said variable light CDR sequence comprises $X_1$X$_2$X$_3$X$_4$X$_5$X$_6$ X$_7$ X$_8$ X$_9$ X$_{10}$X$_{11}$, wherein $X_1$ is S or no amino acid, wherein $X_2$ is Y or no amino acid, wherein $X_3$ is C or no amino acid, wherein $X_4$ is V, A, I or no amino acid, wherein $X_5$ is L, S, R, or Y, wherein $X_6$ is N, K, G, or S, wherein $X_7$ is M, G or L, wherein $X_8$ is H, K, or L, wherein $X_9$ is W, A, or P, wherein $X_{10}$ is A, L, or V, and wherein $X_{11}$ is N, Y, L or no amino acid, and wherein said intrabody is capable of binding to a poly-proline sequence and reduces aggregation of a poly-glutamate tract protein in a cell.

In an embodiment, the variable light CDR sequence comprises SYCASKGHWL (SEQ ID NO: 10). In another embodiment, the variable light CDR sequence comprises VLNMHWAN (SEQ ID NO: 11). In yet another embodiment, the variable light CDR sequence comprises SCIRGL-KAAY (SEQ ID NO: 12). In some embodiments, the variable light CDR sequence comprises GYSLLPVL (SEQ ID NO: 13). The variable heavy CDR sequence can comprise WPGYRKA (SEQ ID NO: 6). In other embodiments, the variable heavy CDR sequence comprises HWPRLWRFPL (SEQ ID NO: 7). The variable heavy CDR sequence can comprise ITGCECT (SEQ ID NO: 8). In yet other embodiments, the variable heavy CDR sequence AAVCNGRPDT (SEQ ID NO: 9). In an embodiment, the variable heavy CDR sequence comprises WPGYRKA (SEQ ID NO: 6) and wherein said variable light CDR sequence comprises SYCASKGHWL (SEQ ID NO: 10).

In certain aspects, the variable heavy CDR sequence comprises HWPRLWRFPL (SEQ ID NO: 7) and wherein said variable light CDR sequence comprises VLNMHWAN (SEQ ID NO: 11). In other aspects, the variable heavy CDR sequence comprises ITGCECT (SEQ ID NO: 8) and wherein said variable light CDR sequence comprises SCIR-GLKAAY (SEQ ID NO: 12). In one aspect, the variable heavy CDR sequence comprises AAVCNGRPDT (SEQ ID NO: 9) and wherein said variable light CDR sequence comprises GYSLLPVL (SEQ ID NO: 13).

In other embodiments, the intrabody comprises an amino acid sequence comprising amino acids of positions 1-99, 110-225, and 237-256 of SEQ ID NO: 5 in FIG. 2.

In some aspects, the variable heavy CDR region comprises $X_1$WPCX$_5$X$_6$X$_7$X$_8$X$_9$T, and wherein $X_1$ is H, I, A or no amino acid, $X_5$ is L, Y, E, or N, $X_6$ is W, R C, or G, $X_7$ is R or no amino acid, $X_8$ is no amino acid, $X_9$ is P, K, or D, and $X_{10}$ is L, A or T (SEQ ID NO: 14). In other aspects, the variable light CDR region comprises SX$_2$X$_3$X$_4$X$_5$X$_6$LHWAX$_{10}$, wherein $X_2$ is no amino acid, $X_3$ is C or no amino acid, $X_4$ is V, A, I or no amino acid, $X_5$ is L, S, R, or Y, and $X_6$ is N, K, G or S (SEQ ID NO: 15).

In an embodiment, the linker sequence comprises a gly-cine-rich sequence. In another embodiment, the sequence comprises SSGGGGSGGGGSGGGGS (SEQ ID NO: 16).

In yet another embodiment, the amino acid sequence of the single chain intrabody comprises SEQ ID NO: 1. The amino acid sequence of the single chain intrabody comprises SEQ ID NO: 2. In some embodiments, the amino acid sequence of the single chain intrabody comprises SEQ ID NO: 3. In an embodiment, the amino acid of the single chain intrabody comprises SEQ ID NO: 4.

In some embodiments, the amino acid sequence of the single chain intrabody consists of SEQ ID NO: 1. In other embodiments, the amino acid sequence of the single chain intrabody consists of SEQ ID NO: 2. In another embodiment, the amino acid sequence of the single chain intrabody consists of SEQ ID NO: 3. In other embodiments, the amino acid sequence of the single chain intrabody consists of SEQ ID NO: 4.

In one aspect, the intrabody is capable of binding to a Huntingtin (HttpQ) protein. In an embodiment, the poly-glutamate tract is a Huntingtin (HttpQ) protein. In another embodiment, the intrabody reduces expression of over-expressed genes caused by aggregation of said HttpQ protein. In some embodiments, the intrabody increases expression of under-expressed genes caused by aggregation of said HttpQ protein.

In another aspect, the poly-proline sequence comprises PQLPQPPPQAQP (SEQ ID NO: 17). In certain aspects, the poly-proline sequence comprises PGPAVAEEPLHRP (SEQ ID NO: 18). In other aspects, the poly-proline sequence comprises PXP, and wherein X is any amino acid.

In an embodiment, the intrabody prevents gene dysregulation caused by aggregation of a poly-glutamate tract protein. In another embodiment, the intrabody blocks the ability of a toxic fragment of the mutant Huntingtin protein from binding to chromatin as a cause of gene dysregulation. In an embodiment, INT41 reduces the binding of a transcriptional regulator to chromatin in the nucleus. In yet another embodiment, the intrabody prevents accumulation of the poly-glutamate tract protein on cellular membranes.

Aspects of the invention include a pharmaceutical composition for reducing aggregation of a poly-glutamine tract protein in a subject, comprising said intrabody as described herein and a pharmaceutically acceptable carrier. In an embodiment, the pharmaceutically acceptable carrier comprises a delivery agent. In another embodiment, the poly-glutamine tract protein is a Huntingtin (HttpQ) protein.

Other aspects of the invention comprise a vector comprising a nucleic acid sequence encoding said intrabody as described herein. In one aspect, the vector is a viral vector. In another aspect, the vector is a recombinant adeno-associated virus. Another aspect of the invention comprises an isolated cell comprising said intrabody as described herein.

The invention includes methods for preventing aggregation of a poly-glutamine (polyQ) protein in a cell, comprising: (a) introducing into said cell said intrabody as described herein; (b) maintaining said cell produced in step (a) for a time sufficient for said intrabody to bind to said polyQ protein, thereby preventing aggregation of polyQ proteins in said cell.

In some embodiments, the invention includes a method for preventing gene dysregulation caused by aggregation of a poly-glutamine (polyQ) protein in a cell, comprising: (a) introducing into said cell said intrabody as described herein; (b) maintaining said cell produced in step (a) for a time sufficient for said intrabody to bind to said polyQ protein or fragment thereof, thereby preventing gene dysregulation of one or more genes in said cell. In some aspects, the one or more genes comprise genes listed in Table 2. In another embodiment, the polyQ protein is a Huntingtin (HttpQ) protein.

Another aspect of the invention comprises a method of treating or managing a subject having a disease associated with aggregation of a poly-glutamine protein in a cell, comprising administering to a subject in need of such treatment or management a therapeutically effective amount of said intrabody as described herein. In an embodiment, the disease comprises Huntington's disease, spinobulbar muscular atrophy (SBMA), dentatorubral and pallidoluysian atrophy, or spinocerebellar ataxia. In another embodiment, the poly-glutamine protein is a Huntingtin (HttpQ) protein. In yet another embodiment, the subject is mammalian. In other embodiments, the subject is a human.

The invention includes a single chain intrabody comprising an amino acid sequence, comprising: a variable heavy complementarity defining region 3 (CDR3) sequence, a variable light CDR3 sequence, and a linker sequence interposed between said variable heavy CDR3 sequence and said variable light CDR3 sequence, wherein said variable heavy CDR3 sequence comprises SEQ ID NO:6, wherein said variable light CDR3 sequence comprises SEQ ID NO:10, and wherein said intrabody is capable of binding to a protein sequence of a human Tau protein. In some embodiments, the variable heavy CDR sequence comprises WPGYRKA (SEQ ID NO:6). In other embodiments, the variable light CDR sequence comprises SYCASKGHWL (SEQ ID NO:10). In yet other embodiments, the variable heavy CDR sequence comprises WPGYRKA (SEQ ID NO:6) and wherein said variable light CDR sequence comprises SYCASKGHWL (SEQ ID NO:10). In an embodiment, the amino acid sequence comprises SEQ ID NO:1. In another embodiment, the amino acid sequence consists of SEQ ID NO:1. In yet another embodiment, the intrabody binds to one or more epitopes in the Tau protein.

The invention also includes a method of treating or managing a subject having Alzheimer's disease or other Tau pathologies, comprising administering to a subject in need of such treatment or management a therapeutically effective amount of the intrabody described herein. In an embodiment, the intrabody prevents binding of a Tau fragment to neurons causing neuron dysfunction.

In some embodiments, the invention comprises a single chain intrabody comprising an amino acid sequence, comprising: a variable heavy complementarity defining region 3 (CDR3) sequence, a variable light CDR3 sequence, and a linker sequence interposed between said variable heavy CDR3 sequence and said variable light CDR3 sequence, wherein said variable heavy CDR3 sequence comprises SEQ ID NO:6, wherein said variable light CDR3 sequence comprises SEQ ID NO:10, and wherein said intrabody is capable of binding to a protein sequence of a human Tau protein.

In an embodiment, the variable heavy CDR sequence comprises WPGYRKA (SEQ ID NO:6). In another embodiment, the variable light CDR sequence comprises SYCASKGHWL (SEQ ID NO:10). In some embodiments, the variable heavy CDR sequence comprises WPGYRKA (SEQ ID NO:6) and wherein said variable light CDR sequence comprises SYCASKGHWL (SEQ ID NO:10). In certain embodiments, the amino acid sequence comprises SEQ ID NO:1. In another embodiment, the amino acid sequence consists of SEQ ID NO:1. In yet another embodiment, the intrabody binds to one or more epitopes in the Tau protein.

The invention comprises a method of treating or managing a subject having Alzheimer's disease or other Tau pathologies, comprising administering to a subject in need of such treatment or management a therapeutically effective amount of the intrabodies described herein. In an embodiment, the intrabody prevents binding of a Tau fragment to neurons causing neuron dysfunction.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1A shows binding for INT41 (SEQ ID NO: 1). FIG. 1B shows binding for A2 (SEQ ID NO: 2). FIG. 1C shows binding for E10 (SEQ ID NO:3). FIG. 1D shows binding for H8 (SEQ ID NO: 4). INT41 was the strongest binder, showing higher optical density units at higher intra-body concentration.

FIG. 2 shows the sequences of the selected scFvs aligned using LaserGene to determine critical and consensus amino acids. A consensus sequence (SEQ ID NO:5) is shown aligned with INT41 (SEQ ID NO:1), A2 (SEQ ID NO:2), E10 (SEQ ID NO:3) and H8 (SEQ ID NO:4).

FIG. 3 shows the variable heavy and variable light sequences of the aligned intrabody sequences in FIG. 2.

FIG. 5 illustrates the flow cytometry data tabulated for the groups tested (control, PQ30, PQ103, PQ103+Happ1t and PQ103+INT41) ("Q30" and "Q103" disclosed as SEQ ID NOS 33 and 34, respectively) measured by GFP fluores-cence.

FIG. 6 discloses "Q103" as SEQ ID NO: 34.

FIG. 9 discloses "Q23" and "Q73" as SEQ ID NOS 39 and 35, respectively.

FIG. 11 demonstrates that when lysates from HttQ73 ("Q73" disclosed as SEQ ID NO: 35) induced cells (right columns) are passed through an immo-bilized-INT41 affinity column, only smaller fragments of degraded Htt are bound (fractions probed with rabbit anti-N-terminal Htt antibody) and uninduced HttQ73 ("Q73" disclosed as SEQ ID NO: 35) cells (left columns (days 8, 9, 10, 11) do not bind any detectable proteins in fractions probed on the same blot.

FIG. 12 shows the Human Tau protein sequence (SEQ ID NO: 40), including 9 splice variants. INT41 epitopes are highlighted in bold and peptides associated with exosomes are outlined in boxes.

FIG. 13A and FIG. 13B illustrate the mean body weights (±S.E.M.) of R6/2_WT and R6/2_Tg mice following treat-ment with rAAV6-GFP, rAAV6-Happ1t, rAAV6-INT41, or VEH (vehicle) from 4-12 weeks of age (open circle: vehicle in R6/2 WT controls; black square: rAAV-GFP in R6/2 Tg; gray square: rAAV-Happ1t in R6/2 Tg; open square: rAAV-INT41 in R6/2 Tg).

FIG. 16 shows non-normalized hind limb grip strength in mice treated with INT41, Happ1t, GFP or vehicle (control). The effects of rAAV6-INT41, rAAV6-Happ1t or rAAV6-GFP on the hindlimb grip strength of R6/2_Tg mice are shown as compared to VEH-treated R6/2_WT mice. Data are presented for females (panel A) and males (panel B) separately.

DETAILED DESCRIPTION OF THE INVENTION

Definitions

Figure 1A:
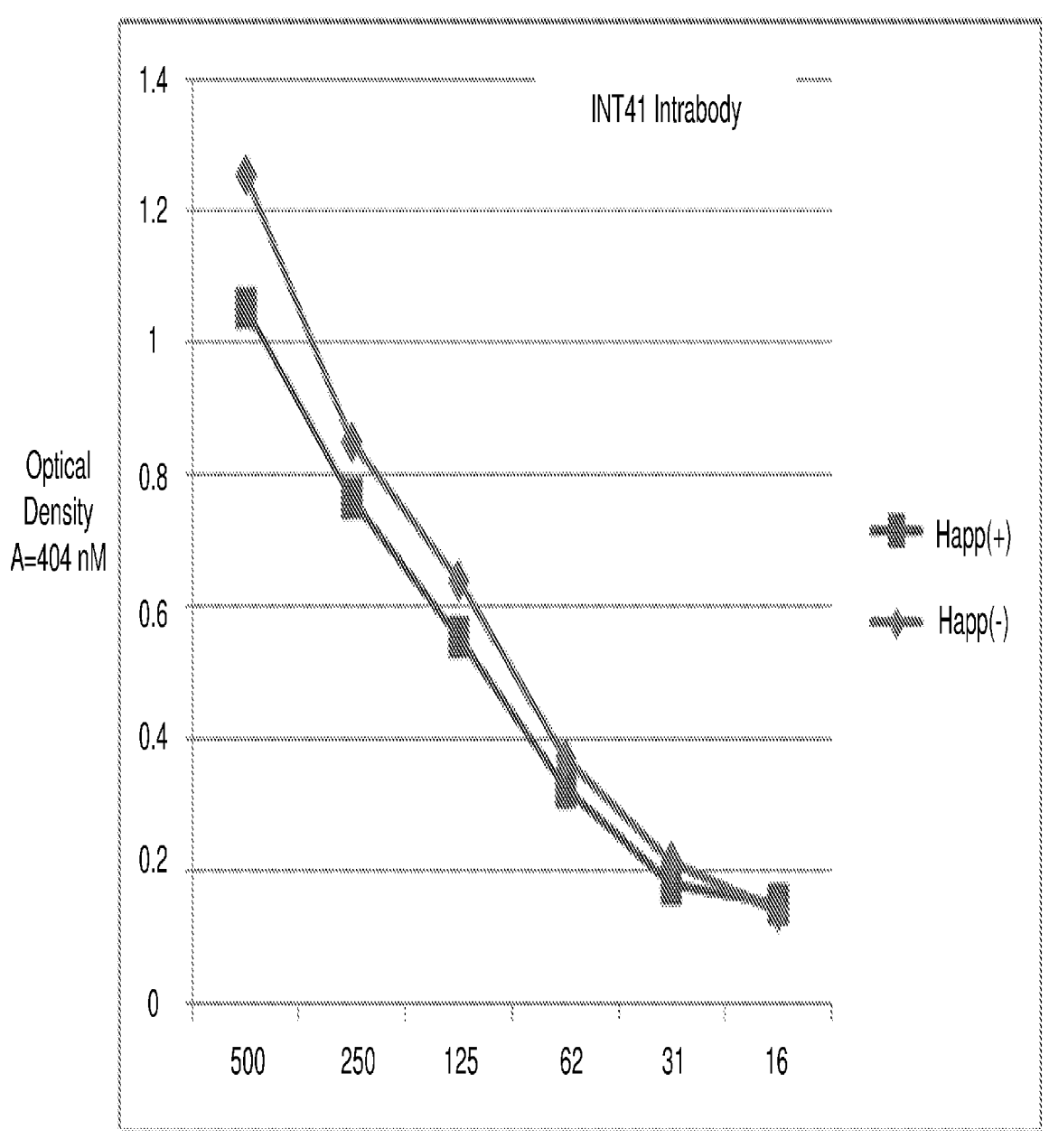
FIG. 1A, FIG. 1B, FIG. 1C, and FIG. 1D illustrate the binding of selected intrabodies to poly-proline peptides. The vertical axis is expressed as OD units at A=404 nM, and the horizontal axis is the concentration (nM) of purified intrabody.

Terms used in the claims and specification are defined as set forth below unless otherwise specified.

The term "ameliorating" refers to any therapeutically beneficial result in the treatment of a disease state, e.g., a disease state associated with Huntington's disease, including prophylaxis, lessening in the severity or progression, remis-sion, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity" in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can be a "prophylactically effective amount" as prophylaxis can be considered therapy.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

It must be noted that, as used in the specification and the appended claims, the singular forms "a," "an" and "the" include plural referents unless the context clearly dictates otherwise.

Intrabodies

An "intrabody" refers to an antibody that binds an intracellular protein. Intrabodies are modified to remain and function inside the cell (intracellular localization). Examples of modifications include a single-chain antibody (single-chain variable fragment, or scFv), modification of immunoglobulin variable light (VL) or heavy (VH) domains for hyperstability, or selection of antibodies resistant to the more reducing intracellular environment. An intrabody comprises a variable heavy sequence, a linker sequence and a variable light sequence.

A "single-chain variable fragment" (scFv) is a fusion protein of the variable regions of the heavy (VH) and light chains (VL) of immunoglobulins, connected with a short linker peptide. The linker peptide can be about ten to 25 amino acids in length. Although the two domains of the Fv fragment, VL and VH, are coded for by separate genes, they can be joined, using recombinant methods, by a synthetic linker that enables them to be made as a single protein chain in which the VL and VH regions pair to form monovalent molecules. See e.g., Bird et al., Science 242: 423-426, 1988; and Huston et al., Proc. Natl. Acad. Sci. USA, 85: 5879-5883, 1988. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. In some embodiments, the scFV is selected from a large library of randomly generated scFv proteins and not engineered. Single-chain variable fragments lack the constant Fc region found in complete antibody molecules and the common binding sites used to purify proteins. Single-chain variable fragments can be produced in bacterial cell cultures, such as E. coli. The scFvs can be purified can be purified using traditional chromatography or purified by binding to immobilized using Protein L (which interacts with the variable region of kappa light chains). The scFvs can also be purified by a six-histidine tag (SEQ ID NO: 38) incorporated at the C-terminus or a Strep II tag at the C or N-terminus of the scFv molecule.

Methods of the Invention

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Generating Peptide Sequences

Peptide sequences can be synthesized or generated using a wide variety of techniques known in the art. Peptides can be synthesized as peptides in solution or on a solid support in accordance with conventional techniques. Various automatic synthesizers are commercially available and can be used in accordance with known protocols. See Stewart and Young (supra); Tam et al., J Am Chem Soc, 105:6442, (1983); Merrifield, Science 232:341-347 (1986); Barany and Merrifield, The Peptides, Gross and Meienhofer, eds, Academic Press, New York, 1-284; Barany et al., Int J Pep Protein Res, 30:705-739 (1987).

Solid phase peptide synthesis methods can use a copoly (styrene-divinylbenzene) containing 0.1-1.0 mM amines/g polymer. These methods for peptide synthesis use butyloxy-carbonyl (t-BOC) or 9-fluorenylmethyloxy-carbonyl (FMOC) protection of alpha-amino groups. Both methods involve stepwise syntheses whereby a single amino acid is added at each step starting from the C-terminus of the peptide. Coligan et al., Curr Prot Immunol, Wiley Interscience, 1991, Unit 9. On completion of chemical synthesis, the synthetic peptide can be deprotected to remove the t-BOC or FMOC amino acid blocking groups and cleaved from the polymer by treatment with acid at reduced temperature (e.g., liquid HF-10% anisole for about 0.25 to about 1 hour at 0° C.). After evaporation of the reagents, the peptides are extracted from the polymer with 1% acetic acid solution that is then lyophilized to yield the crude material. This can normally be purified by such techniques as gel filtration on Sephadex G-15 using 5% acetic acid as a solvent. Lyophilization of appropriate fractions of the column will yield the homogeneous peptides or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

In other embodiments, phage display techniques can be used for identifying peptides. A phage library can be prepared (using e.g., lambda phage), displaying inserts of amino acid residues. The inserts can represent, for example, a completely degenerate or biased array. Phage-bearing inserts that bind to the desired antigen can be selected, and this process is repeated through several cycles of reselection of phage that bind to the desired antigen. DNA sequencing can be conducted to identify the sequences of the expressed peptides. The minimal linear portion of the sequence that binds to the desired antigen can be determined in this way. The procedure can be repeated using a biased library containing inserts containing part or all of the minimal linear portion plus one or more additional degenerate residues upstream or downstream thereof.

In another embodiment, ProCode technology including Membrane Anchored Display target trapping (MAD-Trap) and Functional Ligand Induced target trapping (FLI-Trap) can be used to select binding scFv peptides. See PCT/

US2011/028977 and PCT/US2006/032810, each incorporated by reference in its entirety.

These techniques can be used to prepare poly-proline peptide sequences, such as those described herein: (i) proline rich peptide used by Southwell [7, 8] (PQLPQPPPQAQP) (SEQ ID NO: 17) and (ii) carboxy derived Huntington's peptide (PGPAVAEEPLHRP) (SEQ ID NO: 18).

Vectors

Recombinant Viral Vectors: A viral vector capable of accepting the coding sequences for the nucleic acid molecule(s) to be expressed can be used in the methods described herein. For example vectors derived from adenovirus (AV); adeno-associated virus (AAV); retroviruses (e.g., lentiviruses (LV), Rhabdoviruses, murine leukemia virus); herpes virus, and the like can be used.

Selection of recombinant viral vectors suitable for use in the invention, methods for inserting nucleic acid sequences for expressing the intrabody sequences into the vector, and methods of delivering the viral vector to the cells of interest are within the skill in the art. See Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406.

Viral vectors can include those derived from AV and AAV. Suitable AAV vectors for expressing the intrabody sequences of the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Intrabody Generation and Selection

In some embodiments, intrabodies are generated that specifically inhibit an intracellular HttpQ protein or a protein comprising a polyQ sequence. Intrabodies can be created that bind to a proline rich peptide or a peptide sequence derived from a Huntingtin protein. In other embodiments, the intrabody can be selected to bind to an intracellular protein of any organism. Notably, because of the degree of evolutionary conservation of functional proteins, enzymes, protein-protein interactions, and signal transduction pathways, even though the intrabody will preferably be specific for a protein in a cell, it can also be expected that the intrabody will inhibit a homologous protein in a related species.

scFvs commonly exhibit poor stability and solubility when expressed in the cytoplasm. Techniques have been developed to overcome these difficulties associated with stable expression of intrabodies. Some strategies are as follows: modifying the cytoplasmic redox potential of the host strain by mutating components of the thioredoxin and glutaredoxin pathways; performing rounds of mutation and selection to identify scFv sequences that fold efficiently in an intracellular compartment; and using C-terminal fusions to a mature portion of E. coli maltose binding protein to stabilize scFvs expressed in the bacterial and mammalian cytoplasm. In another embodiment, a modified yeast 2-hybrid approach can be used, where a selectable marker is fused to a target scFv as an antigen-independent reporter of solubility.

In an embodiment, a selection assay by Fisher et al. is used to engineer intrabodies based on the intrinsic protein folding quality control mechanism of the bacterial twin-arginine translocation (Tat) pathway. See Fisher et al. Efficient isolation of soluble intracellular single-chain antibodies using the twin-arginine translocation machinery (Fisher, et al, J Mol Biol, 2009. 385(1): p. 299-311). The selection assay employs a tripartite sandwich fusion of a protein of interest (POI) with an N-terminal Tat-specific signal peptide (ssTorA) and C-terminal TEM1 β-lactamase (Bla), thereby coupling antibiotic resistance with Tat pathway export. The assay was adapted to develop the intrabody selection after Tat export assay (ISELATE), a high-throughput selection strategy for facile identification of solubility-enhanced scFv sequences. This approach is meant to improve substrate solubility, folding rate, and surface hydrophilicity results in enhanced export by the Tat pathway. ISELATE provides a method for selecting clones with greatly enhanced Tat export efficiency.

A synthesized library of randomized scFv13 variants can be used as described in Fisher et al. Amino acid sequence diversity can be introduced into the CDR3H and CDR3L chains of scFvT3 by randomizing library oligonucleotide DNA. The synthetic library can be amplified using PCR primers. The synthetic library can be cloned into cells, such as PC314, to eliminate scFv truncated variants and variants that are not expressed. The scFv expressing cells can be pooled, and the library is cloned into a vector (e.g., pSALect display vector (NdeI/NotI)).

In some embodiments, spheroblasts are generated that display the scFv library. For example, wild-type E. coli cells expressing the scFv library can be used and grown. Expression of the scFv from plasmids can be induced. For example, scFvs from pSALect-based plasmids can be induced with isopropyl β-D-1-thiogalactopyranoside. The spheroplasts are grown in culture and collected.

In an embodiment, the generated scFV library is then analyzed to select for positive transformants that bind to a biotinylated peptide (e.g., a biotinylated Huntingtin peptide). In an embodiment, magnetic beads can be used and incubated with the spheroplasted scFv library and Huntintin peptide. Positive transformants are selected for plating and grown.

The invention provides intrabodies having binding characteristics that have been improved by direct mutation or methods of affinity maturation. Random mutagenesis can be used to introduce mutations into the coding sequences of intrabodies. Random mutations with low mutation frequency can be introduced in the coding sequence of intrabodies by error-prone PCR using the GeneMorph II Random Mutagenesis kit (Stratagene) according to the manufacturer's protocol using PCR primers. In other embodiments, methods used for modifying or increasing affinity and specificity of antibody binding sites consisting of two variable domains can be applied to intrabodies (See, e.g., Yang et al., J. Mol Biol. 254:392-403 (1995)). For example, libraries binding domains into which diversity has been introduced can be easily screened for desired binding characteristics using phage display. Alternatively, yeast surface display can be employed. Intrabodies can be modified or improved by mutating CDR residues and screening for desired characteristics. In another embodiment, individual amino acid residues or combinations of residues are randomized so that in a population of otherwise identical antigen binding sites, subsets of from two to twenty amino acids are found at particular positions. Alternatively, mutations can be induced over a range of residues by error prone PCR methods (See, e.g., Hawkins et al., J. Mol Biol. 226: 889-96 (1992)). In another example, a phage display vector containing a heavy or light chain variable region gene can be propagated in a mutator strain of E. coli (See, e.g., Low et al., J. Mol. Biol. 250: 359-68 (1996)). These methods of mutagenesis are illustrative of the many methods known to one of skill in the art.

Binding Assays

Binding of an intrabody to a poly-proline peptide sequence or poly-glutamate protein can be tested using various binding assays. For example, ELISA assays can be performed to determine the binding activity of isolated scFv clones against a biotinylated Huntingtin peptide.

Enzyme-linked immunosorbent assay (ELISA), or enzyme immunoassay (EIA), is a test that uses antibodies and color change to identify a substance. ELISA is a plate-based assay designed for detecting and quantifying substances such as peptides, proteins, antibodies and hormones. In an ELISA, an antigen must be immobilized to a solid surface and then complexed with an antibody that is linked to an enzyme. Detection is accomplished by assessing the conjugated enzyme activity via incubation with a substrate to produce a measureable product. The most crucial element of the detection strategy is a highly specific antibody-antigen interaction. ELISAs are typically performed in 96-well (or 384-well) polystyrene plates, which will passively bind antibodies and proteins.

Various other peptide binding assays known in the art may be used to test the binding of an intrabody to a peptide sequence or protein of interest.

Pharmaceutical Compositions of the Invention

Methods for treatment of poly-Q diseases, such as Huntington's disease, are also encompassed by the present invention. Said methods of the invention include administering a therapeutically effective amount of intrabody, such as INT41. The intrabodies of the invention can be formulated in pharmaceutical compositions. These compositions can comprise, in addition to one or more of the intrabodies, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

Whether it is an intrabody, peptide, or other pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated. In some embodiments, the composition is administered in animals by bilaterial intrastriatal injection. The composition may be administered in humans using Convection Enhanced Delivery (Convection-enhanced delivery of macromolecules in the brain. R H Bobo et al., PNAS 1994 vol. 91 no. 6 pgs 2076-2080 and Convection-Enhanced Delivery of AAV Vector in Parkinsonian Monkeys; In Vivo Detection of Gene Expression and Restoration of Dopaminergic Function Using Pro-drug Approach, K S Bankiewicz et al. Experimental Neurology 164, 2-14 (2000)).

Methods for Preventing Aggregation of Poly-Glutamate Protein in a Cell Using Intrabodies Methods are provided for preventing aggregation of a poly-glutamine (polyQ) protein in a cell. The method includes introducing into the cell an intrabody described herein, such as INT41, A2, H8 or E10. In some embodiments, introducing the intrabody into the cell can be performed by transfection. The cell is maintained for a time sufficient for the intrabody to bind to a polyQ protein, thereby preventing aggregation of polyQ proteins in the cell.

Methods are also provided for preventing gene dysregulation caused by aggregation of a poly-glutamine (polyQ) protein in a cell. The method includes introducing into said cell the intrabody described herein and maintaining the cell for a time sufficient for the intrabody to bind to the polyQ protein, thereby preventing gene dysregulation of one or more genes in the cell. Exemplary genes targeted for preventing dysregulation are listed in Table 8 of U.S. Provisional Application 61/871,288 filed on Aug. 28, 2013, which is incorporated by reference in its entirety. In some embodiments, the polyQ protein is a Huntingtin (HttpQ) protein.

Methods for Treating Diseases Caused by Aggregation of a Poly-Glutamate Protein

In one aspect, the invention relates in particular to the use of an intrabody or a pharmaceutical composition prepared therefrom for the treatment or prevention of cognitive or behavioral conditions associated with a poly-glutamate associated disease, such as Huntington's disease. An intrabody according to the invention or a pharmaceutical composition prepared therefrom can enhance the quality of life, particularly in a patient being treated with for Huntington's disease.

The invention furthermore also relates to the use of an intrabody or a pharmaceutical composition thereof for treating Huntington's disease, in combination with other pharmaceuticals and/or other therapeutic methods, e.g., with known pharmaceuticals and/or known therapeutic methods, such as, for example, those which are currently employed for treating Huntington's disease. For example, the use of an intrabody or a pharmaceutical composition thereof can be combined with conventional medications and treatments that lessen symptoms of movement and psychiatric disorders (e.g., Xenazine®, which provides temporary relief of chorea).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ *Ed.* (Plenum Press) Vols A and B (1992).

Example 1: Identification of Novel Intrabodies

Novel candidates were designed using an alanine replacement strategy in the Intrabody complementarity determining region (CDR) to identify critical amino acids and subsequent mutagenesis for affinity maturation. ProCode technology including Membrane Anchored Display target trapping (MAD-Trap) and Functional Ligand Induced target trapping (FLI-Trap) are the methods used to select binding scFv peptides. See PCT/US2011/028977 and PCT/US2006/032810, the disclosures of which are incorporated by reference in their entireties.

Known intrabodies, such as Happ1 and Happ1t, have difficulties with solubility and thus cannot be used effectively in therapeutics or treatments. Efforts to enhance solubility by mutagenesis were unsuccessful for Happ1 and Happ1t. New intrabodies were developed using a proline rich peptide described by Patterson et al. [12-15] as a capture source for binders, followed by ELISA binding assays, to initially characterize binders. INT41 and similar intrabodies were developed from naïve libraries of scFv sequences using technology initially developed in the DeLisa laboratory at Cornell University [16-19]. Binders were then tested in many of the same cell-based and animal models used by the Caltech group with Happ1 as a positive control. In animal studies performed by PsychoGenics, the leading provider of animal model testing in Huntington's, INT41 was found to be superior to Happ1t in its ability to show improvement in a number of motor function and cognitive tests. Pathology results demonstrated that INT41 reduced the formation of small aggregates, while Happ1t increased aggregation suggesting that the limited solubility of Happ1t may contribute to pathology at some point in disease progression. Provided below are example methods for identification of INT41 and selected intrabodies.

Peptide Synthesis:

Peptides were synthesized by a custom peptide synthesis service (Biomatic, Delaware). The following peptides were used: (i) proline rich peptide used by Southwell [13, 14] (PQLPQPPPQAQP, SEQ ID NO: 17) and (ii) carboxy derived Huntington's peptide (PGPAVAEEPLHRP, SEQ ID NO: 18). The peptides were generated with a carboxy terminal biotin to facilitate selection on Strepavidin coated beads and ELISA plates.

scFv Library (T3) Construction

The synthetic library design was based on the T3 framework [16]. Amino acid sequence diversity was introduced into the CDR3H and CDR3L chains of scFvT3 by randomizing library oligonucleotide DNA. CDR3H was engineered with an NNK length yielding 7, 10 or 13 amino acids. CDR3L was engineered with an NNK length of 5, 8 or 10 amino acids. The library (GeneArt) comprised 1.54×1011 molecules.

The synthetic library was amplified using PCR primers listed below:

| Primer | Sequence (5'-3') |
|--------|------------------|
| PC147 | GACCATGATTACGCCAAGCTTGGCTAGCCATATGTCTAG AATGGCAGAAGTTCAGCTGGT (SEQ ID NO: 19) |
| PC148 | ATCCAGTGATTTTTTTCTCGTCGACCTCGAGTGCGGCCG CACCCAGAACTGCCAGTTTGG (SEQ ID NO: 20) |

The synthetic library was cloned into PC314 (Xba1/Not1) to eliminate scFv truncated variants and variants that are not expressed. The scFv expressing cells were pooled and the library cloned into the pSALect display vector (NdeI/NotI).

Preparation of Spheroplasts

Wild-type E. coli (Lucigen E. cloni 10G) and E. coli cells expressing the T3 combinatorial scFv library were grown in 25 ml LB medium containing chloramphenicol (20 μg/mL) for 1.5 h at 37° C. Expression of scFvs from pSALect-based plasmids was induced with isopropyl β-D-1-thiogalactopyranoside (IPTG, 1.0 mM). Following induction, cell flasks were shifted to room temperature for overnight growth. The OD600 of each culture was measured and the volume corresponding to $1 \times 10^{10}$ cells added to a 1.5 ml microcentrifuge tube. Cell pellets were gently washed with 500 μL of ice-cold fractionation buffer (0.1 M Tris, 0.75 M sucrose, buffer pH 8.0) and resuspended in 350 μl, of ice-cold fractionation buffer supplemented with lysozyme (1 mg/mL). Cells were slowly vortexed, 700 μL of EDTA (1 mM, pH 8.0) was added dropwise, and tubes were incubated at room temperature for 20 min. After adding 50 μl of cold MgCl (0.5 M), tubes were incubated on ice for 10 min and then spun down (6000 rpm) for 10 min at 4° C. The supernatant was carefully removed, and the spheroplasts resuspended in 1 mL of ice-cold PBS.

Panning the T3 scFv Library

In one example, the generated scFV library was analyzed to select for positive transformants that bind to the biotinylated Huntingtin peptide. Pierce Streptavidin Magnetic Beads (25 μl, Thermo Scientific) were washed with phosphate buffered saline and mixed with 70 μl of E. coli wild-type spheroplasts to minimize non-specific binding of our T3 scFv library. Phosphate buffered saline (930 μl) was added to bring the volume in the microcentrifuge to 1 ml. The beads were incubated overnight with shaking at 4° C. The spheroplasted T3 scFv library (130 μl) was mixed with biotinylated Huntingtin peptide (RPQLPQPPPQAQPRGGGSK; SEQ ID NO:25) at a concentration of 4.5 μM, 45 μM and 100 μM. The volume in each microcentrifuge tube was brought up to 1 ml with PBS. The T3 spheroplasted scFv library was incubated with the Huntingtin peptide overnight with shaking at 4° C. (spheroplast:Ag complex). Following incubation at 4° C. overnight, the magnetic beads were captured, washed with 1 ml PBS and mixed with the spheroplast:Ag complex. The mixture was incubated for an additional 30 minutes at 4° C. The Ag:spheroplast complex was captured with magnetic force, washed with phosphate buffered saline containing 300 mM NaCl and 0.015% Tween and resuspended in 50 μl Elution Buffer (Quiagen). The sample was boiled at 95° C. for 5 minutes, cooled to 4° C. and subsequently dialyzed against H2O for 30 minutes. 100 ng of DNA was transformed into E. coli 10G Electrocompetent cells (Lucigen) for amplification. Cultures were incubated with shaking at 37° C. for 1 hour. Positive transformants were selected for by plating on LB agar containing chloramphenicol and growing overnight at 37° C.

Random Mutagenesis

Random mutagenesis was used to introduce mutations into the coding sequences of intrabodies. Random mutations with low mutation frequency were introduced in the coding sequence of intrabodies by error-prone PCR using the GeneMorph II Random Mutagenesis kit (Stratagene) according to the manufacturer's protocol using PCR primers:

| Primer | Sequence (5'-3') |
|--------|------------------|
| PC147 | GACCATGATTACGCCAAGCTTGGCTAGCCATATGTCTAG AATGGCAGAAGTTCAGCTGGT (SEQ ID NO: 19) |
| PC148 | ATCCAGTGATTTTTTTCTCGTCGACCTCGAGTGCGGCCG CACCCAGAACTGCCAGTTTGG (SEQ ID NO: 20) |

PCR conditions were chosen to obtain a mutation rate of 1-5 mutations per 1000 base pairs. The 4 PCR mixtures each consisted of 5 μL of 10× Mutazyme II reaction buffer, 1 μL of 40 mM mutagenic dNTP mix (200 μM each final), 0.5 μL of forward and reverse primer master mix (250 ng/μl of each primer), 1 μL of Mutazyme II DNA polymerase (2.5 U/μL), and 0.7 ng of intrabody template in a total volume of 50 μL. The amplified DNA was purified using a QIAquick PCR Purification Kit. The purified product was then digested with restriction enzymes NotI and NdeI and cloned into plasmid vector pSALect. Ligation was achieved by adding T4 DNA ligase to the PCR product and pSALect vector for 1 hr. The recombinant plasmids were each transformed into E. coli 10G Electrocompetent cells (Lucigen) for amplification. Cultures were incubated with shaking at 37° C. for 1 hour. Positive transformants were selected for by plating on LB agar containing chloramphenicol and growing overnight at 37° C. The following day, 5 ml LB medium was added to each plate, the cells were scraped off, and the intrabody mutagenesis clones pooled.

Cloning

Positive hits screened by ELISA (end-point dilution) were miniprepped, and plasmid DNA cut with NotI/NdeI. The ~0.75-kb NotI/NdeI DNA fragment was cloned into the multiple cloning site of pET 24a generating a C-terminus Strep-tag fusion construct. The recombinant vector was subsequently transformed into BL21(DE3) cells for protein expression analysis. For cell-based assays, the positive hits screened by ELISA were miniprepped and the plasmid DNA used as template in a PCR reaction. PCR primers PC147 (5'-GACCATGATTACGCCAAGCTTGGCTAGC-CATATGTCTAGAATGGCAGAAGTTCAG CTGGT-3')

(SEQ ID NO: 19) and PC148 (ATCCAGTGAT-TTTTTTCTCGTCGACCTCGAGTGCGGCCGCACCCA-GAACTGCCAG TTTGG) (SEQ ID NO:20) were used in the amplification reaction. The ~0.75-kb DNA fragment was purified using a QIAquick PCR Purification Kit, cut with NheI and Xho1 and ligated into the multiple cloning site of pOptiVEC. pOptiVEC was also used for all cell-based expression of scFvs which were PCR amplified from pSA-Lect and ligated into pOptiVEC at the NheI and Xho1 sites.
ELISA ELISA was performed to determine the binding activity of isolated scFv clones against biotinylated Huntingtin peptide designated Happ(+) (RPQLPQPPPQAQPRGGGSK-biotin (SEQ ID NO: 26), and a second biotinylated Huntingtin peptide designated Happ(−) (PGPAVAEEPLHRPG-biotin (SEQ ID NO: 28). All incubations except antigen coating were carried out at room temperature. Microtiter plates (Nuc) were coated with 100 µl of a biotinlyated Huntingtin peptide solution (2 µg/ml in 50 mM NaHCO3 buffer, pH 9.6) and incubated overnight at 4° C. The plates were washed 3 times with 200 µl of 1×TBS (50 mM Tris-Cl, 150 mM NaCl pH 8.0) and blocked with 100 µl of 2% milk in TBS for 2 hr. Plates were washed once with 200 µl of 1×TBS. In some experiments, preblocked Strepavidin coated plates (Pierce) were used to bind biotinylated peptide. Cell extracts (50 µl) or purified StrepII tagged Intrabodies were added to the antigen-coated blocked plates and incubated for 1.5 hr. Extracts of *E. coli* cultures from individual colonies selected by panning after overnight induction with IPTG were prepared by lysis in B-Per (Pierce) as described by the manufacturer and centrifuged at 10,000×g for 10 minutes to remove cell wall and debris. Supernatants from these extracts were used directly or diluted with TBS (1:2, 1:4) prior to use. Plates were washed 5× with 200 µl of 1×TBST (50 mM Tris-Cl, 150 mM NaCl, Tween 20 pH 8.0). Next, 100 µl of horseradish peroxidase (HRP)-conjugated anti-FLAG-tagged (Sigma) antibody was added and incubated for 1.5 hr. The plate was washed 5× with 200 µl of 1×TBST and 1× with 200 µl of 1×TBS. After washing, 100 µl of 3,3',5,5'-tetramethylbenzidine (TMB) was added. The peroxidase reaction was stopped after an appropriate time by the addition of 100 µl of 2M H2SO4. The optical density (OD) was measured at 405 nm on a spectrophotometer and the level of scFv binding determined.
Cell-Based Expression Conditions for transfection and punta formation were first optimized by running a matrix varying vector and cell concentrations for Htt-exon-1-GFP and intrabodies. 293T cells were cultured in DMEM+10% Fetal Bovine Serum. The day before transfection, plate $1.2×10^5$ cells in 500 µL of growth medium in 24 well plate without antibiotics so that cells will be ~60% confluent at the time of transfection. Transfection medium used was Opti-MEM and Lipo-factamine2000 (Invitrogen) was used to introduce DNA into cells. For analysis by flow cytometry cells were release by treatment with 0.05% Trypsin/EDTA followed by dilution into Opti-MEM in 10% serum then washed in the same medium by centrifugation 3 times.

For each transfection sample, the following steps were performed:
 a. Diluted 0.2 µg pQ103 ("Q103" disclosed as SEQ ID NO: 34) DNA with/without 0.8 ug scFv DNA in 50 µL of Opti-MEM, mix gently.
 b. Mixed 2 µl Lipofectamine in 50 µL of Opti-MEM, mix gently.

c. Incubated at room temperature for 5 minutes, combine DNA with Lipofectamine. Mix gently and incubate for additional 20-30 minutes at room temperature.
 d. Added DNA/Lipofectamine complex to 293T cell, mix gently and incubate at 37° C. to ~40 hrs. (Culture can be moved to 32° C. after 16 hrs incubation at 37° C. to slow down growth and maintain monolayer).

Counting of the GFP punta was performed by microscopy and/or flow cytometry (Coulter Epics Analyzer) following harvest of 293T cells 24-40 hours following transfection.
Histopathology Brains from R6/2 mice as above were performed at 12 weeks as described below.

Perfusion Methods: Animals were anesthetized using Sodium Pentobarbital i.p. (100 mg/kg BW). Next, mice were transcardially perfused using a peristaltic pump and were perfused with 4% paraformaldehyde (PFA) in 0.1M PBS (pH=7.4) on ice. The brains were then removed from skull and post-fixed overnight at 4° C. The brains were then stored at 4° C. in 0.1M PBS containing 0.01% Sodium Azide until the time of shipment to NeuroScience Associates.

Sections were prepared by Neuroscience Associates (Knoxville, TN) using MultiBrain® technology. Twenty five (25) Mouse Brains were embedded together per block, freeze-sectioned at 35 in the coronal plane through the entire mouse brain (~12 mm in length). All cut sections were collected into an antigen preservation solution. Immunohistochemistry was performed with the EM-48 monoclonal antibody to reveal HTT aggregates for every sixth section, at 210 µm intervals, yielding ~57 slides per block (~57 stained sections per Mouse Brain, ~2850 stained sections total).

Example 2: Identification of INT41 Intrabody

Intrabodies were selected using MAB-Trap as described [18] using the poly-proline peptide PRP.

Following an initial round of selection, scFvs were selected as described on Strepavidin coated beads following incubation with spheroplasts using two rounds of selection at 4.5 µM, 45 µM, 100 µM of biotinlyated peptide at 40° C. overnight. Four positive hits were then subjected to random PCR mutagenesis. Following another round of selection and enrichment using 0.5 µM biotinylated peptide at 40° C. for 1 hour, a final group four scFvs (INT41 (SEQ ID NO:1), A2 (SEQ ID NO:2), E10 (SEQ ID NO:3) and H8 (SEQ ID NO:4)) were selected based on ELISA results.

A group of final selected scFvs were PCR cloned with a 3'(carboxy terminal) StrepII tag into pET24 vector and transformed into *E. coli*. *E. coli* clones were selected on antibiotic, sequenced to verify insert and up to 1 L cultures were prepared and induced at approximately 0.2 OD 600 with IPTG and continued in shaking culture (300 rpm) overnight before harvest at from 10-20 OD 600. Pelleted cells were microfluidized (M110Y, Microfluidics Corporation) following dilution of 10-20× by volume into TBS 5 mM EDTA before clarification at 10,000×G by centrifugation, then purified on a StrepTactin Sepharose High Performance Column (GE Life Sciences). The column was washed and eluted as described by the manufacturer.

Purified scFvs were screened by ELISA with both biotinylated PRP (RPQLPQPPPQAQPRGGGSK-biotin; SEQ ID NO: 26) and a second biotinylated proline rich peptide derived from a downstream sequence from the Huntingtin protein (PGPAVAEEPLHRPG-biotin; SEQ ID NO: 28). Happ(+) is the peptide sequence PQLPQPPPQAQP (SEQ ID NO: 17). Happ(−) is the peptide sequence PGPAVAEE-PLHRP (SEQ ID NO: 18). Happ(+) and Happ(−) were derived from the Huntingtin exon1 protein sequence. The Huntingtin exon 1 protein includes the following sequences for a N terminal region (MATLEKLMKAFESLKSFQQQQ (Q)n) (SEQ ID NO: 29), a poly-proline region (PPPPPPPPPPPQLPQPPPQAQPLLPQPQ (underline is Happ(+)) (SEQ ID NO: 30), and a C terminal P-rich region (PPPPPPPPPPGPAVAEEPLHRPK (underline is Happ(–)); SEQ ID NO: 31). The Happ(+) and Happ(–) peptides were used in an ELISA binding assay with intrabodies INT41, A2, H8 and E10.

Both poly-proline peptides were specifically and equally recognized by all scFvs including the Happ1t scFv [13-15], suggesting that the specificity lies in the common recognition of primarily a proline sequence PGP (Happ(–)) or PQP (Happ (+)) that introduces structure disruption into sequences [20] separated by any single amino acid. This PXP sequence is a common recognition element of proline-rich regions which plays a significant role in intracellular signaling [21]. The Happ1t protein is predominately found in the inclusion bodies, but refolding was not successful and it could only be assayed in lysate form where adequate solubility could be maintained.

Figure 1B:
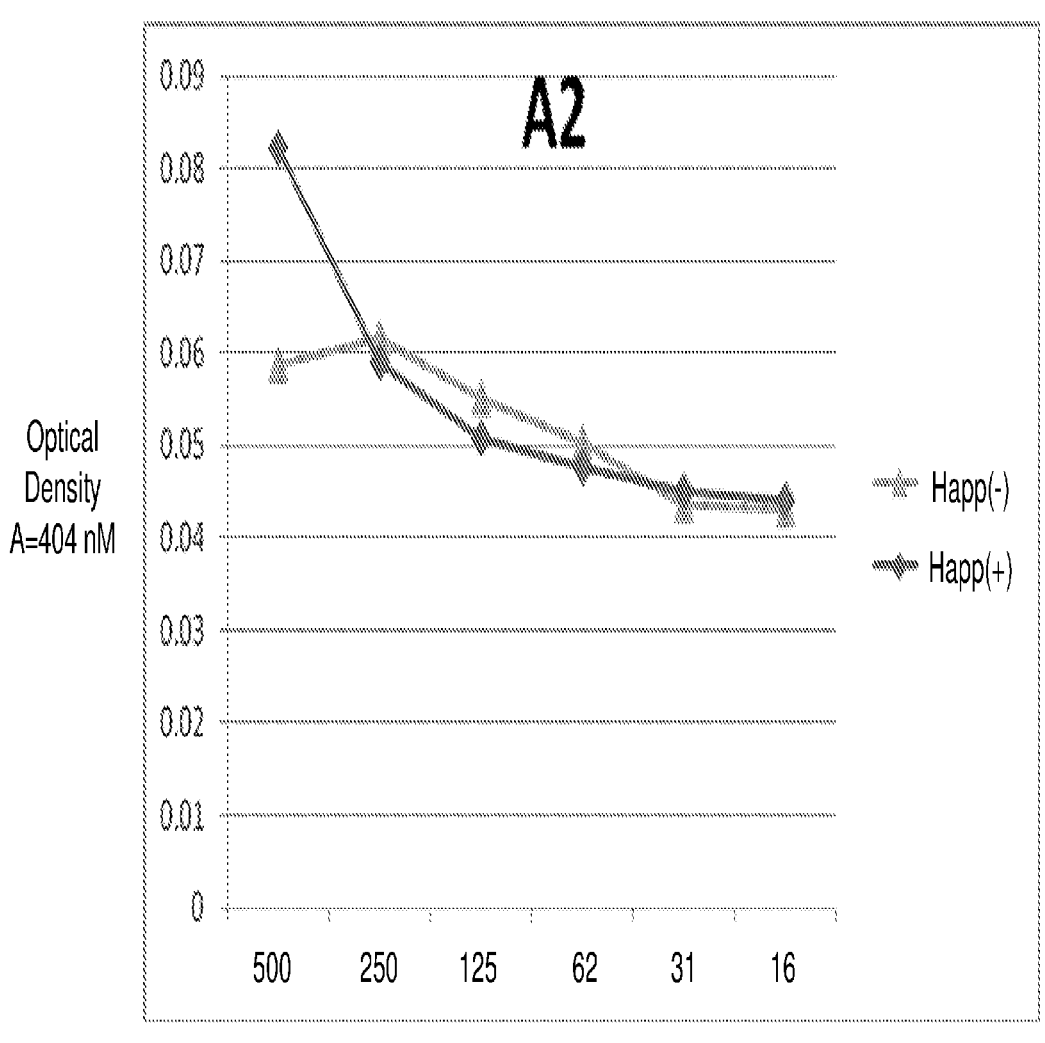
Figure 1C:
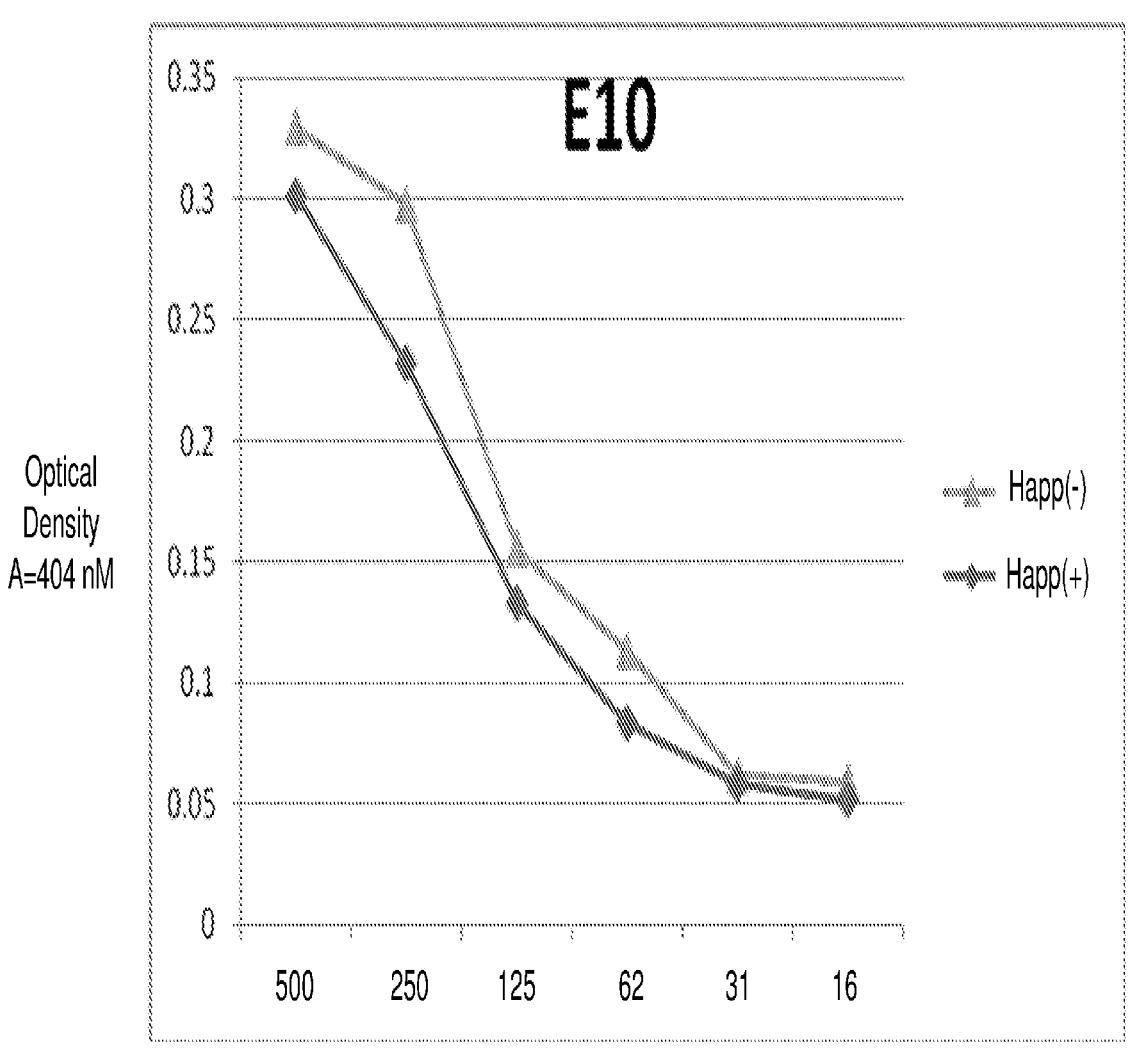
Figure 1D:
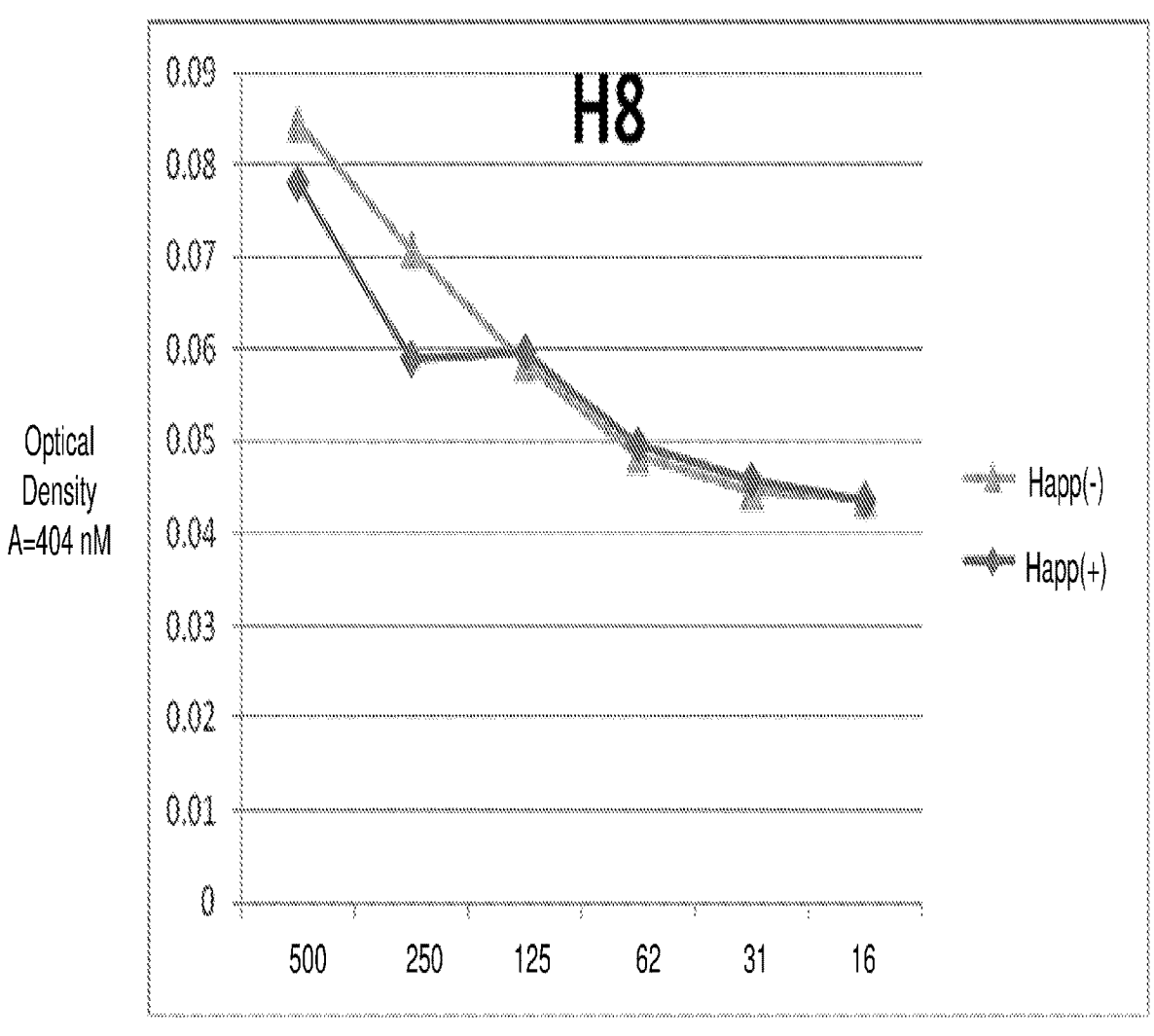

In FIGS. 1A-1D, the binding of the selected intrabodies to the poly-proline peptides are shown. The vertical axis is expressed as OD units at A=404 nM and the horizontal axis is the concentration (nM) of purified intrabody. FIG. 1A shows binding for INT41 (SEQ ID NO: 1). FIG. 1B shows binding for A2 (SEQ ID NO: 2). FIG. 1C shows binding for E10 (SEQ ID NO: 3). FIG. 1d shows binding for H8 (SEQ ID NO: 4). INT41 was the strongest binder, showing higher optical density units at higher intrabody concentration.

Although H8 was only weakly positive in binding when purified, it demonstrated three times the signal when assayed in lysate form, even though it was expressed at approximately the same levels as INT41. H8 recovery in the purified format was comparatively low. H8 may be unstable in purified form and could aggregate resulting in lower signal. This may explain its ability to block in the cell-based assay where intracellular concentrations of all the intrabodies tested are comparable.

The selected intrabodies were sequenced and shown in the Table 1.

TABLE 1

| SEQ ID NO | SEQUENCE | NAME |
|---|---|---|
| 1 | MAEVQLVVSGGGLVKPGGSMILSCAASGFTFSNYSMNW VRQAPGKGLEWVSSISSSSEYIYYADFVKGRFTISRDN AKNSLYLQMDSLRAEDTAVYYCAWPGYRKAWGRGTLVT VSSGGGGSGGGGSGGGGSQSVLTQPASVSGSPGQSITI SCAGTSSDVGGYNYVSWYQQHPGKAPKLMIYEDSKRPS GVSNRFSGSKSGNTASLTISGLRAEDEADYYCSYCASK GHWLFGGGTKLAVLGAAAEQKLIS | INT41 |
| 2 | MAEVQLVVSGGGLVKPGGSMILSCAASGFTFSNYSMNW VRQAPGKGLEWVSSISSSSEYIYYADFVKGRFTISRDN AKNSLYLQMDSLRAEDTAVYYCAHWPRLWRFPLWGRGT LVTVSSGGGGSGGGGSGGGGSQSVLTQPASVSGSPGQS ITISCAGTSSDVGGYNYVSWYQQHPGKAPKLMIYEDSK RPSGVSNRFSGSKSGNTASLTISGLRAEDEADYYCVLN MHWANFGGGTKLAVLGAAAEQKLIS | A2 |
| 3 | MAEVQLVVSGGGLVKPGGSMILSCAASGFTFSNYSMNW VRQAPGKGLEWVSSISSSSEYIYYADFVKGRFTISRDN AKNSLYLQMDSLRAEDTAVYYCAITGCECTWGRGTLVT VSSGGGGSGGGGSGGGGSQSVLTQPASVSGSPGQSITI SCAGTSSDVGGYNYVSWYQQHPGKAPKLMIYEDSKRPS GVSNRFSGSKSGNTASLTISGLRAEDEADYYCSCIRGL | E10 |

TABLE 1-continued

| SEQ ID NO | SEQUENCE | NAME |
|---|---|---|
| | KAAYFGGGTKLAVLGAAAEQKLIS | |
| 4 | MAEVQLVVSGGGLVKPGGSMILSCAASGFTFSNYSMNW VRQAPGKGLEWVSSISSSSEYIYYADFVKGRFTISRDN AKNSLYLQMDSLRAEDTAVYYCAAAVCNGRPDTWGRGT LVTVSSGGGGSGGGGSGGGGSQSVLTQPASVSGSPGQS ITISCAGTSSDVGGYNYVSWYQQHPGKAPKLMIYEDSK RPSGVSNRFSGSKSGNTASLTISGLRAEDEADYYCGYS LLPVLFGGGTKLAVLGAAAEQKLIS | H8 |

FIG. 2 shows the sequences of the selected scFvs aligned using LaserGene to determine critical and consensus amino acids. A consensus sequence (SEQ ID NO: 5) is shown aligned with INT41 (SEQ ID NO: 1), A2 (SEQ ID NO: 2), E10 (SEQ ID NO: 3) and H8 (SEQ ID NO: 4).

FIG. 2 also shows the CDR1, CDR2, and CDR3 regions within the intrabody sequences. In FIG. 3, the variable heavy and variable light sequences of the intrabodies are shown. For the aligned sequences, the Variable Heavy CDR1 sequence is at positions 8-12, Variable Heavy CDR2 sequence is at positions 50-58, Variable Heavy CDR3 sequence is at positions 100-110. The Variable Light CDR1 sequence is at positions 158-167, Variable Light CDR2 sequence is at positions 185-190, and the Variable Light CDR3 sequence is at positions 225-235. The linker sequence is at positions 119-137 (SSGGGGSGGGGSGGGGS) (SEQ ID NO: 16).

Example 3: Intrabodies Prevent Aggregation of HttpQ Protein

In certain embodiments, the effect of the intrabodies on HttpQ protein aggregation was tested.

DNA vectors containing HttpQ were fused with green fluorescent protein (GFP) and introduced into cells by transfection with or without nucleic acid molecules encoding the selected intrabodies [8]. Aggregation of the HttpQ protein was observed by fluorescent microscopy and flow cytometry.

Figure 4:
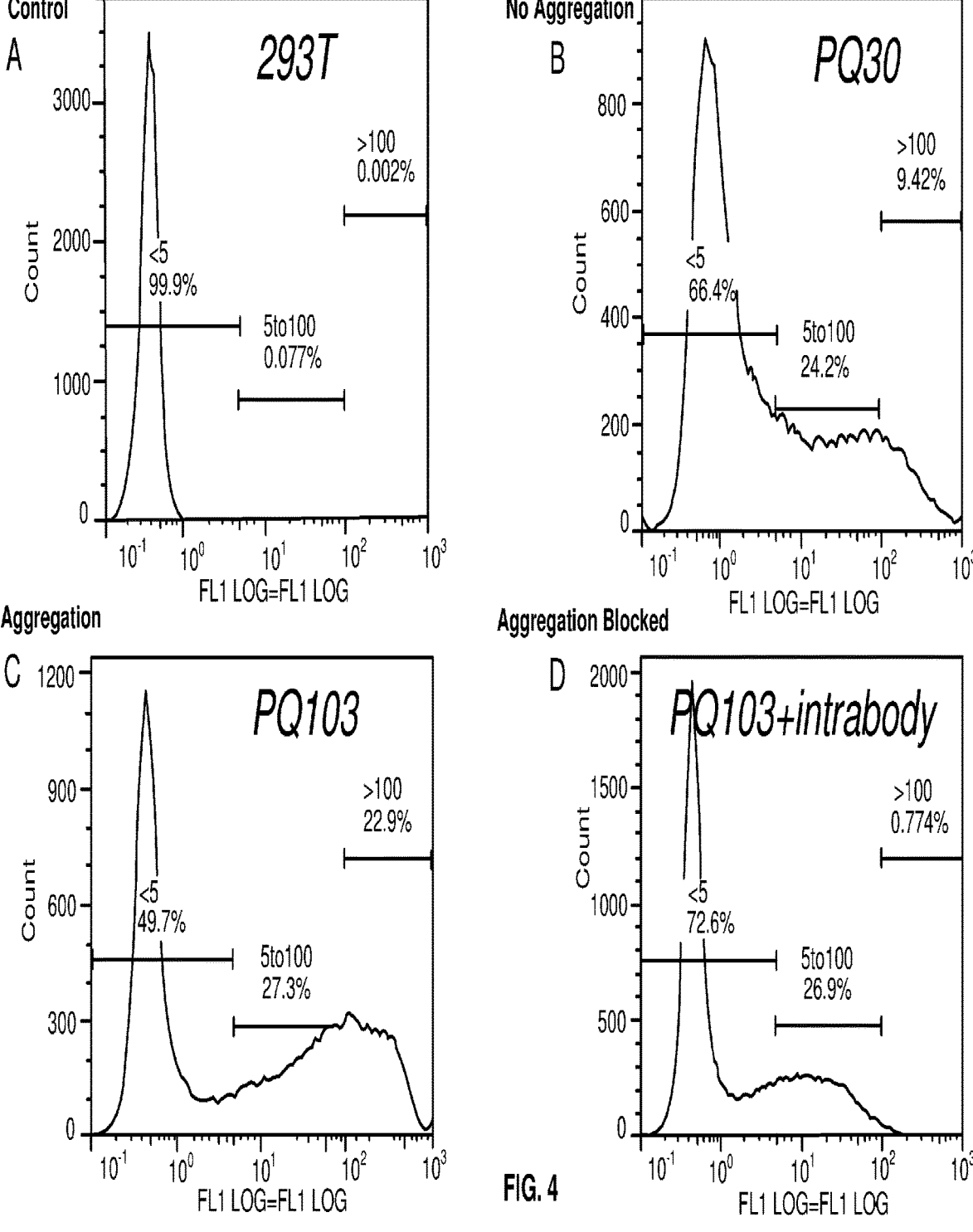
FIG. 4 shows flow cytometry graphs of INT41 and similar PRP specific intrabodies shows inhibition of HttpQ aggre-gation (a control group of non-transfected 293T cells (293T); 293T cells transfected with a non-aggregating HttpQ30-GFP (PQ30) ("Q30" disclosed as SEQ ID NO: 33); 293T cells transfected with aggregating HttpQ103-GFP (PQ103) ("Q103" disclosed as SEQ ID NO: 34); and 293T cells transfected with aggregating HttpQ103-GFP (PQ103) ("Q103" disclosed as SEQ ID NO: 34) and Intrabody (INT41).

In flow cytometry, better quantification was achieved through the analysis of tens of thousands of cells in minutes. In FIG. 4, flow cytometry analysis of INT41 and similar PRP specific intrabodies shows inhibition of HttpQ aggregation. The number of cells was plotted on the Y axis and the log fluorescence on the X axis. In a control group, 293T cells (FIG. 4A) were not transfected. In the absence of HttpQ-GFP (Control, 293T) fluorescence is not observed ($<10^0$). A non-aggregating HttpQ30-GFP (PQ30) ("Q30" disclosed as SEQ ID NO: 33) shows fluorescence mostly in the first and second decade of the fluorescence scale. In FIG. 4C, the aggregating HttpQ103-GFP (PQ103) ("Q103" disclosed as SEQ ID NO: 34) shows a dramatic and significant shift to the highest decade of fluorescence. Separate cultures of 293T cells were transfected with 1-4 µg of a PQ30-GFP ("Q30" disclosed as SEQ ID NO: 33) (FIG. 4B) or transfected with a PQ103-GFP-containing lentiviral vector ("Q103" disclosed as SEQ ID NO: 34) (FIG. 4C) [8]. PQ103 ("Q103" disclosed as SEQ ID NO: 34)+Intrabody (FIG. 4D) received PQ103-GFP ("Q103" disclosed as SEQ ID NO: 34) plus 1-4 µg of Happ1t cDNA cloned into the OptiVec vector (Life Sciences, Carlsbad CA) under control of the CMV promoter. Fluorescence was monitored on a Coulter FACS Scan. Flow cytometry assay was performed, and PRR specific intrabodies reduced the fluorescence in the third decade by up to 20 fold and demonstrated a dramatic decrease in fluorescence signal between that of untransfected controls and PQ30-GFP ("Q30" disclosed as SEQ ID NO: 33). These experiments were repeated six times due to variation in transfection efficiency. FIG. 5 shows the results tabulated for the groups tested (control, PQ30, PQ103, PQ103+Happ1t and PQ103+INT41) ("Q30" and "Q103" disclosed as SEQ ID NOS 33 and 34, respectively). Samples 5 and 6 are two variants of E10, one of which has a single amino acids change in a nonbinding framework region.

In fluorescence microscopy experiments, HttpQ30 ("Q30" disclosed as SEQ ID NO: 33) showed diffuse cytoplasmic staining characteristic of protein distribution throughout the cytoplasm, while HttpQ103 ("Q103" disclosed as SEQ ID NO: 34) demonstrated punctate staining or bright spots of fluorescence in the cytoplasm indicative of aggregation which were inhibited in the presence of INT41 (data not shown). When Happ1t, INT41 and other intrabodies targeting the same sequence as Happ1t were co-expressed with HttpQ103-GFP ("Q103" disclosed as SEQ ID NO: 34), fluorescence in the highest decade was dramatically reduced, as seen in FIG. 4 as a shift in fluorescence to an intermediate distribution between the 293T control and PQ30 ("Q30" disclosed as SEQ ID NO: 33) (PQ103+ Intrabody) ("Q103" disclosed as SEQ ID NO: 34).

Example 4: INT41 Prevents Gene Dysregulation

In another example, experiments were performed to test the effect of intrabodies on gene dysregulation.

In one example, mRNA was extracted from cells, and the levels of gene expression for 29,000 genes was measured (performed by Phalanx One Array). These data were analyzed on large microarrays for gene expression levels in the various samples. The data were analyzed using Integrity Systems software for disease association, pathway analysis, and similar features of intracellular networks. This analysis revealed that the gene expression patterns for HttpQ (PQ103) ("Q103" disclosed as SEQ ID NO: 34) are consistent with those from Huntington's animal models and samples from human neurons taken at autopsy. The data also demonstrated subsets of genes that are increased or decreased in expression level (data not shown).

Cells expressing PQ103 or PQ103+INT41 ("Q103" disclosed as SEQ ID NO: 34) were analyzed for over-expression or under-expression of selected genes. In samples taken from PQ103+INT41-expressing cells ("Q103" disclosed as SEQ ID NO: 34), both the over- and under-expression pattern changes caused by the PQ103 ("Q103" disclosed as SEQ ID NO: 34) aggregating phenotype were largely prevented for the genes most affected.

Examples of some of the genes with altered expression in Huntington's with altered expression is prevented by intrabodies of the invention are listed in Table 2 below, along with the fold expression changes. Other genes that are dysregulated in Huntington's and whose dysregulation is inhibited by intrabodies of the invention are involved in mitochondrial function, clathrin coated pit transport, membrane transport and other genes that lead to progressive neuron dysfunction and neuron death. An exemplary list of genes that were increased in expression 2× or decreased in expression 0.5× (649 genes) are also found in the Appendix (Table 8) of U.S. Provisional Application 61/871,288 filed on Aug. 28, 2013, which is incorporated by reference in its entirety. A total of 29,000 genes were tested. In an embodiment, the genes are tested with Rosetta Biosoftware that uses a proprietary proprietary system for calculating fold changes by incorporating weighed error. The calculations for the list of genes are shown in Table 8 of U.S. Provisional Application 61/871,288 filed on Aug. 28, 2013, which is incorporated by reference in its entirety.

Figure 6:
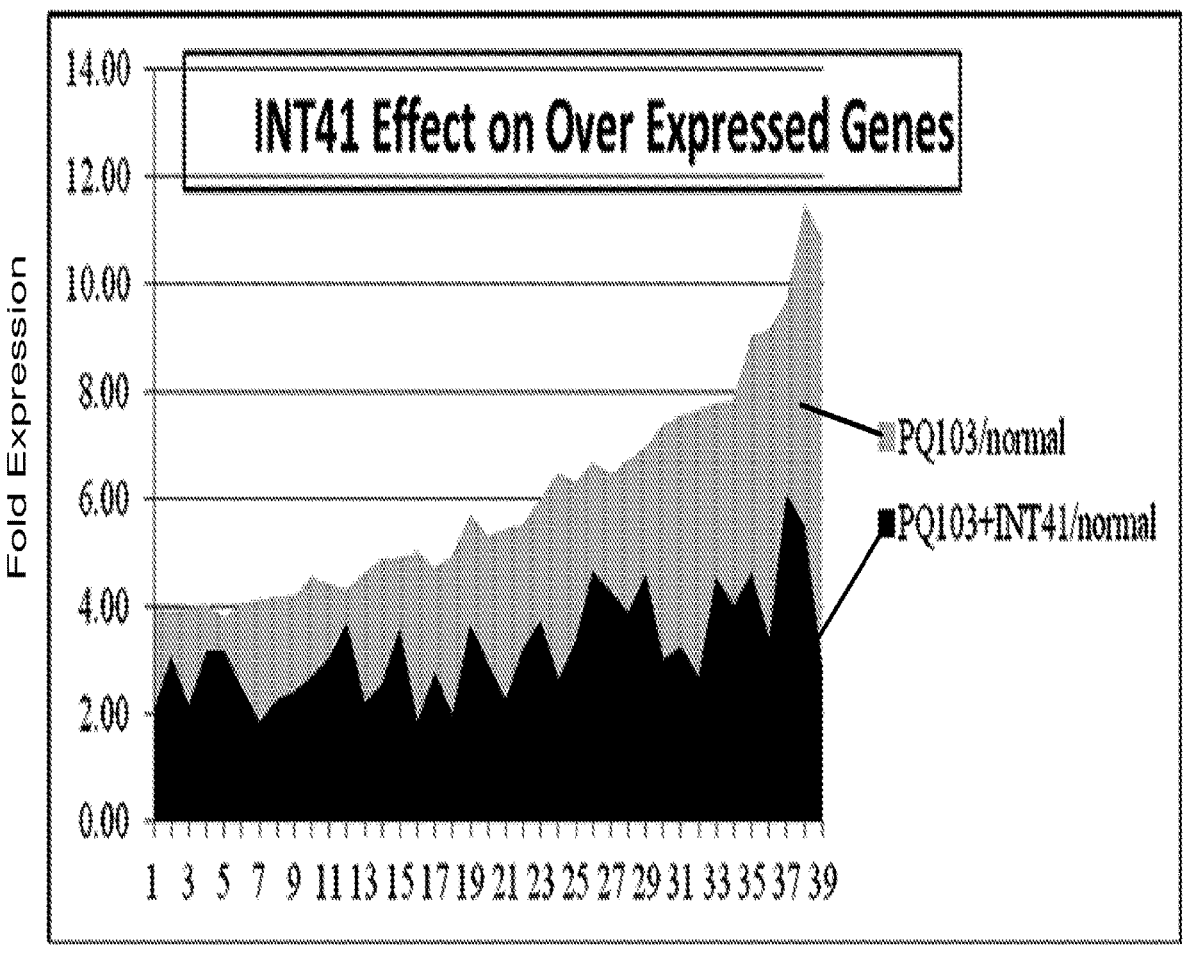
FIG. 6 shows the effect of INT41 on the expression of genes that exhibit over-expression caused by HttpQ.

In FIG. 6, INT41 was shown to inhibit the over-expression of genes caused by PQ103 ("Q103" disclosed as SEQ ID NO: 34). The reduction in the fold expression of representative over-expressed genes is shown between cells expressing PQ103 alone or PQ103 and INT41 ("Q103" disclosed as SEQ ID NO: 34). The mRNA was isolated from up to $2\times10^6$ cells and sent to Phalanx One Array Sciences for QC and microRNA using Kreatech™ labeling. The mRNA was probed against arrays of 29,000 genes in triplicate. The results were analyzed by Rosetta Resolver software.

Figure 7:
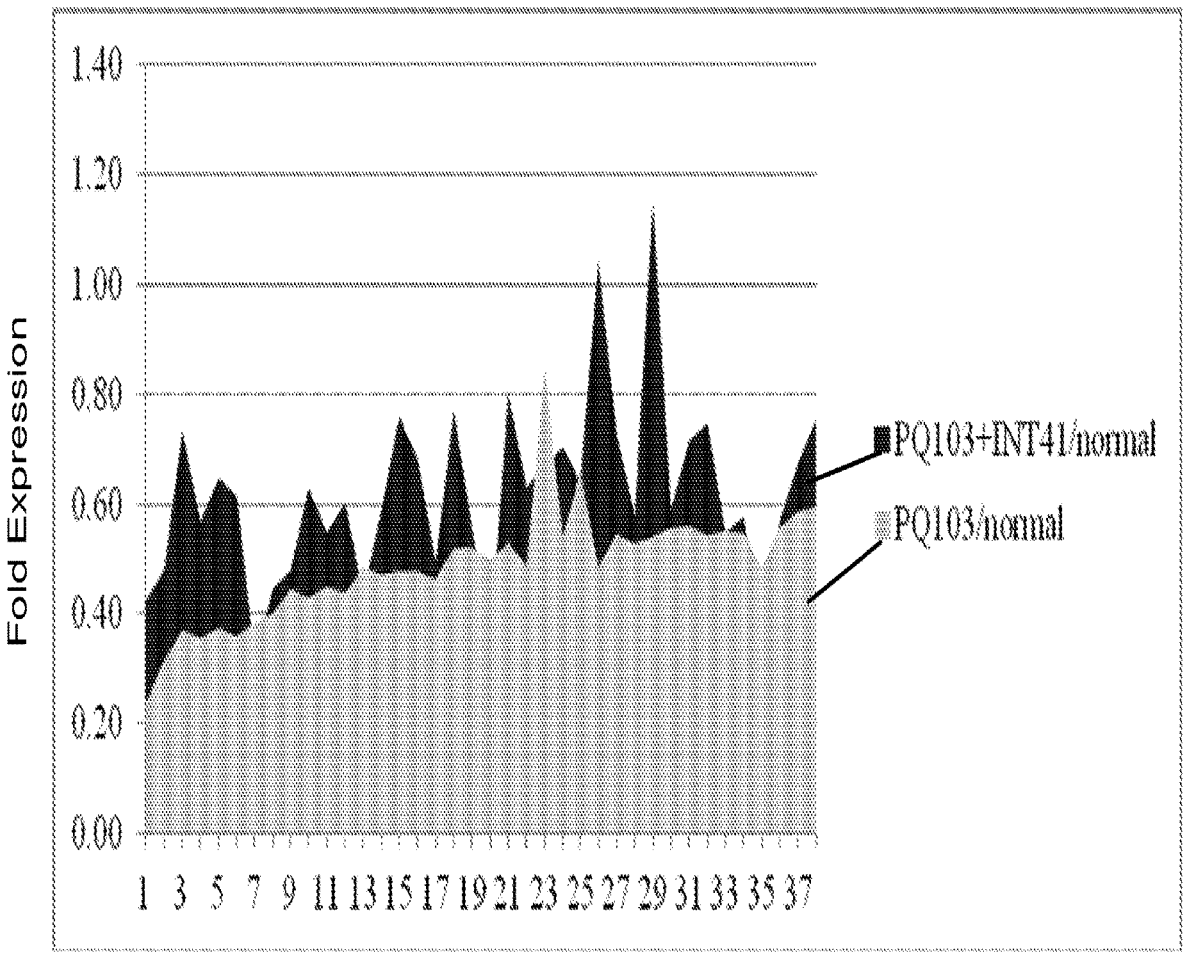
FIG. 7 shows the effects of INT41 on the under-expres-sion of genes caused by PQ103 ("Q103" disclosed as SEQ ID NO: 34).

FIG. 7 shows the effects of INT41 on the under-expression of genes caused by PQ103 ("Q103" disclosed as SEQ ID NO: 34). The increase in the fold expression of representative under-expressed genes is shown between cells expressing PQ103 alone or PQ103 and INT41 ("Q103" disclosed as SEQ ID NO: 34).

These FACS and gene expression results, taken together, demonstrate that INT41 prevents both the aggregation phenotype (FIGS. 4-5) as well as the genotype (gene dysregulation, FIGS. 6-7) that are both characteristic of Huntington's disease and linked by cause and effect.

Table 2 shows gene expression data for a few selected genes, which reveal that expression of INT41 alone does not result in pleiotropic gene regulation. The data show some of the genes affected by PQ103 ("Q103" disclosed as SEQ ID NO: 34), specifically those involved in heat shock or protein folding pathways, as well as degradation.

TABLE 2

| | | | | |
|---|---|---|---|---|
| ("Q103" disclosed as SEQ ID NO: 34) | | | | |
| Gene | PQ103[1] | PQ103 + INT41[2] | INT41[3] | Comments |
| NRCAM | 0.44 | 1.80 | NS | Neuronal CAM |
| IMMT | 0.32 | 1.66 | NS | Mitochondrial IM protein |
| ANXA4 | 0.36 | 1.58 | NS | Endo/exocytic |
| PCDH9 | 0.37 | 1.68 | NS | Neuronal protoadherin |
| BNIP3 | 0.38 | 1.91 | NS | Proapoptosis |
| NRP1 | 0.45 | 1.92 | NS | Neurophilin |
| UBE2E3 | 0.59 | 1.30 | NS | Ubiquitin conjugating enzyme |
| UBE2J2 | 6.32 | 0.58 | 2.7 | Ubiquitin conjugating enzyme |
| HSPA1B | 5.88 | 0.56 | NS | HSP701B stabilizes aggregation |
| PDF | 8.66 | 0.49 | 1.97 | Protein synthesis regulator |
| SPCS1 | 4.20 | 0.55 | NS | Ubiquitin signal peptidase |
| NCSTN | 4.17 | 0.57 | NS | Notch/beta amyloid cleavage (AZ) |
| CTSD | 4.07 | 0.37 | NS | Aspartylprotease (AZ) |
| HSP90AA | 2.79 | NS | NS | Cytosolic HSP90 alpha |

1, 3 = fold change vs. control 293 T adjusted for weighted error;
2 = fold change vs. PQ103 ("Q103" disclosed as SEQ ID NO: 34) adjusted for weighted error;
NS = not significant.

The data in Table 2 demonstrate that INT41 alone alters only the expression of genes required for synthesis and degradation of proteins, which would be expected for the added requirements in cells expressing INT41.

Example 5: INT41 Prevents a Toxic Fragment of the Mutant Huntingtin Protein from Binding to Chromatin in the Nucleus In another example, INT41 was studied in PC12 cells with an inducible gene for full length human Huntingtin protein for its effect on the sub-cellular localization and activity of mutant Huntingtin and its fragments.

PC12 rat neuron cells, initially developed at the Huntington's Disease Foundation (CHDI), were selected because similar inducible PC12 neurons were used by other laboratories that characterized toxic Huntingtin fragments (11).

Figure 8:
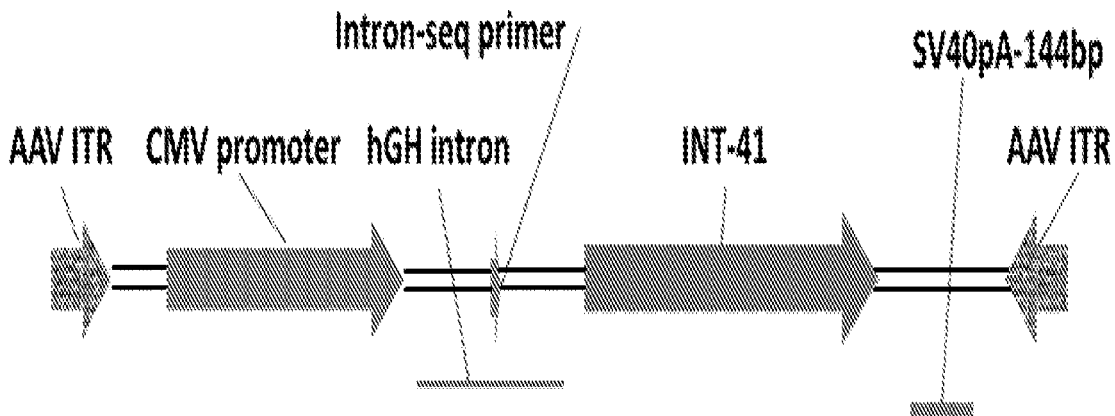
FIG. 8 is a schematic illustration of the construction of a recombinant adeno-associated virus (rAAV), as described by Chen, H. Mol Ther, 2008. 16(5): 924-311.

FIG. 8 is a schematic diagram of the construction of a rAAV (Chen, H. Mol Ther, 2008. 16(5): 924-30. The INT41 cDNA gene sequence was placed downstream from a cytomegalovirus (CMV) promoter and a human growth hormone (hGH) intron. The SV40 polyadenylation sequence (SV40 polyA) was placed downstream of the INT41 cDNA. The entire expression cassette was flanked by AAV6 inverted terminal repeat sequences (ITRs) required for vector packaging. A schematic of the expression cassette region of the vector is provided as FIG. 8. The AAV rep coding sequence was engineered to contain an artificial intron comprising an insect promoter so that both the Rep78 and Rep52 proteins required for AAV replication and packaging can be expressed from a single sequence. In addition, the artificial intron was also engineered into the AAV cap coding sequence to enable the expression of VP1, VP2, and VP3 proteins required to form viral particles in an optimal ratio. The engineered Rep and Cap sequences were cloned together to generate a recombinant baculovirus that expresses both the AAV Rep and Cap proteins. A second baculovirus was engineered to contain the target sequence flanked by the AAV ITRs. These two baculoviruses were used to co-infect insect cells for AAV vector production. After co-infection and amplification, the cell pellet is collected, lysed, cleared, and subjected to 2 rounds of cesium chloride ultracentrifugation. The AAV vectors are buffer-exchanged to PBS buffer or other suitable buffer depending on the requirement of the study. The titer of the AAV vectors was determined by a quantitative real-time PCR method, as known to those of skill in the art.

Figure 9:
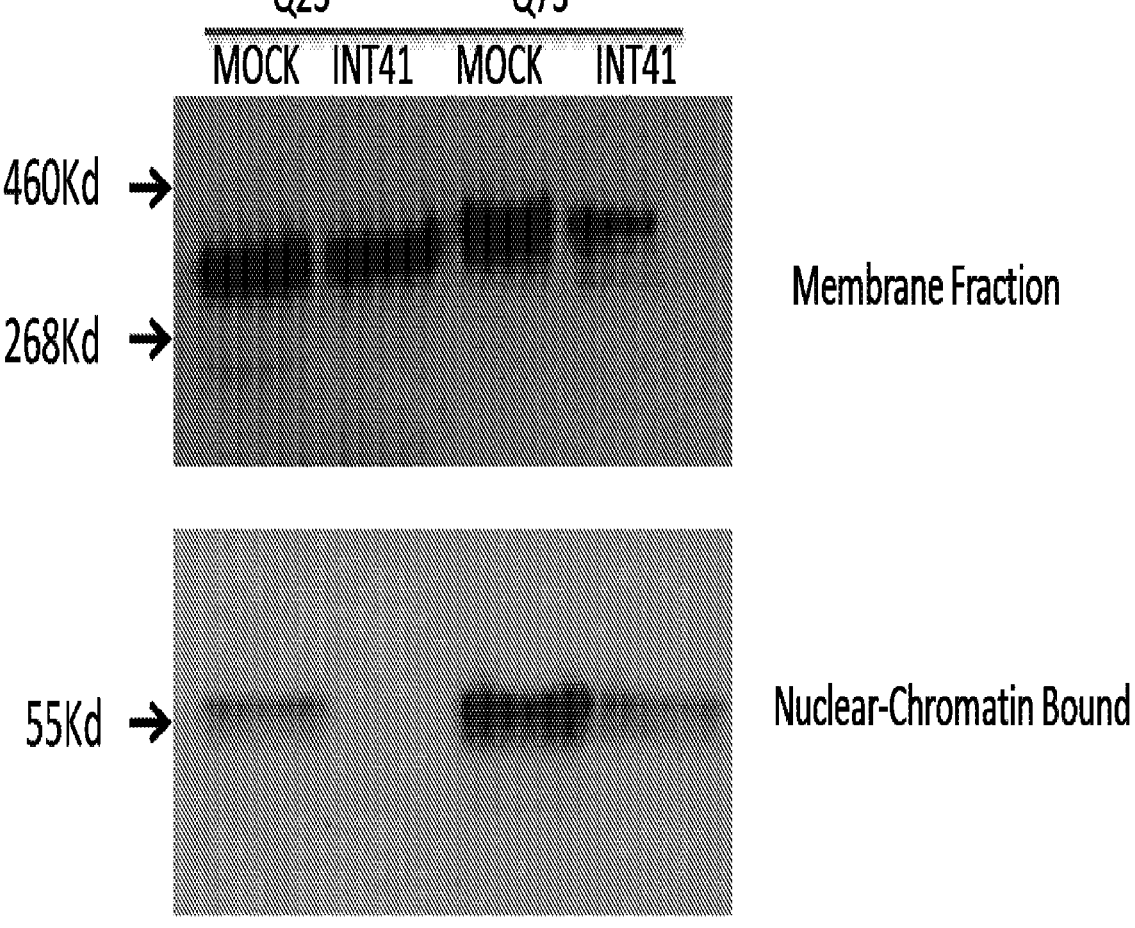
FIG. 9 demonstrates the effect of INT41 on inhibiting a toxic nuclear fragment from binding to chromatin in the nucleus. INT41 blocked membrane accumulation of full length Htt and blocked chromatin binding of toxic Htt Fragments (shown in a Western blot). Blots were probed with antibody to N-terminal fragment.

FIG. 9 demonstrates that in PC12 cells expressing HttpQ of 73 repeats (SEQ ID NO: 35), INT41 dramatically reduced the binding of the mutant Huntingtin protein fragment to chromatin in the nucleus and reduced the accumulation of full length mutant Huntingtin on membrane. Cells were transduced with recombinant INT41 containing adeno-associated virus 6 (rAAV6-INT41) and were induced to express human Huntingtin proteins after 72 hours. Cells were harvested on day 8, following induction of the human Huntingtin gene and sub-cellular fractionation was performed as described by the kit manufacturer (Thermo 78840). Protein concentration of each fraction determined using microBCA kit (Thermo 23235).

For analysis, 12 ug total protein from each fraction was loaded onto a 3-8% Tris-Acetate gel and run at 30 mAmps for 4 hours. Gel was subsequently transferred onto nitrocellulose (0.2 um, BioTraceNT) in Transfer Buffer (192 mM Tris, 25 mM Glycine, 20% Methanol) 30 V for 2 hours. The membrane was blocked in TBST/5% milk overnight and then probed with a rabbit-anti-Htt (Sigma H7540) antibody at 1:1500 in TBST/5% milk for 4 hrs RT. Three ten-minute washes with TBST preceded incubation with a goat-anti-rabbit IgG antibody conjugated to HRP (Jackson 111-035-003) at 1:5,000 in TBST/5% milk for 1 hr at room temperature. Three ten-minute washes with TBST were done prior to application of Pierce ECL2 (Thermo 80196) for chemiluminescent detection on film.

Figure 10:
FIG. 10 shows that the transcriptional regulatory CREB binding is increased in HttQ73 chromatin/DNA fraction ("Q73" disclosed as SEQ ID NO: 35) and that INT41 decreases CREB binding to chromatin/DNA. Immunoblots shown in FIG. 9 were re-probed with anti-CREB antibody (mock transduced with AAV6 ("M")), but binding of CREB to chromatin/DNA was reduced when cells were transduced with rAAV6-INT41 (lane marked as "41"). Lanes contain fractions from cytoplasmic (Cyto), membrane (Mem), nuclear soluble (Nsol) or chromatin/DNA (Chro) from cell lysates from induced PC12Q73 cells ("Q73" disclosed as SEQ ID NO: 35) that were transduced with either AAV6 not containing INT41 (M) or with rAAV6-INT41 (41).

FIG. 10 shows that the transcriptional regulatory CREB binding is increased in HttQ73 chromatin/DNA fraction ("Q73" disclosed as SEQ ID NO: 35) and that INT41 decreases CREB binding to chromatin/DNA. Immunoblots shown in FIG. 9 were re-probed with anti-CREB antibody (mock transduced with AAV6 ("M"), but binding of CREB to chromatin/DNA was reduced when cells were transduced with rAAV6-INT41 (lane marked as "41"). Lanes contain fractions from cytoplasmic (Cyto), membrane (Mem), nuclear soluble (Nsol) or chromatin/DNA (Chro) from cell lysates from induced PC12Q73 ("Q73" disclosed as SEQ ID NO: 35) cells that were transduced with either AAV6 not containing INT41 (M) or with rAAV6-INT41.

Figure 11:
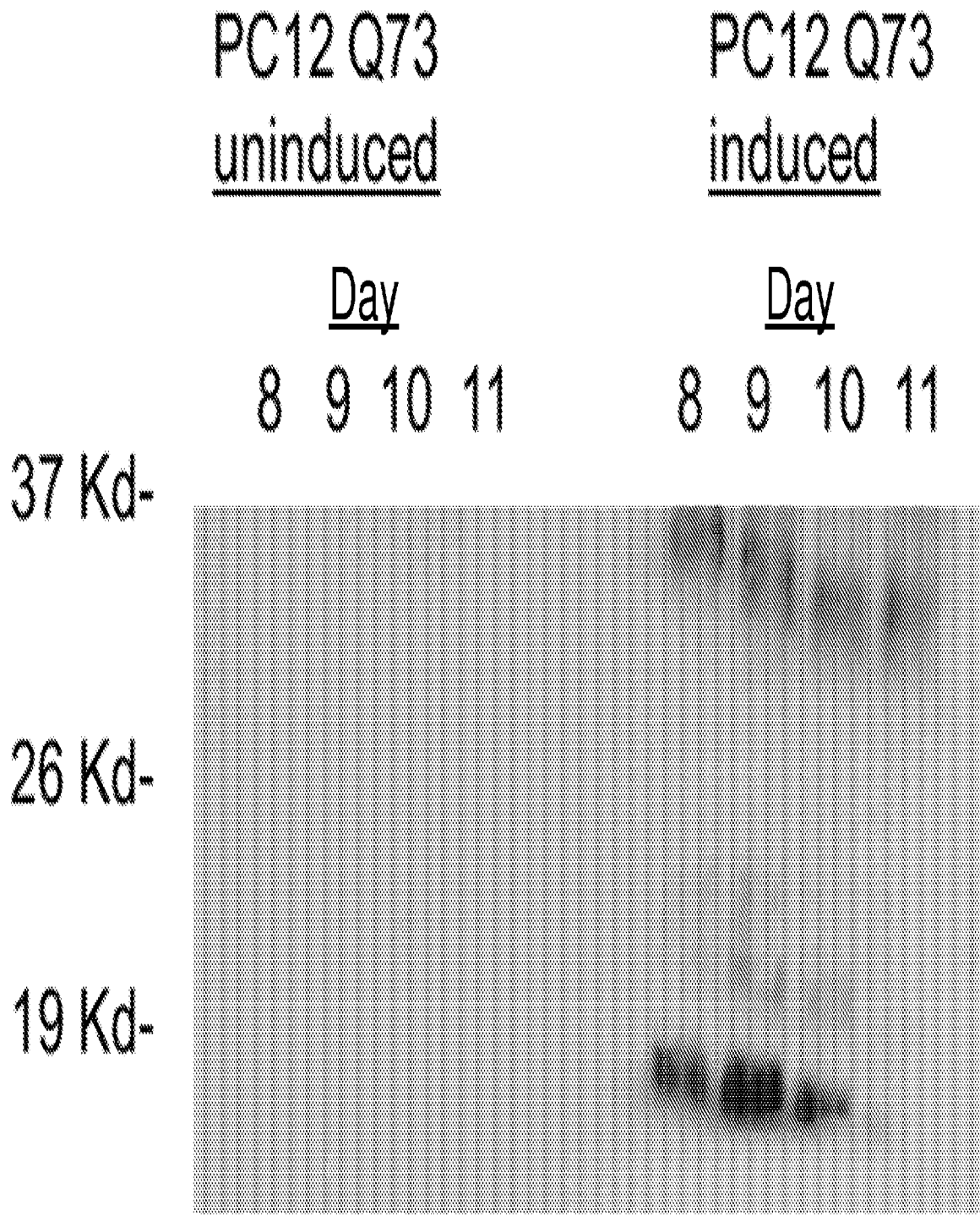
FIG. 11 shows an affinity purification of INT41 specific Htt degradation fragments.

FIG. 11 shows an affinity purification of INT41 specific Htt degradation fragments, in particular an affinity purification of induced and uninduced lysates at days 8-11 on immobilized INT41 Sepharose. FIG. 11 demonstrates that when lysates from HttQ73 ("Q73" disclosed as SEQ ID NO: 35) induced cells (right columns) are passed through an immobilized-INT41 affinity column, only smaller fragments of degraded Htt are bound (fractions probed with rabbit anti-N-terminal Htt antibody) and uninduced HttQ73 ("Q73" disclosed as SEQ ID NO: 35) cells (left columns (days 8, 9, 10, 11) do not bind any detectable proteins in fractions probed on the same blot. Fractions eluted with pH 2.5 glycine were spiked with 5 ug cytochrome C, then 100 ul of each was mixed with 400 ul cold acetone and incubated at −80° C. for 10 min and −20° C. overnight, and microfuged at 4° C. at 14,000×g for 10 min. Fractions were run on a 12% SDS PAGE gel, transferred to nitrocellulose and probed with anti-N-terminal Htt, followed by goat anti-rabbit-HRP and ECL development. Fractions 8-11 were run following a survey of fractions to determine which fractions contained eluted Htt or its fragments.

Example 6: INT41 Binds to Human Tau Protein at Hyperphosphorylated Regions for Treatment of Alzheimer's In other embodiments, INT41 can bind to the human Tau protein. FIG. 12 shows the Human Tau protein sequence, including 9 splice variants. INT41 epitopes are highlighted in bold and peptides associated with exosomes are outlined in boxes. FIG. 12 shows the INT41 epitopes ("PxP" in bold) which are the hyperphosphorlyated region of the Tau protein; the INT41 epitopes bind to sequences that are secreted in exosomes (FIG. 12 shows boxed sequences) (Pooler, et al. EMBO Reports 2113, 14:389-394; Saman et al. JBC 2012, 287:3842-3849).

INT41 can bind to fragments of HttpQ and alter the pathology and degradation of these fragments. Similarly, INT41's binding to fragments of Tau secreted by exosomes that cause neuron pathology and neuron loss can stabilize those fragments, facilitate degradation within the cell and prevent the secretion of Tau fragments in exosomes. Alternatively, although nor mutually exclusive, INT41 may be transported in exosomes bound to toxic Tau fragments and neutralize their extracellular activity.

Fragments of the Tau protein are secreted from cells in Alzheimer's patients, and Tau fragments bind to cellular receptors and cause neuron dysfunction. Introduction of an antibody in the extracellular space can be an effective therapy against Alzheimer's based on animal model studies because the antibody can prevent the binding of the Tau fragment to cellular receptors that cause neuron dysfunction (see Griswold-Prenner; Irene et al., U.S. Pub. No. 2001/
40086921). Preventing the secretion and/or hyperphospho-
rylation with an intrabody, such as INT41, can bind the Tau
fragment to cellular receptors and prevent neuron dysfunc-
tion.

The invention comprises a method of treating or manag-
ing a subject having Alzheimer's disease or other Tau
pathologies, comprising administering to a subject in need
of such treatment or management a therapeutically effective
amount of the intrabodies described herein. In an embodi-
ment, the intrabody prevents binding of a Tau fragment to
neurons causing neuron dysfunction.

Example 7: INT41 Improves Cognitive and Behavioral Function in Animal Models In another example, the INT41 intrabody was studied for
effects on cognitive and behavioral function in animal
models.

The R6/2 murine model was chosen because it is trans-
genic for HttpQ with large polyQ tracts (>120 repeats) (SEQ
ID NO: 37). This is an aggressive or acute model that
provides the ability to test in shorter periods of time and is
generally accepted as one of the best models for testing
neuroprotective or disease modifying therapeutic drugs.

Mice are born with aggregates of HttpQ and continue to
accumulate HttpQ with age. Therapeutic intervention began
at 5 weeks of age with optimal expression of transgenes 2-3
weeks post treatment. Therefore, therapeutic intervention
takes place well into disease progression in the R6/2 model.
The INT41 sequence was introduced with a recombinant
adeno-associated virus (rAAV Type 6). Wild-type AAV is
not associated with disease, and recombinant AAV vectors
have been modified to deliver encoded transgenes and are
incapable of viral replication. AAV is highly tropic for
neurons, making it an ideal delivery system for neurode-
generative diseases.

Recombinant AAV6-INT41 (rAAV6-INT41, along with
rAAV6-GFP and rAAV-Happ1 as controls) were adminis-
tered by interstriatal bilateral injection of 1.5 µl each in
transgenic animals along with a nontransgenic R6/2 group
that received only vehicle (buffer used for injection). Animal
testing was blind to the trained tester and recorded for each
animal for all movement and cognitive related tests. rAAV6
administration at 5 weeks resulted in optimal expression 2-3
weeks post administration (INT41, GFP and Happ1 esti-
mated optimal expression at between 7 and 8 weeks). Table
3 below shows the groups studied and number of female and
male subjects in each group.

TABLE 3

| Genotype | Treatment | Female | Male |
|---|---|---|---|
| R6/2_Wt | VEH | 5 | 9 |
| R6/2_Tg | GFP | 5 | 9 |
| | Happ1t | 5 | 9 |
| | INT41 | 6 | 9 |

A number of standard tests were run before the introduc-
tion of rAAV at 5 weeks of age, and these tests were
continued until the animals were sacrificed after 12 weeks
for pathology.

TABLE 4

| Study Week | Procedures |
|---|---|
| 1 | Breeding set-up |
| 2&3 | |
| 4 | Birth week |
| 5 | |
| 6 | Tails sent for genotyping. By end of week, receive genotyping results |
| 7 | Weaning week |
| 8 | 4 Week behavioral Baseline Assessment (OFAM, GS, RR) |
| 9 | 4.5-5 Week-Interstriatal rAAV6 Infusions |
| 10 | 6 Week Behavioral Assessment (OFAM, GS, RR) |
| 11 | 7 Week |
| 12 | 8 Week (OFAM, GS, RR) |
| 13 | 9-10 Week Behavioral Assessment-Cognition Using Procedural T-Maze |
| 14 | (Typically 2 Week Test) |
| 15 | 11 Week |
| 16 | 12 Week Behavioral Assessment (OFAM, GS) and Tissue collection |

Various tests are defined below. Rotarod (RR): Mice are
tested over 3 consecutive days. Each daily session includes
a training trial of 5 minutes (min) at 4 RPM on the rotarod
apparatus (Rotamex, OH). One hour later, the animals were
tested for 3 consecutive accelerating trials of 5 min each
during which speed changes over 300 seconds. The inter-
trial interval was at least 30 min. The latency to fall from the
accelerating rod was recorded, and quantitative analysis was
performed.

Open field (OFAM): Activity chambers (Med Associates
Inc, St Albans, VT; 27×27×20.3 cm) were equipped with
infrared (IR) beams. Mice were placed in the center of the
chamber, and their behavior was recorded for 30 min.
Quantitative analysis was performed on the following five
dependent measures: total locomotion, locomotion in the
center of the open field, rearing rate in the center, total
rearing frequency and velocity.

Grip strength (GS): Grip strength was used to assess
muscular strength in both the forelimb and hindlimb
muscles. In brief, mice were scruffed, held gently by the tail,
and were lowered towards the first mesh grip piece on the
gauge (Chatillion Force Gauge, San Diego Instruments, San
Diego, CA) until the animal grabbed with both front paws.
The animal was then lowered toward the platform and gently
pulled straight back with consistent force until it released its
grip at which point its hindlimbs grasped the second mesh
grip piece, continuing the gentle pulling motion until the
subject released its grasp Both the forelimb and hindlimb
grip forces were recorded on the strain gauge. Animals
underwent 5 trials per testing session, and the average of the
trails was used to calculate the grip force. After testing,
animals were placed back into their home cage.

Clasping Test: The clasping test was used to observe
clasping of the forelimbs and hindlimbs while suspended by
the tail. Mice were picked up at the end of their tail and held
for 30 seconds, approximately 12 inches above the cage.
During the elapsed time, if toes of the opposing limbs
interlock and remain clasped for greater than one second, it
is scored as a clasp and categorized as forelimb, hindlimb or
full clasp (both forelimb and hindlimb). After 30 seconds,
mice were lowered back into their home cage.

Procedural T-Maze: Mice were tested in two T-mazes
constructed of black Plexiglas (built in-house at Psycho-
Genics, Inc.). Each T-maze was located in a separate test
room, dimly-lit and equipped with a video camera (mounted
above the T-maze) and a computer and monitor. The monitor screen was covered with a red transparent film to minimize light emission. The T-maze was filled with water at 25° C.+/−1° C., colored with Tempura non-toxic white paint to render it opaque. At one end of the cross-piece of the 'T', a platform was located approximately 0.5 cm below the level of the water.

Mice were placed in the stem of the T-shaped maze and allowed to make a choice to swim into either the right or left arm to reach an escape platform. A choice was defined as entry into either the left or right arm, without necessarily reaching the escape platform. Failure to leave the stem of the T-maze was defined as 'no-choice'. Any mouse that failed to reach the platform within the maximum trial duration (60 seconds (s)) was placed directly onto the platform. In all cases, once an animal reached or was placed on the platform, the animal was allowed to remain there for 30 s and was then placed back into a pre-warmed holding cage allowing the fur to dry between blocks. Each mouse was trained for 8 trials per day. Testing was conducted in blocks of approximately 8 mice, such that every mouse performed one trial before returning to the first mouse for the second trial. Thus, inter-trial intervals were maintained at approximately 15 minutes. Mice were tested for 6 days per week, for a maximum of 2 weeks (total 12 sessions). Acquisition of the task was defined as 75% correct for two consecutive days. After acquisition, individual mice were progressed on to reversal testing: all mice that acquired the task underwent 6 days of reversal testing, regardless of performance. Mice were monitored at all times when in the pool. If an animal struggled to stay above the water in the first trial, the experiment was terminated for that mouse.

Body Weight: FIGS. 13A and 13B show body weight differentiation between treated and control groups. Body weight differentiation only became evident between 10-12 weeks, particularly in male mice, which typically progressed more rapidly than females, by roughly 2 weeks. No differences in body weight of R6/2 transgenic mice were observed between rAAV-treated groups. In FIGS. 13A and 13B, the mean body weights are shown (±S.E.M.) of R6/2_WT and R6/2_Tg mice following treatment with rAAV6-GFP, rAAV6-Happ1t, rAAV6-INT41, or VEH (vehicle) from 4-12 weeks of age (open circle: vehicle in R6/2 WT controls; black square: rAAV-GFP in R6/2 Tg; gray square: rAAV-Happ1t in R6/2 Tg; open square: rAAV-INT41 in R6/2 Tg).

Open Fields Tests: Open Field tests measured movement of animals placed in the center of the testing field and the total distance traveled and velocity of movement. GFP controls, in female mice only, exhibited unusually high and unexpected total distance traveled. R6/2 transgenic mice treated with INT41 showed significantly greater distance traveled from the center relative to Happ1t. Mice treated with Happ1t were significantly lower than GFP mice as measured by distance traveled, particularly relative to wild-type vehicle controls in female mice.

Figure 14:
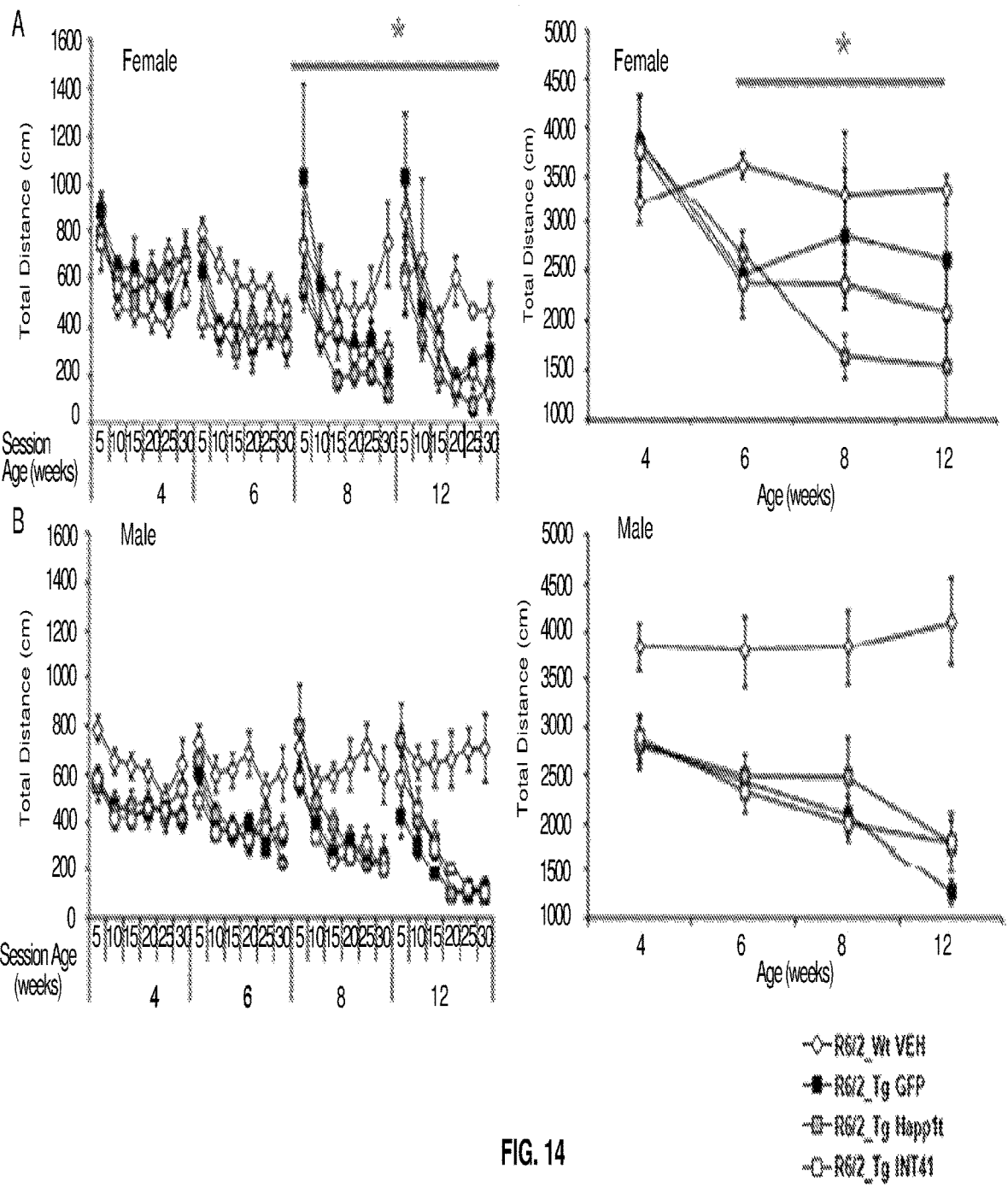
FIG. 14 illustrates results of an Open Field test measuring movement of animals placed in the center of the testing field and the total distance traveled and velocity of movement. Groups of R6/2_Tg and WT mice transfected with rAAV6-GFP, rAAV6-Happ1t, rAAV6-INT41, or vehicle (VEH) were tested at 4, 6, 8 and 12 weeks of age.

FIG. 14 shows the results of the Open Field test measured by the mean (±S.E.M.) total distance traveled in the open field by R6/2_Tg and WT mice at 4, 6, 8 and 12 weeks of age. Data was obtained at 4 wks of age and served as baseline data for distribution of mice into treatment groups. The data obtained at 6, 8 and 12 weeks of age following treatment with rAAV6-GFP, rAAV6-Happ1t, rAAV6-INT41, or vehicle (VEH) at 5 weeks of age represented 1, 3 and 7 weeks post-infusion time points. FIG. 14 shows data presented across the five minute time intervals, as well as for the sum of the entire 30 minute session. Data are presented for females (A) and males (B) separately. Table 5 below shows the statistical comparison (P value significance) between treatment groups for the open field test.

TABLE 5

| Open Field Test Open Field: Distance Total Gender × Group (genotype / treatment) × Age Interaction $F_{(9, 206)} = 2.02, p = 0.0444$ | | | |
|---|---|---|---|
| | Comparison | 8 Weeks | 12 Weeks |
| Females | GFP vs. INT41 | 0.3698 | 0.0673 |
| | GFP vs. Happ1t | 0.0102 | 0.0125 |
| | Happlt vs. INT41 | 0.0694 | 0.4005 |
| Males | No differences | N/A | N/A |

Figure 15:
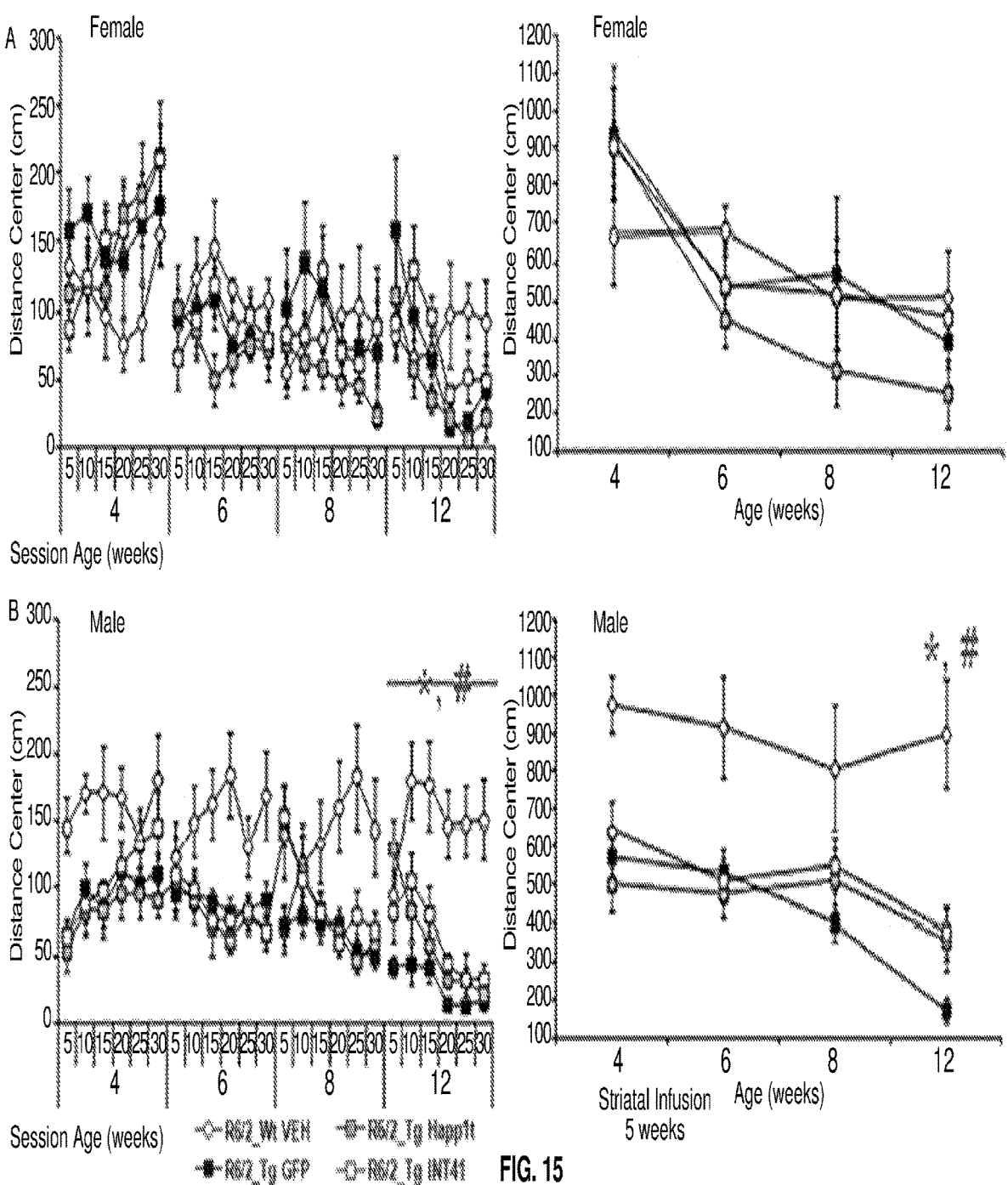
FIG. 15 shows the results for an open field distance traveled from center test (represented by the mean (±S.E.M.) distance traveled in the center of the open field) by R6/2_Tg and WT mice at 4, 6, 8 and 12 weeks of age transfected with rAAV6-GFP, rAAV6-Happ1t, rAAV6-INT41, or vehicle.

FIG. 15 shows the data for an open field distance traveled from center test. The data is represented by the mean (±S.E.M.) distance traveled in the center of the open field by R6/2_Tg and WT mice at 4, 6, 8 and 12 weeks of age. Data obtained at 4 wks of age served as baseline data for distribution of mice into treatment groups. Data obtained at 6, 8 and 12 weeks of age following treatment with rAAV6-GFP, rAAV6-Happ1t, rAAV6-INT41, or vehicle at 5 weeks of age represented 1, 3 and 7 weeks post-infusion time points. Data were presented across the five minute time intervals, as well as for the sum of the entire 30 minute session. FIG. 15 shows data for females (A) and males (B) separately. The asterisk (*) indicates that INT41-treated mice showed significantly different distances traveled from GFP (p<0.05). The #indicates that Happ1t approached a significant difference from GFP (p=0.0623).

Grip Strength Test: Grip strength was tested and recorded with a strain gauge. The average of five recorded values was reported. INT41-treated R6/2 transgenic mice demonstrated significant improvement in hind limb grip strength as compared to hind limb grip strength of GFP controls in the same mouse strain. No effect on forelimb strength was observed.

FIG. 16 shows non-normalized hind limb grip strength in mice treated with intrabodies INT41, Happ1t, GFP or vehicle (control). The effects of rAAV6-INT41, rAAV6-Happ1t or rAAV6-GFP on the hindlimb grip strength of R6/2_Tg mice are shown as compared to VEH-treated R6/2_WT mice. Data are presented for females (FIG. 16, panel A) and males (FIG. 16, panel B) separately. 4 weeks was the baseline for all treated mice. INT41 showed a significant difference in hind limb grip strength as compared to GFP-control mice at 12 weeks (p<0.05). Happ1t approached significant difference from GFP-control (p=0.0623).

Clasping Response: The clasping response was tested in R6/2 transgenic mice treated with INT41 or Happ1 or controls. The clasping response was only seen in the R6/2 transgenic mice who grabbed themselves when picked up by the tail, rather than reaching out to grab something in their environment. INT41 treated R6/2 transgenic mice demonstrated significant delays in acquiring this modified behavior, similar to Happ1 treated mice.

Figure 17:
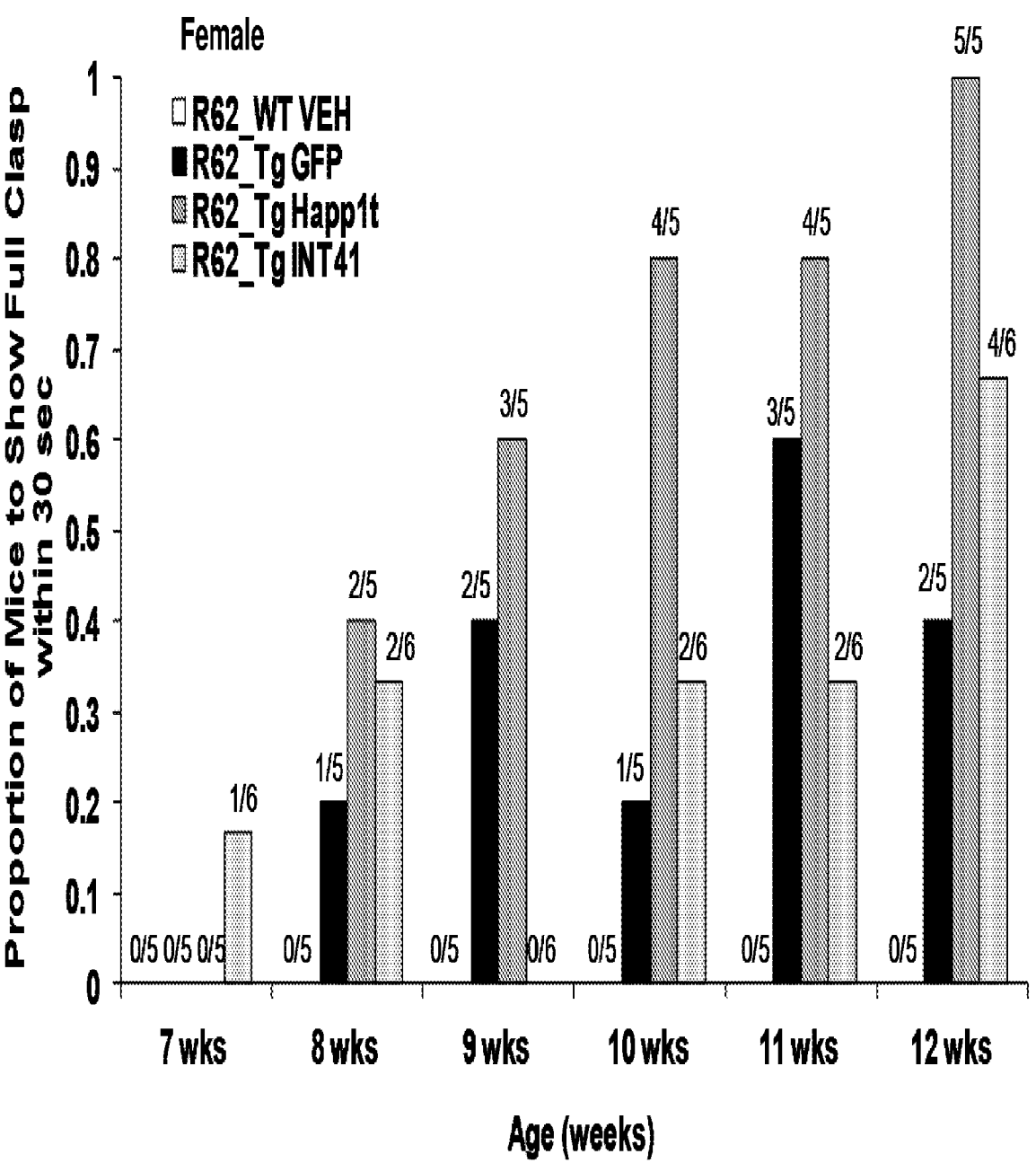
FIG. 17 illustrates the clasping responses in female INT41-treated mice, Happ1t-treated mice, GFP-treated mice or control vehicle treated mice. The proportion of mice each week presenting with a full limb clasp is depicted as evaluated from 7-12 weeks of age following bilateral striatal infusion of rAAV6-INT41, rAAV6-Happ1t, rAAV6-GFP or VEH at 5 weeks of age. Clasping was assessed at 4, 5 and 6 weeks of age.
Figure 18:
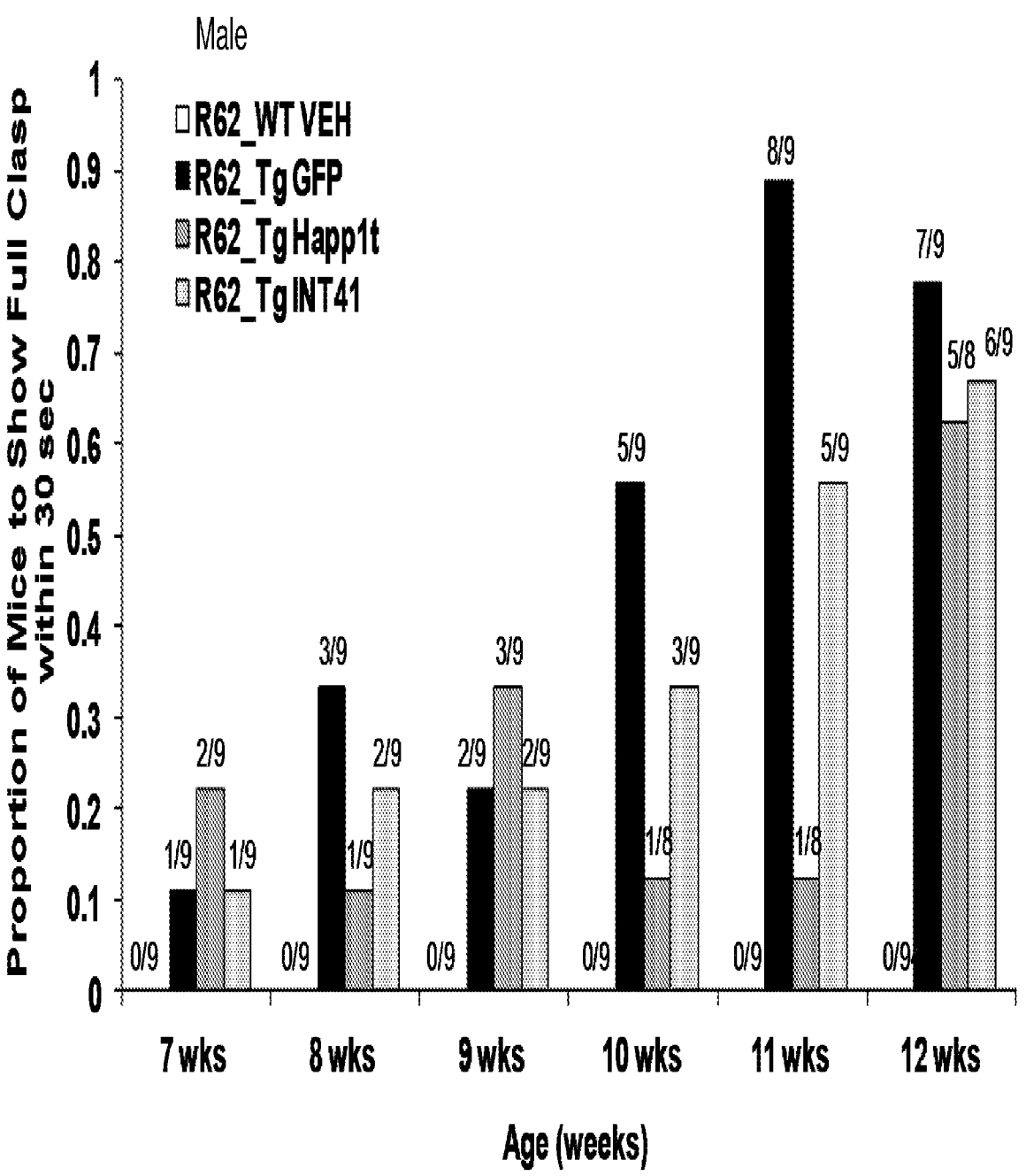
FIG. 18 illustrates the clasping responses in male INT41-treated mice, Happ1t-treated mice, GFP-treated mice or control vehicle treated mice. The proportion of mice each week presenting with a full limb clasp is depicted as evaluated from 7-12 weeks of age following bilateral striatal infusion of rAAV6-INT41, rAAV6-Happ1t, rAAV6-GFP or VEH at 5 weeks of age. Clasping was assessed at 4, 5 and 6 weeks of age.

In FIGS. 17-18, the clasping responses of INT41-treated mice, Happ1t-treated mice, GFP-treated mice or control vehicle treated mice are shown (FIG. 17 shows results for female mice; FIG. 18 shows results for male mice). The proportion of mice each week presenting with a full limb clasp is depicted, as evaluated from 7-12 weeks of age following bilateral striatal infusion of rAAV6-INT41, rAAV6-Happ1t, rAAV6-GFP or VEH at 5 weeks of age. Clasping was assessed at 4, 5 and 6 weeks of age, but since no mice displayed a clasping phenotype, the ages were not included in the figures above.

Chi square analysis of full clasping behavior observed in R6/2_Tg mice treated with rAAV6-Happ1t as compared to rAAV6-GFP treated R6/2_Tg mice showed the following:

In the gender combined data, a smaller proportion of R6/2_Tg mice treated with Happ1t displayed full clasping behavior at 11 wks of age (p=0.0341).

In R6/2_Tg females only: At 10 wks, there was a trend for a higher proportion of Happ1t treated R6/2_Tg females to display full clasping behavior as compared to female GFP-treated counterparts (p=0.0578). At 12 weeks of age a significantly higher proportion of Happ1t-treated R6/2_Tg females did display more full clasps than did the GFP-treated R6/2_Tg females (p=0.0384).

In the R6/2_Tg males only: At 10 wks, there was a trend for a smaller proportion of Happ1t treated R6/2_Tg males to display full clasping behavior as compared to male GFP-treated counterparts (p=0.0637). At 11 weeks of age, a significantly lower proportion of Happ1t-treated R6/2_Tg males did display more full clasps than did the GFP-treated R6/2_Tg males (p=0.0016).

Chi square analysis comparing the frequency of full clasping behavior in R6/2_Tg mice treated with rAAV6-INT41 as compared directly to rAAV6-GFP treated R6/2_Tg mice revealed a trend at 11 wks of age for INT41-treated R6/2_Tg mice (gender combined) to display a lower proportion of full clasps (p=0.0768). No gender-specific effects were noted.

T-Maze cognitive test: The T-Maze cognitive test measures the ability to learn where a platform is located while swimming in a T configured tank with a platform on one side of the T. Learning is shown by the ability to learn the location of the platform on two consecutive days. The group is determined to have achieved learning when 75% acquire the task.

In this test, the INT41 treated female R6/2 transgenic achieved learning of the task in the same time as the nontransgenic control mice. Male mice (who progress in disease at a faster rate) treated with INT41 were better in learning than the GFP or Happ1 mice, but not the nontransgenic control.

Figure 19:
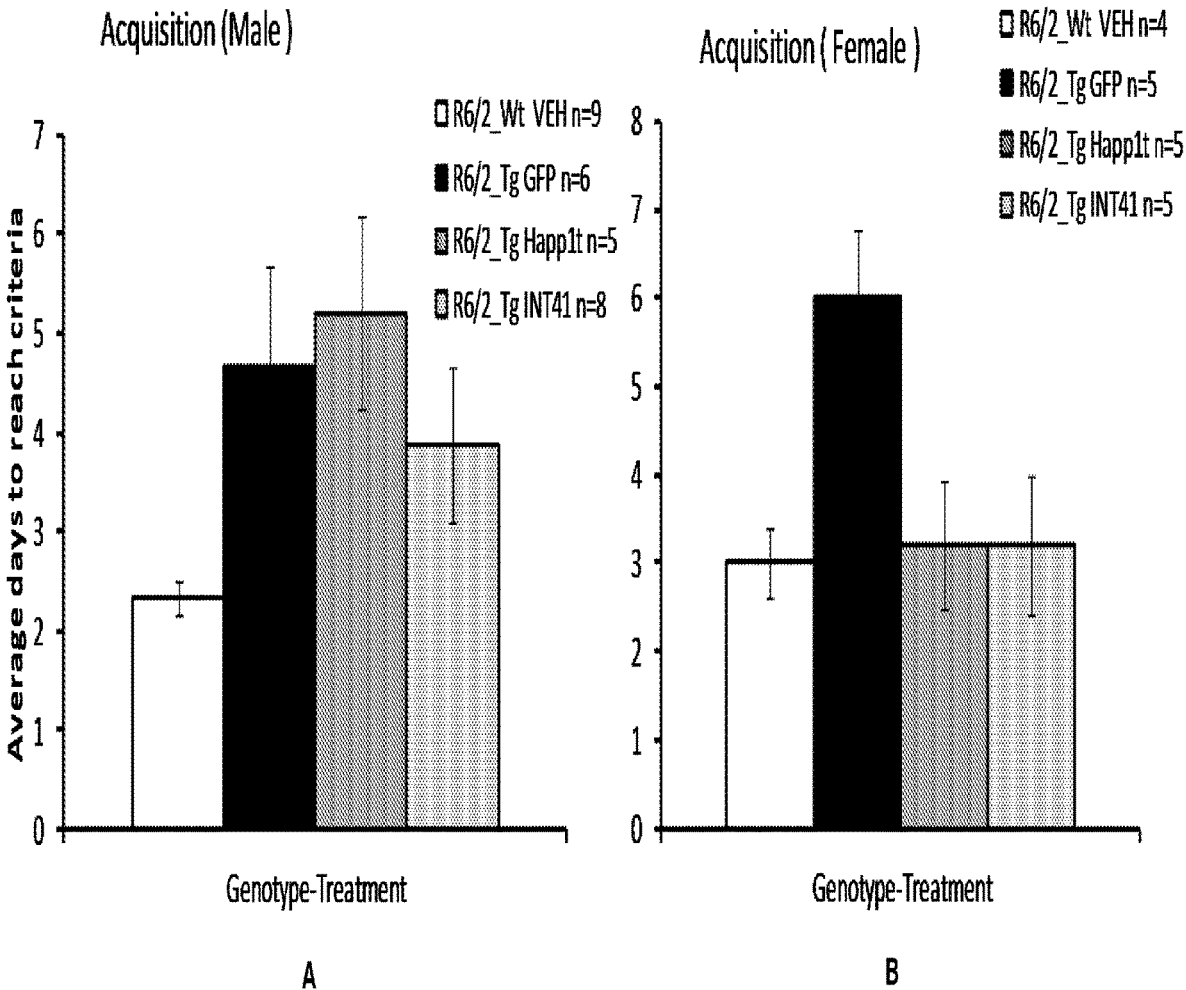
FIG. 19 shows the results for the T-Maze cognitive test, measuring the proportion of mice achieving Task Acquisi-tion in male and female mice (at 9-10 weeks). Treatment groups included R6/2_Wildtype mice transfected with vehicle (n=9), R6/2_Tg mice transfected with GFP (n=6), R6/2_Tg mice transfected with Happ1t (n=5), and R6/2_Tg mice transfected with INT41 (n=8).

FIG. 19 shows the results for the T-Maze cognitive test, measuring the proportion of mice achieving Task Acquisition in male and female mice (at 9-10 weeks). FIG. 19A shows results for male mice; FIG. 19B shows results for female mice. The acquisition of the procedural T-maze task was measured in the average number of days to acquire the task. Data was expressed as mean±SEM. Asterisks (*p<0.05, **p<0.01) indicate significant difference compared to R62-WT vehicle. T-Maze results demonstrated that INT41 and Happ1 treated female mice, as a group, performed as well as controls. In male mice, INT41 treated mice performed better than both GFP and Happ1t mice, but the differences were not statistically significant.

Example 8: Summary of Animal Model Tests

Table 6 below shows the summary of results for the animal model studies performed using INT41. The results indicate positive results for INT41 across several behavioral and cognitive endpoints.

TABLE 6

| Summary of Animal Model Results | | |
|---|---|---|
| Test | Controls | INT-41* |
| Survival | 4 unscheduled deaths | One unscheduled death |
| Open field-total distance | Gradual decline | Increased movement in early time points |
| Open field-distance center | Gradual decline | Significant improvement at 12 weeks |
| Open field-velocity | Gradual decline | Improvement in females at 12 weeks |
| Hind grip strength | Variable decline | Improvement in males at 12 weeks |
| Full clasping | GFP control increases clasping; delays with Happ1t | Delay in clasping behavior |
| Procedural T-Maze | Time to learn is demonstrably slow | Females identical to vehicle non-transgenic control |

Example 9: Immunohistochemical Enumeration of Aggregates in R6/2 Brain Sections In one example, the immunohistochemical enumeration of aggregates in R6/2 brain sections from mice was studied. The enumeration of aggregates from immunohistochemical staining of brain sections was determined by bilateral enumeration at two cross-section levels per animal (and performed identically across all animals) with a 40× objective. Both striata were imaged at two different coronal levels—4 images per animal and analyzed as described by Simmons, et al. [16].

TABLE 7

| Analysis of HttpQ aggregates in R6/2 animals | | | |
|---|---|---|---|
| | GFP | Happ1t | INT41 |
| Median aggregate number (avg deviation) | 1365 (219) | 1543 (299) | 1240 (209) |
| Female Median aggregate number (avg deviation) | 1325 (238) | 1543 (308) | 1184 (156) |
| Frequency/animal of aggregates 0.01-0.1 um | 227 | 266 | 176 |
| Frequency/animal of aggregates 0.1-1 um | 741 | 748 | 611 |

The fields examined included between 1,000 and 2,000 aggregates per animal in approximately the same plane of the striatum. The results demonstrated the INT41 groups had fewer aggregates overall. When aggregates were examined by frequency analysis (GraphPad Prism 6.0), the INT41 group had fewer aggregates in the smaller size range consistent with inhibiting the initial aggregation of HttpQ. The frequency of 0.01-0.1 μm aggregate numbers in INT41 mice were 22% (p<0.13) lower than GFP and 34% (p<0.05) lower than Happ1t mice. The frequency of 0.1-1 μm aggregates in INT41 mice were 16% (p<0.09) lower than GFP and 18% (p<0.10) lower than Happ1t mice.

Disease modification in Huntington's Disease requires that a therapeutic agent block or prevent the continuing cascade of events that is initiated by aggregation of HttpQ and results in neuron death. INT41 has the properties consistent with disease modification in both cell-based systems where it blocked HttpQ103-GFP ("Q103" disclosed as SEQ ID NO: 34) aggregation and gene dysregulation and in animal models where it improved motor and cognitive function. Animal models for Huntington's disease fail to capitulate human clinical results, but the mechanistic features of HttpQ aggregation have been well studied and linked closely with human disease. Pools of soluble aggregates decline with age as insoluble aggregates accumulate [17, 18], and this dynamic may be altered by INT41 based on the inhibition of the formation of small aggregates in the brains of INT41 treated R6/2 mice (Table 6).

The R6/2 studies demonstrated improvements in several tests of motor and cognitive function, primarily in female mice where disease progression is not as rapid. These studies, both in vitro and in vivo, suggest that INT41 can slow or prevent early aggregation of HttpQ supporting early intervention as a therapeutic imperative. Although Happ1t performed similarly to INT41, several animals in the Happ1t group died earlier (data not shown), but this observation could not be confirmed without a formal survival study.

The solubility differences between INT41 and Happ1t in *E. coli* and mammalian expression systems suggest that Happ1t has folding problems that could be due to the absence of a heavy chain, leaving light chain domains that normally interact with heavy chain domains to seek out self-self association or association with other proteins that could result in aggregation.

Comparison of the data with historical control R6/2 transgenic mice indicate that GFP unexpectedly had some disease modifying effect in some of the tests, specifically open field. A review of historical controls and published GFP baseline data suggests that GFP mice may have declines less rapidly than expected, particularly as seen in FIG. 9. The effect of GFP may be attributable to the increase in genes regulating protein degradation particularly several ubiquitin related genes that modify proteins for degradation [19]. However, the effect of GFP is short-lived and only direct comparison with a TG control would be required to confirm any differences.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. Zuccato, C., M. Valenza, and E. Cattaneo, Molecular mechanisms and potential therapeutical targets in Huntington's disease. Physiol Rev, 2010. 90(3): p. 905-81.
2. Schulte, J. and J. T. Littleton, The biological function of the Huntingtin protein and its relevance to Huntington's Disease pathology. Curr Trends Neurol, 2011. 5: p. 65-78.
3. Kippert, F. and D. L. Gerloff, Highly sensitive detection of individual HEAT and ARM repeats with HHpred and COACH. PLoS One, 2009. 4(9): p. e7148.
4. Xia, J., et al., Huntingtin contains a highly conserved nuclear export signal. Hum Mol Genet, 2003. 12(12): p. 1393-403.
5. Landles, C., et al., Proteolysis of mutant huntingtin produces an exon 1 fragment that accumulates as an aggregated protein in neuronal nuclei in Huntington disease. J Biol Chem, 2010. 285(12): p. 8808-23.
6 Riva, L., et al., Poly-glutamine expanded huntingtin dramatically alters the genome wide binding of HSF1. J Huntingtons Dis, 2012. 1(1): p. 33-45.
7. Benn, C. L., et al., Huntingtin modulares transcription, occiies gene promoters in vivo, and binds directly to DNA in a polyglutamine dependent manner. Neurobiology of Dis., 2008. 28 (42): p. 10720-33.
8. Labbadia J., et al., Altered chromatin architecture underlies progressive impairment of heat shock reesponse in mouse models of Huntington Disease. J Clin Invest., 2011. 121 (8): p. 3306-19.
9. Wellington, C. L., et al., Caspase cleavage of mutant huntingtin precedes neurodegeneration in Huntington's disease. J Neuroscience, 2002. 22 (18): p. 7662-72.
10. Graham, R. K., et al., Cleavage at the caspase 6 site is required for neuronal dsfunction and degeneration due to mutant huntingtin. Cell, 2006. 125 (6): p. 1179-91.
11. Ratovitski T., N-terminal proteolysis of full-length mutant huntingtin in an inducible PC12 cell model of Huntington's disease. Cell Cycle, 2007. 6 (23): p. 2970-81.
12. Khoshnan, A., J. Ko, and P. H. Patterson, Effects of intracellular expression of anti-huntingtin antibodies of various specificities on mutant huntingtin aggregation and toxicity. Proc Natl Acad Sci USA, 2002. 99(2): p. 1002-7.
13. Southwell, A. L., et al., Intrabodies binding the proline-rich domains of mutant huntingtin increase its turnover and reduce neurotoxicity. J Neurosci, 2008. 28(36): p. 9013-20.
14. Southwell, A. L., J. Ko, and P. H. Patterson, Intrabody gene therapy ameliorates motor, cognitive, and neuropathological symptoms in multiple mouse models of Huntington's disease. J Neurosci, 2009. 29(43): p. 13589-602.
15. Southwell, A. L., et al., Perturbation with intrabodies reveals that calpain cleavage is required for degradation of huntingtin exon 1. PLoS One, 2011. 6(1): p. e16676.
16. Fisher, A. C. and M. P. DeLisa, Efficient isolation of soluble intracellular single-chain antibodies using the twin-arginine translocation machinery. J Mol Biol, 2009. 385(1): p. 299-311.
17. Fisher, A. C., W. Kim, and M. P. DeLisa, Genetic selection for protein solubility enabled by the folding quality control feature of the twin-arginine translocation pathway. Protein Sci, 2006. 15(3): p. 449-58.
18. Karlsson, A. J., et al., Engineering antibody fitness and function using membrane-anchored display of correctly folded proteins. J Mol Biol, 2012. 416(1): p. 94-107.
19. Waraho, D. and M. P. DeLisa, Versatile selection technology for intracellular protein-protein interactions mediated by a unique bacterial hitchhiker transport mechanism. Proc Natl Acad Sci USA, 2009. 106(10): p. 3692-7.
20. Ball, L. J., et al., Recognition of proline-rich motifs by protein-protein-interaction domains. Angew Chem Int Ed Engl, 2005. 44(19): p. 2852-69.
21. Srinivasan, M. and A. K. Dunker, Proline rich motifs as drug targets in immune mediated disorders. Int J Pept, 2012. 2012: p. 634769.
22. Simmons, D. A., et al., Brief ampakine treatments slow the progression of Huntington's disease phenotypes in R6/2 mice. Neurobiol Dis, 2011. 41(2): p. 436-44.
23. Baldo, B., et al. et al., TR-FRET-based duplex immunoassay reveals an inverse correlation of soluble and aggregated mutant huntingtin in huntington's disease. Chem Biol, 2012. 19(2): p. 264-75.
24. Marcellin, D., et al. et al., Fragments of HdhQ150 mutant huntingtin form a soluble oligomer pool that declines with aggregate deposition upon aging. PLoS One, 2012. 7(9): p. e44457.
25. Bennett, E. J., et al., Global changes to the ubiquitin system in Huntington's disease. Nature, 2007. 448(7154): p. 704-8.

What is claimed is:

1. A method of treating or managing a subject having a disease associated with aggregation of Huntingtin protein in a cell, wherein the disease associated with aggregation of Huntington protein is Huntington's disease, comprising administering to a subject in need of such treatment or management a therapeutically effective amount of an intrabody comprising an amino acid sequence comprising: a variable heavy sequence, a variable light chain sequence, and a linker sequence interposed between the variable heavy sequence and the variable light sequence, wherein the variable heavy sequence comprises: a variable heavy complementarity-determining region (CDR) 1 sequence comprising SEQ ID NO: 21, a variable heavy CDR2 sequence comprising SEQ ID NO: 22, and a variable heavy CDR3 sequence comprising SEQ ID NO: 6; and wherein the variable light sequence comprises: a variable light CDR1 sequence comprising SEQ ID NO: 23, a variable light CDR2 sequence comprising SEQ ID NO: 24, and a variable light CDR3 sequence comprising SEQ ID NO: 10.

2. The method of claim 1, wherein the intrabody specifically binds Huntingtin protein.

3. The method of claim 1, wherein the subject is a human.

4. The method of claim 1, wherein the linker sequence comprises a glycine-rich sequence.

5. The method of claim 4, wherein the glycine-rich sequence comprises SEQ ID NO: 16.

6. The method of claim 1, wherein the intrabody is administered to the subject as part of a pharmaceutical composition comprising a pharmaceutically acceptable carrier.

7. The method of claim 1, wherein said the intrabody comprising the amino acid sequence comprises SEQ ID NO: 1.

8. The method of claim 1, wherein the intrabody binds specifically to a proline rich sequence comprising SEQ ID NO: 17 or SEQ ID NO: 18.

9. A method for inhibiting aggregation of Huntingtin protein in a cell, comprising:

(a) introducing into the cell a single chain intrabody comprising an amino acid sequence comprising: a variable heavy sequence, a variable light chain sequence, and a linker sequence interposed between the variable heavy sequence and the variable light sequence, wherein the variable heavy sequence comprises: a variable heavy CDR1 sequence comprising SEQ ID NO: 21, a variable heavy CDR2 sequence comprising SEQ ID NO: 22, and a variable heavy CDR3 sequence comprising SEQ ID NO: 6; and the variable light sequence comprises: a variable light CDR1 sequence comprising SEQ ID NO: 23, a variable light CDR2 sequence comprising SEQ ID NO: 24, and a variable light CDR3 sequence comprising SEQ ID NO: 10; and (b) maintaining the cell produced in step (a) for a time sufficient for the intrabody to bind to the Huntingtin protein, thereby preventing aggregation of Huntingtin proteins in the cell.

10. A method for inhibiting gene dysregulation caused by aggregation of Huntingtin protein in a cell, comprising:

(a) introducing into the cell an intrabody comprising an amino acid sequence comprising: a variable heavy sequence, a variable light chain sequence, and a linker sequence interposed between the variable heavy sequence and the variable light sequence, wherein the variable heavy sequence comprises: a variable heavy CDR1 sequence comprising SEQ ID NO: 21, a variable heavy CDR2 sequence comprising SEQ ID NO: 22, and a variable heavy CDR3 sequence comprising SEQ ID NO: 6; and the variable light sequence comprises: a variable light CDR1 sequence comprising SEQ ID NO: 23, a variable light CDR2 sequence comprising SEQ ID NO: 24, and a variable light CDR3 sequence comprising SEQ ID NO: 10; and (b) maintaining the cell produced in step (a) for a time sufficient for the intrabody to bind to the Huntingtin protein, thereby preventing gene dysregulation of one or more genes in the cell.

* * * * *

SEQUENCE LISTING

<160> NUMBER OF SEQ ID NOS: 40

<210> SEQ ID NO 1
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Glu Val Gln Leu Val Val Ser Gly Gly Gly Leu Val Lys Pro
1               5                   10                  15

Gly Gly Ser Met Ile Leu Ser Cys Ala Ala Ser Gly Phe Thr Phe Ser
            20                  25                  30

Asn Tyr Ser Met Asn Trp Val Arg Gln Ala Pro Gly Lys Gly Leu Glu
        35                  40                  45

Trp Val Ser Ser Ile Ser Ser Ser Glu Tyr Ile Tyr Tyr Ala Asp
    50                  55                  60

Phe Val Lys Gly Arg Phe Thr Ile Ser Arg Asp Asn Ala Lys Asn Ser
65                  70                  75                  80

Leu Tyr Leu Gln Met Asp Ser Leu Arg Ala Glu Asp Thr Ala Val Tyr
                85                  90                  95

Tyr Cys Ala Trp Pro Gly Tyr Arg Lys Ala Trp Gly Arg Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Val Leu Thr Gln Pro Ala Ser Val Ser Gly
    130                 135                 140

Ser Pro Gly Gln Ser Ile Thr Ile Ser Cys Ala Gly Thr Ser Ser Asp
145                 150                 155                 160

Val Gly Gly Tyr Asn Tyr Val Ser Trp Tyr Gln Gln His Pro Gly Lys
                165                 170                 175

Ala Pro Lys Leu Met Ile Tyr Glu Asp Ser Lys Arg Pro Ser Gly Val
            180                 185                 190

Ser Asn Arg Phe Ser Gly Ser Lys Ser Gly Asn Thr Ala Ser Leu Thr
        195                 200                 205

Ile Ser Gly Leu Arg Ala Glu Asp Glu Ala Asp Tyr Tyr Cys Ser Tyr
    210                 215                 220

Cys Ala Ser Lys Gly His Trp Leu Phe Gly Gly Gly Thr Lys Leu Ala
225                 230                 235                 240

Val Leu Gly Ala Ala Ala Glu Gln Lys Leu Ile Ser
                245                 250

<210> SEQ ID NO 2
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Glu Val Gln Leu Val Val Ser Gly Gly Gly Leu Val Lys Pro
1               5                   10                  15

Gly Gly Ser Met Ile Leu Ser Cys Ala Ala Ser Gly Phe Thr Phe Ser
            20                  25                  30

-continued

```
Asn Tyr Ser Met Asn Trp Val Arg Gln Ala Pro Gly Lys Gly Leu Glu
        35                  40                  45

Trp Val Ser Ser Ile Ser Ser Ser Ser Glu Tyr Ile Tyr Tyr Ala Asp
    50                  55                  60

Phe Val Lys Gly Arg Phe Thr Ile Ser Arg Asp Asn Ala Lys Asn Ser
65                  70                  75                  80

Leu Tyr Leu Gln Met Asp Ser Leu Arg Ala Glu Asp Thr Ala Val Tyr
                85                  90                  95

Tyr Cys Ala His Trp Pro Arg Leu Trp Arg Phe Pro Leu Trp Gly Arg
                100                 105                 110

Gly Thr Leu Val Thr Val Ser Ser Gly Gly Gly Gly Ser Gly Gly Gly
                115                 120                 125

Gly Ser Gly Gly Gly Gly Ser Gln Ser Val Leu Thr Gln Pro Ala Ser
    130                 135                 140

Val Ser Gly Ser Pro Gly Gln Ser Ile Thr Ile Ser Cys Ala Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Leu Met Ile Tyr Glu Asp Ser Lys Arg Pro
                180                 185                 190

Ser Gly Val Ser Asn Arg Phe Ser Gly Ser Lys Ser Gly Asn Thr Ala
                195                 200                 205

Ser Leu Thr Ile Ser Gly Leu Arg Ala Glu Asp Glu Ala Asp Tyr Tyr
    210                 215                 220

Cys Val Leu Asn Met His Trp Ala Asn Phe Gly Gly Gly Thr Lys Leu
225                 230                 235                 240

Ala Val Leu Gly Ala Ala Ala Glu Gln Lys Leu Ile Ser
                245                 250
```

```
<210> SEQ ID NO 3
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

```
Met Ala Glu Val Gln Leu Val Val Ser Gly Gly Gly Leu Val Lys Pro
1               5                   10                  15

Gly Gly Ser Met Ile Leu Ser Cys Ala Ala Ser Gly Phe Thr Phe Ser
                20                  25                  30

Asn Tyr Ser Met Asn Trp Val Arg Gln Ala Pro Gly Lys Gly Leu Glu
        35                  40                  45

Trp Val Ser Ser Ile Ser Ser Ser Ser Glu Tyr Ile Tyr Tyr Ala Asp
    50                  55                  60

Phe Val Lys Gly Arg Phe Thr Ile Ser Arg Asp Asn Ala Lys Asn Ser
65                  70                  75                  80

Leu Tyr Leu Gln Met Asp Ser Leu Arg Ala Glu Asp Thr Ala Val Tyr
                85                  90                  95

Tyr Cys Ala Ile Thr Gly Cys Glu Cys Thr Trp Gly Arg Gly Thr Leu
                100                 105                 110

Val Thr Val Ser Ser Gly Gly Gly Gly Ser Gly Gly Gly Gly Ser Gly
                115                 120                 125
```

-continued

```
Gly Gly Gly Ser Gln Ser Val Leu Thr Gln Pro Ala Ser Val Ser Gly
    130                 135                 140

Ser Pro Gly Gln Ser Ile Thr Ile Ser Cys Ala Gly Thr Ser Ser Asp
145                 150                 155                 160

Val Gly Gly Tyr Asn Tyr Val Ser Trp Tyr Gln Gln His Pro Gly Lys
                165                 170                 175

Ala Pro Lys Leu Met Ile Tyr Glu Asp Ser Lys Arg Pro Ser Gly Val
            180                 185                 190

Ser Asn Arg Phe Ser Gly Ser Lys Ser Gly Asn Thr Ala Ser Leu Thr
        195                 200                 205

Ile Ser Gly Leu Arg Ala Glu Asp Glu Ala Asp Tyr Tyr Cys Ser Cys
    210                 215                 220

Ile Arg Gly Leu Lys Ala Ala Tyr Phe Gly Gly Gly Thr Lys Leu Ala
225                 230                 235                 240

Val Leu Gly Ala Ala Ala Glu Gln Lys Leu Ile Ser
                245                 250
```

<210> SEQ ID NO 4
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Ala Glu Val Gln Leu Val Val Ser Gly Gly Gly Leu Val Lys Pro
1               5                   10                  15

Gly Gly Ser Met Ile Leu Ser Cys Ala Ala Ser Gly Phe Thr Phe Ser
            20                  25                  30

Asn Tyr Ser Met Asn Trp Val Arg Gln Ala Pro Gly Lys Gly Leu Glu
        35                  40                  45

Trp Val Ser Ser Ile Ser Ser Ser Ser Glu Tyr Ile Tyr Tyr Ala Asp
    50                  55                  60

Phe Val Lys Gly Arg Phe Thr Ile Ser Arg Asp Asn Ala Lys Asn Ser
65                  70                  75                  80

Leu Tyr Leu Gln Met Asp Ser Leu Arg Ala Glu Asp Thr Ala Val Tyr
                85                  90                  95

Tyr Cys Ala Ala Ala Val Cys Asn Gly Arg Pro Asp Thr Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Val Leu Thr Gln Pro Ala Ser
    130                 135                 140

Val Ser Gly Ser Pro Gly Gln Ser Ile Thr Ile Ser Cys Ala Gly Thr
145                 150                 155                 160

Ser Ser Asp Val Gly Gly Tyr Asn Tyr Val Ser Trp Tyr Gln Gln His
                165                 170                 175

Pro Gly Lys Ala Pro Lys Leu Met Ile Tyr Glu Asp Ser Lys Arg Pro
            180                 185                 190

Ser Gly Val Ser Asn Arg Phe Ser Gly Ser Lys Ser Gly Asn Thr Ala
        195                 200                 205

Ser Leu Thr Ile Ser Gly Leu Arg Ala Glu Asp Glu Ala Asp Tyr Tyr
    210                 215                 220
```

-continued

```
Cys Gly Tyr Ser Leu Leu Pro Val Leu Phe Gly Gly Gly Thr Lys Leu
225                 230                 235                 240

Ala Val Leu Gly Ala Ala Ala Glu Gln Lys Leu Ile Ser
                245                 250

<210> SEQ ID NO 5
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: His, Ile, Ala or not present
<220> FEATURE:
<221> NAME/KEY: MOD_RES
<222> LOCATION: (104)..(104)
<223> OTHER INFORMATION: Leu, Tyr, Glu or Asn
<220> FEATURE:
<221> NAME/KEY: MOD_RES
<222> LOCATION: (105)..(105)
<223> OTHER INFORMATION: Trp, Arg, Cys or Gly
<220> FEATURE:
<221> NAME/KEY: MOD_RES
<222> LOCATION: (106)..(106)
<223> OTHER INFORMATION: May or may not be present
<220> FEATURE:
<221> NAME/KEY: MOD_RES
<222> LOCATION: (107)..(107)
<223> OTHER INFORMATION: Pro, Lys, Asp or not present
<220> FEATURE:
<221> NAME/KEY: MOD_RES
<222> LOCATION: (226)..(226)
<223> OTHER INFORMATION: May or may not be present
<220> FEATURE:
<221> NAME/KEY: MOD_RES
<222> LOCATION: (227)..(227)
<223> OTHER INFORMATION: Val, Ala, Ile or not present
<220> FEATURE:
<221> NAME/KEY: MOD_RES
<222> LOCATION: (228)..(228)
<223> OTHER INFORMATION: Leu, Ser, Arg or Tyr
<220> FEATURE:
<221> NAME/KEY: MOD_RES
<222> LOCATION: (229)..(229)
<223> OTHER INFORMATION: Asn, Lys, Gly or Ser
<220> FEATURE:
<221> NAME/KEY: MOD_RES
<222> LOCATION: (234)..(234)
<223> OTHER INFORMATION: Asn, Tyr, Leu or not present

<400> SEQUENCE: 5

Met Ala Glu Val Gln Leu Val Val Ser Gly Gly Gly Leu Val Lys Pro
1                   5                   10                  15

Gly Gly Ser Met Ile Leu Ser Cys Ala Ala Ser Gly Phe Thr Phe Ser
                20                  25                  30

Asn Tyr Ser Met Asn Trp Val Arg Gln Ala Pro Gly Lys Gly Leu Glu
        35                  40                  45

Trp Val Ser Ser Ile Ser Ser Ser Ser Glu Tyr Ile Tyr Tyr Ala Asp
    50                  55                  60

Phe Val Lys Gly Arg Phe Thr Ile Ser Arg Asp Asn Ala Lys Asn Ser
65                  70                  75                  80

Leu Tyr Leu Gln Met Asp Ser Leu Arg Ala Glu Asp Thr Ala Val Tyr
                85                  90                  95

Tyr Cys Ala Xaa Trp Pro Cys Xaa Xaa Arg Xaa Thr Trp Gly Arg Gly
            100                 105                 110
```

-continued

```
Thr Leu Val Thr Val Ser Ser Gly Gly Gly Ser Gly Gly Gly
        115                 120                 125

Ser Gly Gly Gly Gly Ser Gln Ser Val Leu Thr Gln Pro Ala Ser Val
        130                 135                 140

Ser Gly Ser Pro Gly Gln Ser Ile Thr Ile Ser Cys Lys Asn Ser Ser
145                     150                 155                 160

Ser Asp Val Gly Gly Tyr Asn Tyr Val Ser Trp Tyr Gln Gln His Pro
                165                 170                 175

Gly Lys Ala Pro Lys Leu Met Ile Tyr Glu Asp Ser Lys Arg Pro Ser
            180                 185                 190

Gly Val Ser Asn Arg Phe Ser Gly Ser Lys Ser Gly Asn Thr Ala Ser
        195                 200                 205

Leu Thr Ile Ser Gly Leu Arg Ala Glu Asp Glu Ala Asp Tyr Tyr Cys
        210                 215                 220

Ser Cys Xaa Xaa Xaa Leu His Trp Ala Xaa Phe Gly Gly Gly Thr Lys
225                     230                 235                 240

Leu Ala Val Leu Gly Ala Ala Ala Glu Gln Lys Leu Ile Ser
                245                 250
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Pro Gly Tyr Arg Lys Ala
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Trp Pro Arg Leu Trp Arg Phe Pro Leu
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Thr Gly Cys Glu Cys Thr
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Ala Ala Val Cys Asn Gly Arg Pro Asp Thr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Cys Ala Ser Lys Gly His Trp Leu
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Leu Asn Met His Trp Ala Asn
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Cys Ile Arg Gly Leu Lys Ala Ala Tyr
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Tyr Ser Leu Leu Pro Val Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: His, Ile, Ala or not present
<220> FEATURE:
<221> NAME/KEY: MOD_RES
<222> LOCATION: (5)..(5)
<223> OTHER INFORMATION: Leu, Tyr, Glu or Asn
<220> FEATURE:
```

```
<221> NAME/KEY: MOD_RES
<222> LOCATION: (6)..(6)
<223> OTHER INFORMATION: Trp, Arg, Cys or Gly
<220> FEATURE:
<221> NAME/KEY: MOD_RES
<222> LOCATION: (7)..(7)
<223> OTHER INFORMATION: May or may not be present
<220> FEATURE:
<221> NAME/KEY: MOD_RES
<222> LOCATION: (8)..(8)
<223> OTHER INFORMATION: Pro, Lys or Asp

<400> SEQUENCE: 14

Xaa Trp Pro Cys Xaa Xaa Arg Xaa Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: May or may not be present
<220> FEATURE:
<221> NAME/KEY: MOD_RES
<222> LOCATION: (3)..(3)
<223> OTHER INFORMATION: Val, Ala, Ile or not present
<220> FEATURE:
<221> NAME/KEY: MOD_RES
<222> LOCATION: (4)..(4)
<223> OTHER INFORMATION: Leu, Ser, Arg or Tyr
<220> FEATURE:
<221> NAME/KEY: MOD_RES
<222> LOCATION: (5)..(5)
<223> OTHER INFORMATION: Asn, Lys, Gly or Ser
<220> FEATURE:
<221> NAME/KEY: MOD_RES
<222> LOCATION: (10)..(10)
<223> OTHER INFORMATION: Leu, Ala or Thr

<400> SEQUENCE: 15

Ser Cys Xaa Xaa Xaa Leu His Trp Ala Xaa
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ser Gly Gly Gly Gly Ser Gly Gly Gly Gly Ser Gly Gly Gly Gly
1               5                   10                  15

Ser

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 17

Pro Gln Leu Pro Gln Pro Pro Pro Gln Ala Gln Pro
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Gly Pro Ala Val Ala Glu Glu Pro Leu His Arg Pro
1               5                   10

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaccatgatt acgccaagct tggctagcca tatgtctaga atggcagaag ttcagctggt         60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atccagtgat ttttttctcg tcgacctcga gtgcggccgc acccagaact gccagtttgg         60

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Ser Gly Gly Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Ser Ser Ile Ser Ser Ser Ser Glu
1               5

<210> SEQ ID NO 23
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 23

Ala Gly Thr Ser Ser Asp Val Gly Gly Tyr
1               5                   10

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Tyr Glu Asp Ser Lys
1               5

<210> SEQ ID NO 25
<211> LENGTH: 19
<212> TYPE: PRT
<213> ORGANISM: Homo sapiens

<400> SEQUENCE: 25

Arg Pro Gln Leu Pro Gln Pro Pro Gln Ala Gln Pro Arg Gly Gly
1               5                   10                  15

Gly Ser Lys

<210> SEQ ID NO 26
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: C-term biotin

<400> SEQUENCE: 26

Arg Pro Gln Leu Pro Gln Pro Pro Gln Ala Gln Pro Arg Gly Gly
1               5                   10                  15

Gly Ser Lys

<210> SEQ ID NO 27
<211> LENGTH: 14
<212> TYPE: PRT
<213> ORGANISM: Homo sapiens

<400> SEQUENCE: 27

Pro Gly Pro Ala Val Ala Glu Glu Pro Leu His Arg Pro Gly
1               5                   10

<210> SEQ ID NO 28
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: C-term biotin

<400> SEQUENCE: 28

Pro Gly Pro Ala Val Ala Glu Glu Pro Leu His Arg Pro Gly
1               5                   10
```

-continued

```
<210> SEQ ID NO 29
<211> LENGTH: 22
<212> TYPE: PRT
<213> ORGANISM: Homo sapiens

<400> SEQUENCE: 29

Met Ala Thr Leu Glu Lys Leu Met Lys Ala Phe Glu Ser Leu Lys Ser
1               5                   10                  15

Phe Gln Gln Gln Gln Gln
            20

<210> SEQ ID NO 30
<211> LENGTH: 28
<212> TYPE: PRT
<213> ORGANISM: Homo sapiens

<400> SEQUENCE: 30

Pro Pro Pro Pro Pro Pro Pro Pro Pro Pro Gln Leu Pro Gln Pro
1               5                   10                  15

Pro Pro Gln Ala Gln Pro Leu Leu Pro Gln Pro Gln
            20                  25

<210> SEQ ID NO 31
<211> LENGTH: 23
<212> TYPE: PRT
<213> ORGANISM: Homo sapiens

<400> SEQUENCE: 31

Pro Pro Pro Pro Pro Pro Pro Pro Pro Gly Pro Ala Val Ala Glu
1               5                   10                  15

Glu Pro Leu His Arg Pro Lys
            20

<210> SEQ ID NO 32
<211> LENGTH: 38
<212> TYPE: PRT
<213> ORGANISM: Homo sapiens

<400> SEQUENCE: 32

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln Gln
            20                  25                  30

Gln Gln Gln Gln Gln Gln
        35

<210> SEQ ID NO 33
<211> LENGTH: 30
<212> TYPE: PRT
<213> ORGANISM: Homo sapiens

<400> SEQUENCE: 33

Gln Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln
            20                  25                  30

<210> SEQ ID NO 34
<211> LENGTH: 103
<212> TYPE: PRT
<213> ORGANISM: Homo sapiens
```

```
<400> SEQUENCE: 34

Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln
        50                  55                  60

Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln
                85                  90                  95

Gln Gln Gln Gln Gln Gln Gln
            100

<210> SEQ ID NO 35
<211> LENGTH: 73
<212> TYPE: PRT
<213> ORGANISM: Homo sapiens

<400> SEQUENCE: 35

Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln
        50                  55                  60

Gln Gln Gln Gln Gln Gln Gln Gln Gln
65                  70

<210> SEQ ID NO 36
<211> LENGTH: 150
<212> TYPE: PRT
<213> ORGANISM: Homo sapiens

<400> SEQUENCE: 36

Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln
        50                  55                  60

Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln
                85                  90                  95

Gln Gln Gln Gln Gln Gln Gln Gln Gln Gln Gln Gln Gln Gln Gln
            100                 105                 110

Gln Gln Gln Gln Gln Gln Gln Gln Gln Gln Gln Gln Gln Gln Gln
        115                 120                 125
```

-continued

```
Gln Gln Gln Gln Gln Gln Gln Gln Gln Gln Gln Gln Gln Gln
    130                 135                 140

Gln Gln Gln Gln Gln Gln
145                 150

<210> SEQ ID NO 37
<211> LENGTH: 120
<212> TYPE: PRT
<213> ORGANISM: Mus sp.

<400> SEQUENCE: 37

Gln Gln Gln Gln Gln Gln Gln Gln Gln Gln Gln Gln Gln Gln Gln
1               5                   10                  15

Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln
    50                  55                  60

Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln
                85                  90                  95

Gln Gln Gln Gln Gln Gln Gln Gln Gln Gln Gln Gln Gln Gln Gln
            100                 105                 110

Gln Gln Gln Gln Gln Gln Gln Gln
        115                 120

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5

<210> SEQ ID NO 39
<211> LENGTH: 23
<212> TYPE: PRT
<213> ORGANISM: Homo sapiens

<400> SEQUENCE: 39

Gln Gln Gln Gln Gln Gln Gln Gln Gln Gln Gln Gln Gln Gln Gln
1               5                   10                  15

Gln Gln Gln Gln Gln Gln Gln
            20

<210> SEQ ID NO 40
<211> LENGTH: 758
<212> TYPE: PRT
<213> ORGANISM: Homo sapiens

<400> SEQUENCE: 40

Met Ala Glu Pro Arg Gln Glu Phe Glu Val Met Glu Asp His Ala Gly
1               5                   10                  15
```

-continued

```
Thr Tyr Gly Leu Gly Asp Arg Lys Asp Gln Gly Gly Tyr Thr Met His
         20              25              30

Gln Asp Gln Glu Gly Asp Thr Asp Ala Gly Leu Lys Glu Ser Pro Leu
         35              40              45

Gln Thr Pro Thr Glu Asp Gly Ser Glu Glu Pro Gly Ser Glu Thr Ser
    50              55              60

Asp Ala Lys Ser Thr Pro Thr Ala Glu Asp Val Thr Ala Pro Leu Val
65              70              75              80

Asp Glu Gly Ala Pro Gly Lys Gln Ala Ala Ala Gln Pro His Thr Glu
                85              90              95

Ile Pro Glu Gly Thr Thr Ala Glu Glu Ala Gly Ile Gly Asp Thr Pro
        100             105             110

Ser Leu Glu Asp Glu Ala Ala Gly His Val Thr Gln Glu Pro Glu Ser
        115             120             125

Gly Lys Val Val Gln Glu Gly Phe Leu Arg Glu Pro Gly Pro Pro Gly
    130             135             140

Leu Ser His Gln Leu Met Ser Gly Met Pro Gly Ala Pro Leu Leu Pro
145             150             155             160

Glu Gly Pro Arg Glu Ala Thr Arg Gln Pro Ser Gly Thr Gly Pro Glu
                165             170             175

Asp Thr Glu Gly Gly Arg His Ala Pro Glu Leu Leu Lys His Gln Leu
        180             185             190

Leu Gly Asp Leu His Gln Glu Gly Pro Pro Leu Lys Gly Ala Gly Gly
        195             200             205

Lys Glu Arg Pro Gly Ser Lys Glu Glu Val Asp Glu Asp Arg Asp Val
    210             215             220

Asp Glu Ser Ser Pro Gln Asp Ser Pro Pro Ser Lys Ala Ser Pro Ala
225             230             235             240

Gln Asp Gly Arg Pro Pro Gln Thr Ala Ala Arg Glu Ala Thr Ser Ile
            245             250             255

Pro Gly Phe Pro Ala Glu Gly Ala Ile Pro Leu Pro Val Asp Phe Leu
        260             265             270

Ser Lys Val Ser Thr Glu Ile Pro Ala Ser Glu Pro Asp Gly Pro Ser
        275             280             285

Val Gly Arg Ala Lys Gly Gln Asp Ala Pro Leu Glu Phe Thr Phe His
    290             295             300

Val Glu Ile Thr Pro Asn Val Gln Lys Glu Gln Ala His Ser Glu Glu
305             310             315             320

His Leu Gly Arg Ala Ala Phe Pro Gly Ala Pro Gly Glu Gly Pro Glu
                325             330             335

Ala Arg Gly Pro Ser Leu Gly Glu Asp Thr Lys Glu Ala Asp Leu Pro
            340             345             350

Glu Pro Ser Glu Lys Gln Pro Ala Ala Ala Pro Arg Gly Lys Pro Val
        355             360             365

Ser Arg Val Pro Gln Leu Lys Ala Arg Met Val Ser Lys Ser Lys Asp
    370             375             380

Gly Thr Gly Ser Asp Asp Lys Lys Ala Lys Thr Ser Thr Arg Ser Ser
385             390             395             400

Ala Lys Thr Leu Lys Asn Arg Pro Cys Leu Ser Pro Lys His Pro Thr
            405             410             415

Pro Gly Ser Ser Asp Pro Leu Ile Gln Pro Ser Ser Pro Ala Val Cys
        420             425             430
```

-continued

```
Pro Glu Pro Pro Ser Ser Pro Lys Tyr Val Ser Ser Val Thr Ser Arg
        435             440             445

Thr Gly Ser Ser Gly Ala Lys Glu Met Lys Leu Lys Gly Ala Asp Gly
    450             455             460

Lys Thr Lys Ile Ala Thr Pro Arg Gly Ala Ala Pro Pro Gly Gln Lys
465             470             475             480

Gly Gln Ala Asn Ala Thr Arg Ile Pro Ala Lys Thr Pro Pro Ala Pro
                485             490             495

Lys Thr Pro Pro Ser Ser Gly Glu Pro Pro Lys Ser Gly Asp Arg Ser
            500             505             510

Gly Tyr Ser Ser Pro Gly Ser Pro Gly Thr Pro Gly Ser Arg Ser Arg
        515             520             525

Thr Pro Ser Leu Pro Thr Pro Pro Thr Arg Glu Pro Lys Lys Val Ala
    530             535             540

Val Val Arg Thr Pro Pro Lys Ser Pro Ser Ser Ala Lys Ser Arg Leu
545             550             555             560

Gln Thr Ala Pro Val Pro Met Pro Asp Leu Lys Asn Val Lys Ser Lys
                565             570             575

Ile Gly Ser Thr Glu Asn Leu Lys His Gln Pro Gly Gly Gly Lys Val
                580             585             590

Gln Ile Ile Asn Lys Lys Leu Asp Leu Ser Asn Val Gln Ser Lys Cys
        595             600             605

Gly Ser Lys Asp Asn Ile Lys His Val Pro Gly Gly Gly Ser Val Gln
    610             615             620

Ile Val Tyr Lys Pro Val Asp Leu Ser Lys Val Thr Ser Lys Cys Gly
625             630             635             640

Ser Leu Gly Asn Ile His His Lys Pro Gly Gly Gly Gln Val Glu Val
                645             650             655

Lys Ser Glu Lys Leu Asp Phe Lys Asp Arg Val Gln Ser Lys Ile Gly
            660             665             670

Ser Leu Asp Asn Ile Thr His Val Pro Gly Gly Gly Asn Lys Lys Ile
            675             680             685

Glu Thr His Lys Leu Thr Phe Arg Glu Asn Ala Lys Ala Lys Thr Asp
    690             695             700

His Gly Ala Glu Ile Val Tyr Lys Ser Pro Val Val Ser Gly Asp Thr
705             710             715             720

Ser Pro Arg His Leu Ser Asn Val Ser Ser Thr Gly Ser Ile Asp Met
            725             730             735

Val Asp Ser Pro Gln Leu Ala Thr Leu Ala Asp Glu Val Ser Ala Ser
            740             745             750

Leu Ala Lys Gln Gly Leu
            755
```